US009486123B2

(12) United States Patent
Morita et al.

(10) Patent No.: US 9,486,123 B2
(45) Date of Patent: Nov. 8, 2016

(54) ENDOSCOPE SYSTEM WHICH ENLARGES AN AREA OF A CAPTURED IMAGE, AND METHOD FOR OPERATING ENDOSCOPE SYSTEM

(71) Applicant: OLYMPUS CORPORATION, Shibuya-ku, Tokyo (JP)

(72) Inventors: Yasunori Morita, Hachioji (JP); Seigo On, Hachioji (JP); Jumpei Takahashi, Tokyo (JP); Naoya Kuriyama, Hachioji (JP); Keiji Higuchi, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 290 days.

(21) Appl. No.: 14/059,221

(22) Filed: Oct. 21, 2013

(65) Prior Publication Data

US 2014/0046131 A1 Feb. 13, 2014

Related U.S. Application Data

(63) Continuation of application No. PCT/JP2012/062975, filed on May 22, 2012.

(30) Foreign Application Priority Data

May 27, 2011 (JP) ................................. 2011-119063

(51) Int. Cl.
*A61B 1/04* (2006.01)
*A61B 1/00* (2006.01)
(Continued)

(52) U.S. Cl.
CPC ....... *A61B 1/00009* (2013.01); *A61B 1/00177* (2013.01); *A61B 1/00179* (2013.01); *A61B 1/00181* (2013.01); *A61B 1/00188* (2013.01); *A61B 1/06* (2013.01); *G02B 21/365* (2013.01); *G02B 23/2484* (2013.01); *G02B 27/0025* (2013.01); *A61B 1/00006* (2013.01);
(Continued)

(58) Field of Classification Search
CPC .......... A61B 1/00009; A61B 1/00188; G02B 21/365; H04N 5/23296
See application file for complete search history.

(56) References Cited

U.S. PATENT DOCUMENTS 4,805,597 A 2/1989 Iwakoshi
5,269,289 A 12/1993 Takehana et al.
(Continued)

FOREIGN PATENT DOCUMENTS

DE 10126587 A1 12/2001
JP 63-271217 A 11/1988
(Continued)

OTHER PUBLICATIONS

Machine language translation of JP 04-102437 A, Apr. 1992.*
(Continued)

*Primary Examiner* — John P Leubecker
(74) *Attorney, Agent, or Firm* — Holtz, Holtz & Volek PC

(57) ABSTRACT

An endoscope system includes an image acquisition section, an attention area setting section, and a scaling section. The image acquisition section acquires a captured image that includes an object image. The attention area setting section sets an attention area within the captured image based on information from the endoscope system. The scaling section performs a local scaling process that relatively enlarges the attention area as compared with another area.

6 Claims, 65 Drawing Sheets

(51) Int. Cl.

| | | |
|---|---|---|
| *G02B 27/00* | (2006.01) | |
| *A61B 1/06* | (2006.01) | |
| *G02B 21/36* | (2006.01) | |
| *G02B 23/24* | (2006.01) | |
| *G02B 13/06* | (2006.01) | |
| *A61B 1/273* | (2006.01) | |
| *A61B 1/31* | (2006.01) | |

(52) U.S. Cl.
CPC ............... *A61B 1/043* (2013.01); *A61B 1/273* (2013.01); *A61B 1/31* (2013.01); *G02B 13/06* (2013.01)

(56) References Cited

U.S. PATENT DOCUMENTS

| | | | |
|---|---|---|---|
| 5,469,254 A | 11/1995 | Konomura | |
| 5,696,530 A * | 12/1997 | Maejima | G06F 3/0481 345/671 |
| 6,036,637 A * | 3/2000 | Kudo | A61B 1/00039 600/102 |
| 6,491,628 B1 | 12/2002 | Kobayashi | |
| 8,808,164 B2 * | 8/2014 | Hoffman | A61B 19/2203 600/101 |
| 2003/0076411 A1 | 4/2003 | Iida et al. | |
| 2004/0169668 A1* | 9/2004 | Yamada | G06T 7/0012 345/660 |
| 2006/0178561 A1* | 8/2006 | Nakano | A61B 1/00193 600/117 |
| 2008/0231692 A1* | 9/2008 | Higuchi | A61B 1/0005 348/65 |
| 2009/0073260 A1 | 3/2009 | Nagase et al. | |
| 2009/0149713 A1 | 6/2009 | Niida | |
| 2009/0207248 A1* | 8/2009 | Cilia | H04N 19/136 348/143 |
| 2009/0225158 A1 | 9/2009 | Kimoto | |
| 2010/0121143 A1* | 5/2010 | Sugimoto | A61B 1/00009 600/109 |
| 2010/0157039 A1 | 6/2010 | Sugai | |
| 2010/0268026 A1 | 10/2010 | Takizawa | |
| 2010/0312057 A1 | 12/2010 | Konno | |
| 2011/0018987 A1* | 1/2011 | Doi | H04N 7/183 348/65 |
| 2011/0273784 A1 | 11/2011 | Mizusawa | |
| 2011/0275889 A1 | 11/2011 | Kase et al. | |
| 2011/0279915 A1 | 11/2011 | Mizusawa | |
| 2011/0305388 A1 | 12/2011 | Wedi et al. | |
| 2012/0076372 A1 | 3/2012 | Nishimura et al. | |
| 2013/0111399 A1* | 5/2013 | Rose | G06T 3/0025 715/800 |
| 2014/0036050 A1* | 2/2014 | Yoshino | A61B 1/00009 348/65 |
| 2014/0107415 A1* | 4/2014 | Amling | A61B 1/045 600/109 |

FOREIGN PATENT DOCUMENTS

| | | |
|---|---|---|
| JP | 01-213615 A | 8/1989 |
| JP | 04-102437 A | 4/1992 |
| JP | 04-221527 A | 8/1992 |
| JP | 08-038433 A | 2/1996 |
| JP | 09080323 A | 3/1997 |
| JP | 09-098943 A | 4/1997 |
| JP | 09-149876 A | 6/1997 |
| JP | 09-262206 A | 10/1997 |
| JP | 10-243919 A | 9/1998 |
| JP | 10-276974 A | 10/1998 |
| JP | 2000166936 A | 6/2000 |
| JP | 2001-221960 A | 8/2001 |
| JP | 2001-340292 A | 12/2001 |
| JP | 2002-125926 A | 5/2002 |
| JP | 2002-263064 A | 9/2002 |
| JP | 2003-180631 A | 7/2003 |
| JP | 2004321610 A | 11/2004 |
| JP | 2005124756 A | 5/2005 |
| JP | 2006-021035 A | 1/2006 |
| JP | 2009-072316 A | 4/2009 |
| JP | 2010-169792 A | 8/2010 |
| JP | 2010-194261 A | 9/2010 |
| WO | WO 2010/055800 A1 | 5/2010 |
| WO | 2011055614 A1 | 5/2011 |

OTHER PUBLICATIONS

Extended European Search Report dated Feb. 25, 2015, issued in counterpart European Application No. 12794085.6.
International Search Report (ISR) dated Sep. 4, 2012 (and English translation thereof) in International Application No. PCT/JP2012/062975.
U.S. Appl. No. 14/086,330, filed Nov. 21, 2013, First Named Inventor: Yasunori Morita, Title: "Endoscope System and Method for Operating Endoscope System".

* cited by examiner

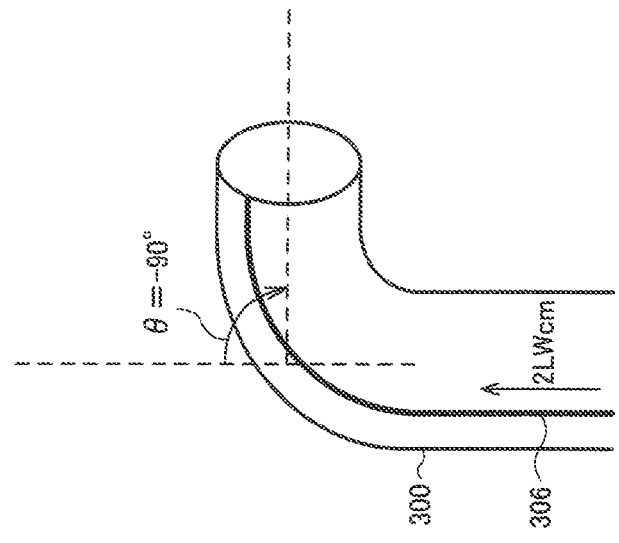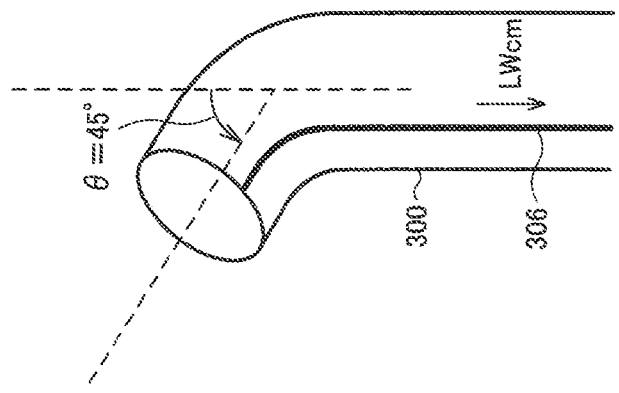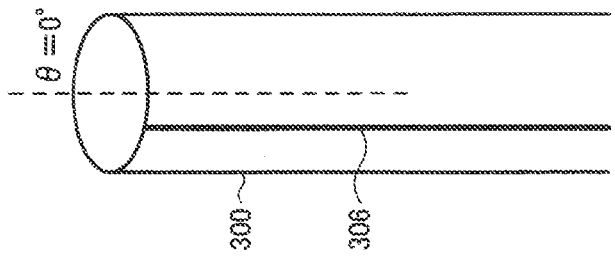

| ANGLE | ENLARGEMENT FACTOR A |
|---|---|
| $0 \sim \theta1$ | 1 |
| $\theta1 \sim \theta2$ | A1 |
| ⋮ | ⋮ |
| $\theta n-1 \sim \theta max$ | $An-1$ |

FIG. 44

| G2(0,0) | B2(1,0) | G2(2,0) | B2(3,0) | G2(4,0) | B2(5,0) |
| --- | --- | --- | --- | --- | --- |
| B2(0,1) | G2(1,1) | B2(2,1) | G2(3,1) | B2(4,1) | G2(5,1) |
| G2(0,2) | B2(1,2) | G2(2,2) | B2(3,2) | G2(4,2) | B2(5,2) |
| B2(0,3) | G2(1,3) | B2(2,3) | G2(3,3) | B2(4,3) | G2(5,3) |

IMAGE BEFORE DISTORTION CORRECTION

IMAGE AFTER DISTORTION CORRECTION

ENDOSCOPE SYSTEM WHICH ENLARGES AN AREA OF A CAPTURED IMAGE, AND METHOD FOR OPERATING ENDOSCOPE SYSTEM

CROSS REFERENCE TO RELATED APPLICATION

This application is a continuation of International Patent Application No. PCT/JP2012/062975, having an international filing date of May 22, 2012, which designated the United States, the entirety of which is incorporated herein by reference. Japanese Patent Application No. 2011-119063 filed on May 27, 2011 is also incorporated herein by reference in its entirety.

BACKGROUND

The present invention relates to an endoscope system, a method for operating an endoscope system, and the like.

An endoscope system has been widely used that applies illumination light to tissue inside a body cavity, and allows the user to perform diagnosis and procedures using an image obtained by capturing reflected light from the tissue. An image sensor (e.g., CCD image sensor or CMOS image sensor), and an objective lens that optically forms an image of the object are provided on the end of the insertion section. A wide-angle objective lens is normally used as the objective lens of the endoscope in order to prevent a situation in which a lesion area is missed. For example, an objective lens having an angle of view of 170° has been used.

A wider field of view can be observed by utilizing an objective lens that forms an image of the side field of view of the end of the insertion section (see JP-A-2010-169792, for example). Since the back side of folds inside a body cavity can be observed by increasing the field of view, for example, it is possible to suppress a situation in which a lesion area that is difficult to observe is missed.

JP-A-2001-221960 discloses a method that displays a wide-angle image and an enlarged image side by side. JP-A-9-149876 discloses a method that detects position information about an attention area within a wide-angle image, and displays an enlarged image of the attention area on a monitor.

SUMMARY

According to one aspect of the invention, there is provided an endoscope system comprising:

an image acquisition section that acquires a captured image that includes an object image;

an attention area setting section that sets an attention area within the captured image based on information from the endoscope system; and a scaling section that performs a local scaling process that relatively enlarges the attention area as compared with another area.

According to another aspect of the invention, there is provided a method for operating an endoscope system comprising:

acquiring a captured image that includes an object image;

setting an attention area within the captured image based on information from the endoscope system; and performing a local scaling process that relatively enlarges the attention area as compared with another area.

BRIEF DESCRIPTION OF DRAWINGS

FIGS. 26A to 26C are views illustrating a curve operation.

FIG. 44 illustrates an example of image signals captured by a second image sensor.

DESCRIPTION OF EXEMPLARY EMBODIMENTS

According to one embodiment of the invention, there is provided an endoscope system comprising:

an image acquisition section that acquires a captured image that includes an object image;

an attention area setting section that sets an attention area within the captured image based on information from the endoscope system; and a scaling section that performs a local scaling process that relatively enlarges the attention area as compared with another area.

According to one embodiment of the invention, the attention area is set within the captured image based on the information from the endoscope system, and the local scaling process that relatively enlarges the attention area as compared with another area is performed. This makes it possible to display the attention area at an appropriate size while allowing the user to observe the entire object.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Outline

Figure 1:
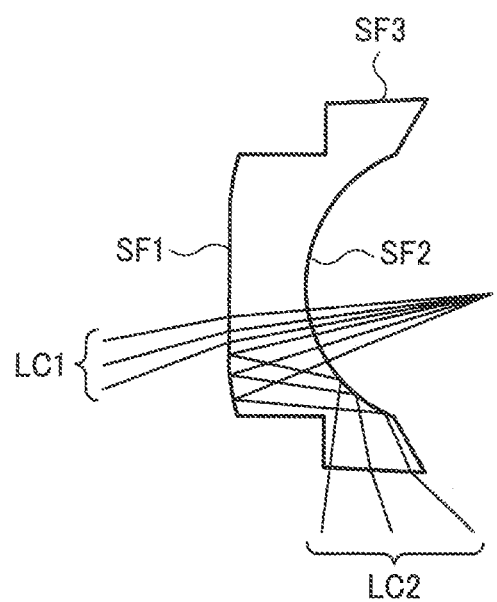
FIG. 1 illustrates a configuration example of an objective optical system.

An outline of several embodiments of the invention is described below. JP-A-2010-169792 discloses an objective optical system that makes it possible to observe the front field of view and the side field of view of the end of the scope. FIG. 1 illustrates a configuration example of the objective optical system disclosed in JP-A-2010-169792. As illustrated in FIG. 1, a light beam LC1 from the front field of view enters through a surface SF1, and a light beam LC2 from the side field of view enters through a surface SF3. The light beams LC1 and LC2 are refracted or reflected by the surfaces SF1 and SF2 to form an image of the front field of view and the side field of view.

It is possible to observe an area inside a body cavity with a wider field of view as compared with a normal endoscope system by utilizing such an objective lens. The details thereof are described below with reference to FIGS. 2A to 2D.

Figure 2B:
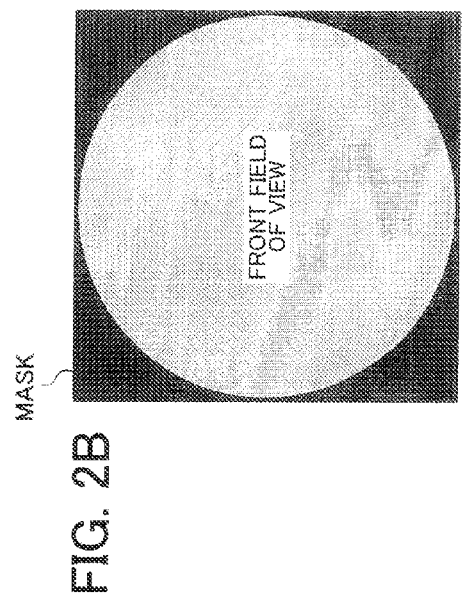
FIGS. 2A to 2D are views illustrating an outline of several embodiments of the invention.
Figure 2D:
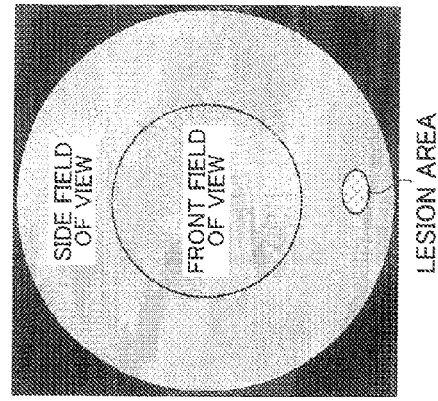
Figure 2A:
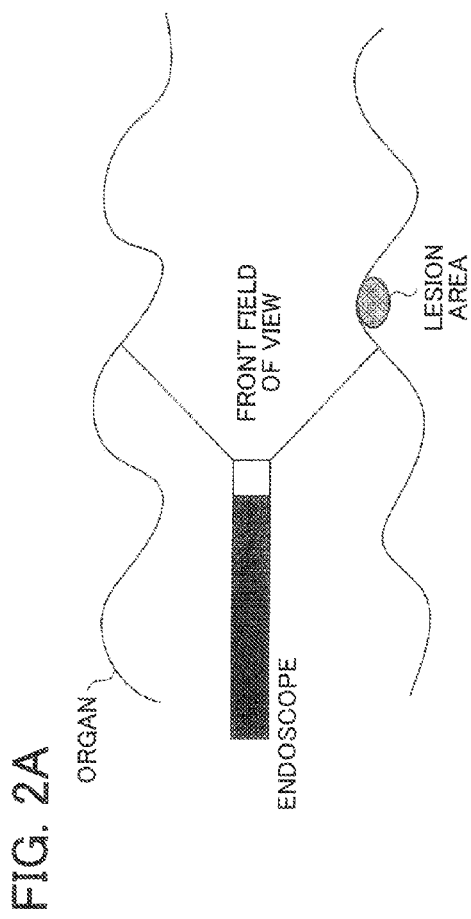

When screening a lesion area that may be present in a hollow tubular organ, the organ is observed while inserting or withdrawing the scope that is positioned parallel to the axial direction of the organ (see FIG. 2A). When using only the front field of view, a lesion area that is positioned on the wall surface of the organ is screened by folds or the like, and cannot be captured. Therefore, the lesion area cannot be observed within the captured image, and may be missed (see FIG. 2B).

In contrast, when the side field of view can be observed (see FIG. 2C), a lesion area that is positioned on the back side of folds can be observed within the side field of view. Therefore, the lesion area can be observed within the captured image (see FIG. 2D), and it is possible to suppress a situation in which a lesion area is missed.

However, since the amount of information included in the image relatively increases as compared with the case of using a normal endoscope as a result of increasing the field of view, the object that attracts the user's attention may be displayed to have a relatively small size with respect to the entire image.

For example, JP-A-2001-221960 discloses an endoscope system that displays a wide-angle image and an enlarged image side by side.

According to this method, however, since the operator must perform diagnosis while always observing a plurality of images, the burden imposed on the operator increases. Moreover, the operator may miss a lesion area when the operator temporarily pays attention to only one image.

JP-A-9-149876 discloses an endoscope system that detects position information about an attention area within a wide-angle image, and displays an enlarged image of the attention area on a monitor based on the position information.

According to this method, however, since only the attention area within the image is enlarged, it is difficult to determine the entirety of a hollow tubular organ, and smoothly insert or withdraw the scope. This makes it difficult to perform reliable and efficient screening.

Figure 12:
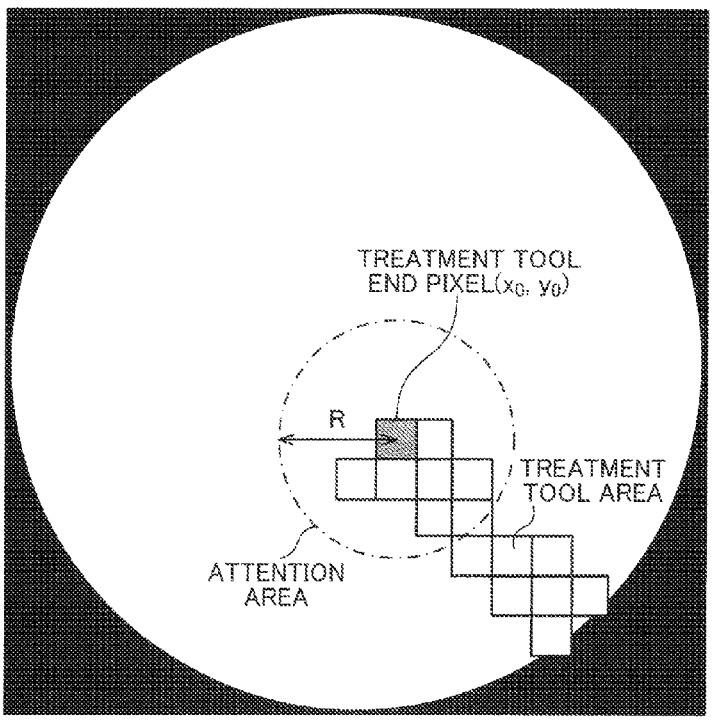
FIG. 12 is a view illustrating a process performed by an attention area setting section.

According to several embodiments of the invention, an attention area is set within a captured image, and relatively enlarged with respect to the captured image (see FIG. 12). According to the above configuration, since the attention area can be enlarged while maintaining the angle of view of the captured image, the visibility of the attention area can be improved while allowing the user to observe the entire wide field of view. It is possible to improve the operability of the scope by providing a wide field of view, and allows the user to easily perform diagnosis and procedures on a lesion area by enlarging the attention area.

2. First Embodiment
2.1. Endoscope System

An endoscope system according to a first embodiment that enlarges the attention area while maintaining the angle of view of the captured image is described in detail below.

Figure 3:
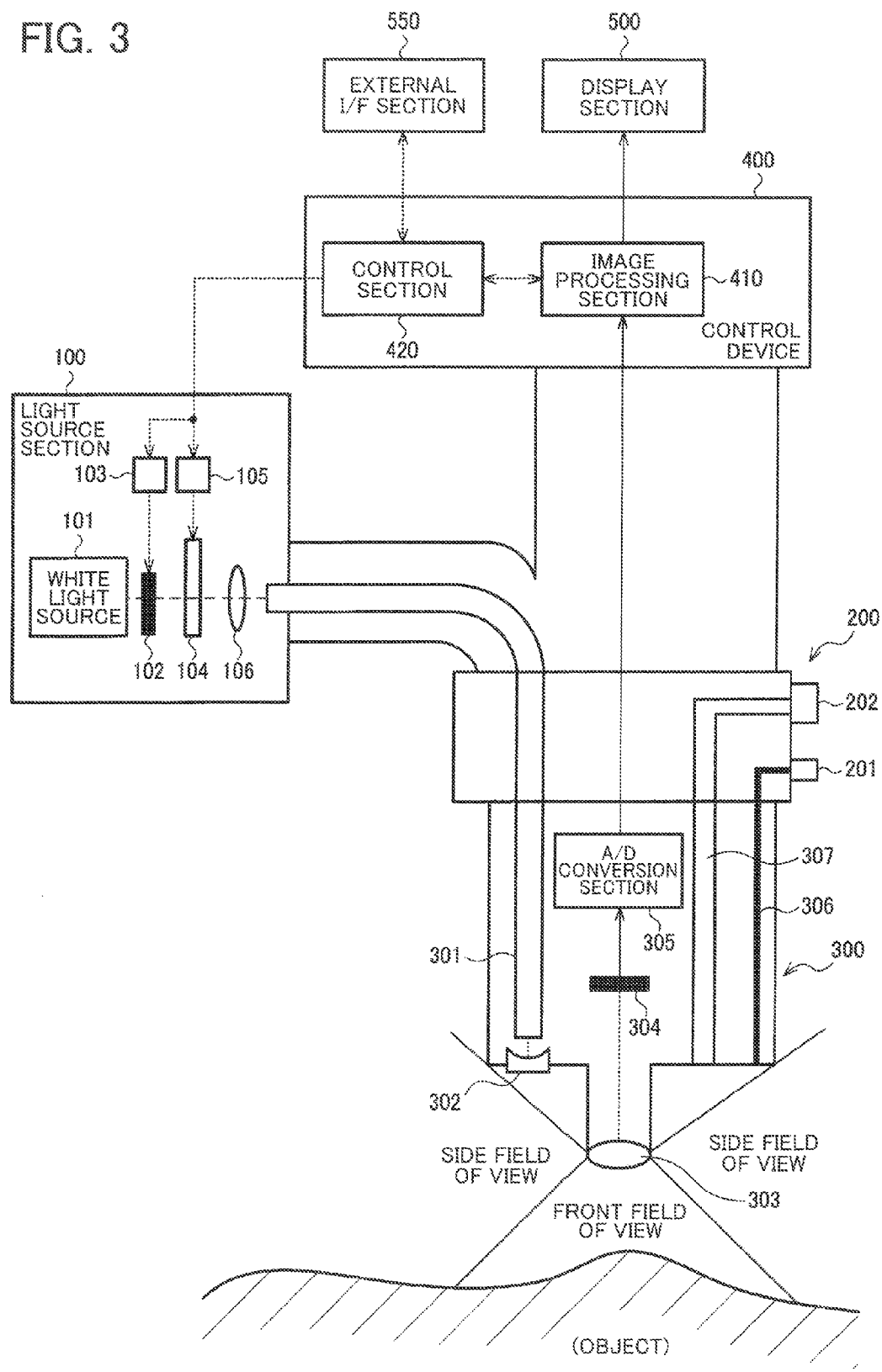
FIG. 3 illustrates a configuration example of an endoscope system according to a first embodiment.

FIG. 3 illustrates a configuration example of the endoscope system according to the first embodiment. The endoscope system includes a light source section 100, an operation section 200, an insertion section 300, a control device 400 (processor section), a display section 500, and an external I/F section 550.

The light source section 100 includes a white light source 101, a light source aperture 102, a light source aperture driver section 103 that drives the light source aperture 102, and a rotary color filter 104 that includes a plurality of filters that differ in spectral transmittance. The light source section 100 also includes a rotation driver section 105 that drives the rotary color filter 104, and a condenser lens 106 that focuses light that has passed through the rotary color filter 104 on the incident end face of a light guide fiber 301.

The light source aperture driver section 103 adjusts the intensity of light by opening or closing the light source aperture 102 based on a control signal output from a control section 420 included in the control device 400.

Figure 4:
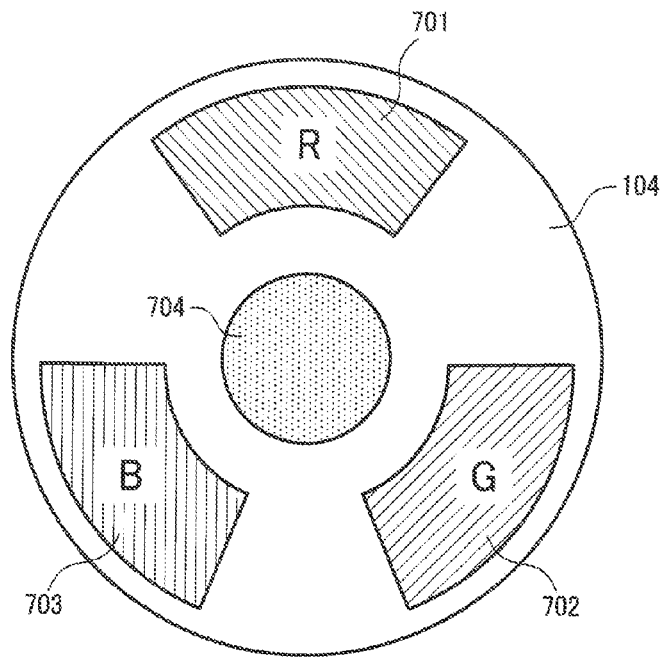
FIG. 4 illustrates a detailed configuration example of a rotary color filter.
Figure 5:
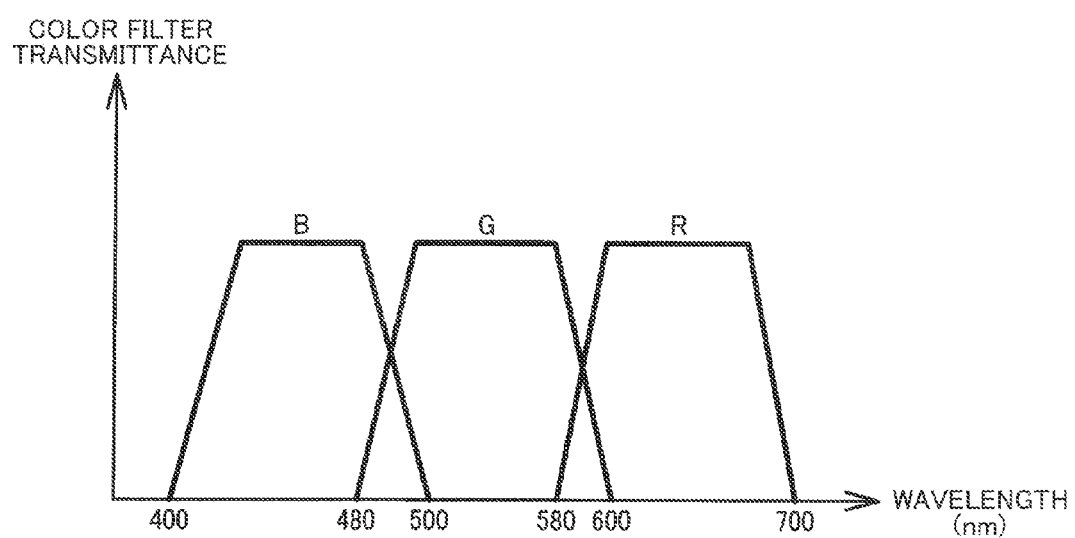
FIG. 5 illustrates an example of the spectral characteristics of a color filter.

FIG. 4 illustrates a detailed configuration example of the rotary color filter 104. The rotary color filter 104 includes a red (R) color filter 701, a green (G) color filter 702, a blue (B) color filter 703, and a rotary motor 704. FIG. 5 illustrates an example of the spectral characteristics of the color filters 701 to 703.

The rotation driver section 105 rotates the rotary color filter 104 at a given rotational speed in synchronization with the imaging period of an image sensor 304 based on the control signal output from the control section 420. For example, when the rotary color filter 104 is rotated at 20 revolutions per second, each color filter crosses incident white light every 1/60th of a second. In this case, the image sensor 304 captures and transfers image signals every 1/60th of a second.

The image sensor 304 is a monochrome image sensor, for example. Specifically, the endoscope system according to the first embodiment frame-sequentially captures an R image, a G image, and a B image every 1/60th of a second.

The operation section 200 includes a curve operation lever 201 that is used to curve the insertion section 300, and an insertion opening 202 into which a treatment tool (e.g., forceps) is inserted.

The curve operation lever 201 is connected to a curve operation wire 306. The curve operation wire 306 extends through the insertion section 300, and is secured on the end of the insertion section 300. The operator curves the insertion section 300 by pulling or loosening the curve operation wire 306 by operating the curve operation lever 201. The insertion opening 202 communicates with an insertion channel 307 into which the treatment tool is inserted.

The insertion section 300 is formed to be elongated and curved so that the insertion section 300 can be inserted into a body cavity or the like. The insertion section 300 includes the light guide fiber 301 that guides the light focused by the light source section 100 to an illumination lens 302, and the illumination lens 302 that diffuses the light guided by the light guide fiber 301 to illuminate the observation target. The insertion section 300 also includes an objective optical system 303 that focuses the reflected light from the observation target, the image sensor 304 that detects the focused reflected light, and an A/D conversion section 305 that converts analog image signals obtained by photoelectric conversion performed by the image sensor 304 into digital image signals. The insertion section 300 also includes the curve operation wire 306 that extends through the insertion section 300, and is secured on the end of the insertion section 300, and the insertion channel 307 that receives the treatment tool inserted through the operation section 200.

The objective optical system 303 (objective lens in a narrow sense) protrudes from the end of the insertion section 300, and forms an image of the front field of view and the side field of view. The objective optical system 303 has an angle of view of 230°, for example.

The image sensor 304 is a monochrome single-chip image sensor, for example. The image sensor 304 is implemented by a CCD image sensor, a CMOS image sensor, or the like.

The control device 400 controls each section of the endoscope system, and performs image processing. The control device 400 includes an image processing section 410 that performs an attention area setting process and an image scaling process, and the control section 420.

The digital image signals obtained by the A/D conversion section 305 are transmitted to the image processing section 410. The image signals processed by the image processing section 410 are transmitted to the display section 500. The control section 420 controls each section of the endoscope system. The control section 420 is connected to the light source aperture driver section 103, the rotation driver section 105, the image processing section 410, and the external I/F section 550, and controls the light source aperture driver section 103, the rotation driver section 105, the image processing section 410, and the external I/F section 550.

The display section 500 is a display that can display a moving image (movie), and is implemented by a CRT, a liquid crystal monitor, or the like.

The external I/F section 550 is an interface that allows the user to perform an input operation and the like on the endoscope system. The external I/F section 500 includes a power switch (power ON/OFF switch), a mode (e.g., imaging mode) switch button, and the like. The external I/F section 500 transmits the input information to the control section 420.

2.2. Image Processing Section

Figure 6:
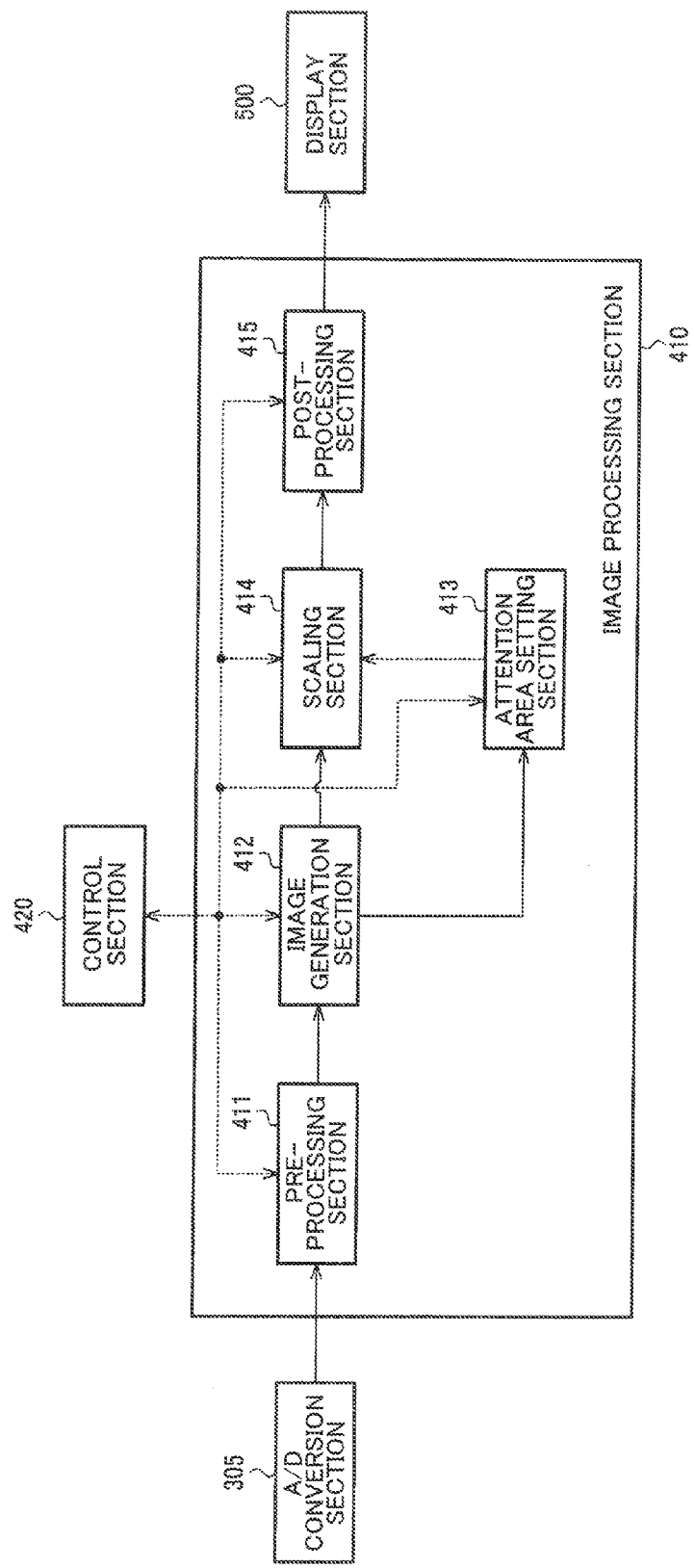
FIG. 6 illustrates a detailed configuration example of an image processing section according to the first embodiment.

FIG. 6 illustrates a detailed configuration example of the image processing section 410 according to the first embodiment. The image processing section 410 includes a preprocessing section 411, an image generation section 412, an attention area setting section 413, a scaling section 414, and a post-processing section 415.

The A/D conversion section 305 is connected to the preprocessing section 411. The preprocessing section 411 is connected to the image generation section 412. The image generation section 412 is connected to the attention area setting section 413 and the scaling section 414. The attention area setting section 413 is connected to the scaling section 414. The scaling section 414 is connected to the post-processing section 415. The post-processing section 415 is connected to the display section 500. The control section 420 is bidirectionally connected to the preprocessing section 411, the image generation section 412, the attention area setting section 413, the scaling section 414, and the post-processing section 415, and controls the preprocessing section 411, the image generation section 412, the attention area setting section 413, the scaling section 414, and the post-processing section 415.

The preprocessing section 411 performs an OB clamp process, a gain control process, and a WB correction process on the image signals input from the A/D conversion section 305 using an OB clamp value, a gain correction value, and a WB coefficient stored in the control section 420. The preprocessing section 411 transmits the resulting image signals to the image generation section 412.

The image generation section 412 performs an image generation process on the frame-sequential image signals processed by the preprocessing section 411 based on the control signal output from the control section 420. Specifically, the image generation section 412 stores the image signals that have been input frame sequentially and correspond to each color light (R, G, or B) on a frame basis, and simultaneously reads the stored image signals that correspond to each color light. The image generation section 412 transmits the image signals obtained by the image generation process to the attention area setting section 413 and the scaling section 414.

The attention area setting section 413 sets the attention area based on the image signals obtained by the image generation process. Specifically, the attention area setting section 413 detects an area in which the treatment tool is captured, and sets the attention area around the end of the treatment tool. The details of the process performed by the attention area setting section 413 are described later.

The scaling section 414 performs the scaling process on the image while (substantially) maintaining the angle of view to enlarge the attention area. Specifically, the scaling section 414 enlarges the attention area by a given scaling factor. The scaling section 414 may enlarge the attention area while reducing another area. The details of the process performed by the scaling section 414 are described later.

The post-processing section 415 performs a grayscale transformation process, a color process, and a contour enhancement process on the image obtained by the scaling process using a grayscale transformation coefficient, a color conversion coefficient, and a contour enhancement coefficient stored in the control section 420. The post-processing section 415 transmits the resulting image signals to the display section 500.

2.3. Attention Area Setting Section

The details of the process performed by the attention area setting section 413 are described below. The attention area setting section 413 detects a treatment tool area that includes pixels that form an image of the treatment tool from the image signals obtained by the image generation process, and sets the attention area based on the detected treatment tool area. The following description is given taking an example when detecting a highly reflective metal treatment tool (e.g., forceps).

Since the treatment tool is positioned close to the image sensor 304, the luminance signal value of the treatment tool is sufficiently larger than that of the organ. Therefore, a high-luminance area included in the image signals is detected as the treatment tool area. Specifically, the luminance signal value $Y(x, y)$ of an attention pixel (processing target pixel) having coordinates $(x, y)$ is calculated by the following expression (1).

$$Y(x,y)=0.299 \cdot R(x,y)+0.587 \cdot G(x,y)+0.114 \cdot B(x,y) \qquad (1)$$

where, $R(x, y)$, $G(x, y)$, and $B(x, y)$ are respectively the R image signal, the G image signal, and the B image signal at the coordinates $(x, y)$.

Figure 7:
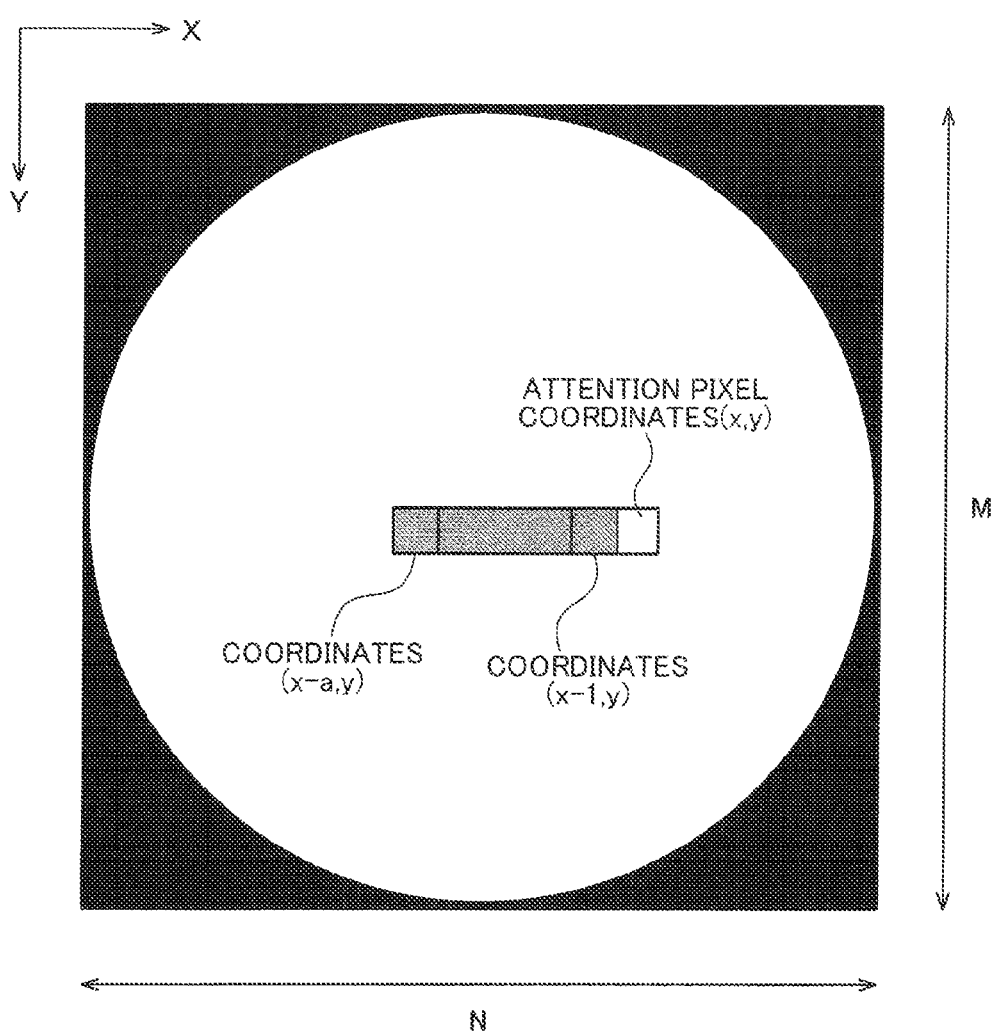
FIG. 7 is a view illustrating a process performed by an attention area setting section.

The average luminance $Yave(x, y)$ (i.e., the average value of the luminance signal values at the coordinates $(x-a, y)$ to $(x-1, y)$ on the left side of the attention pixel) (see FIG. 7) is calculated by the following expression (2). In FIG. 7, the image indicated by the image signals includes N×M pixels. The upper left coordinates of the image indicated by the image signals are indicated by (0, 0). The rightward direction corresponds to the positive X-axis direction, and the downward direction corresponds to the positive Y-axis direction. The X-axis is an axis that is parallel to the horizontal scan line, and the Y-axis is an axis that is orthogonal to the X-axis, for example.

$$Yave(x, y) = \frac{\sum_{i=x-a}^{x-1} Y(i, y)}{a} \quad (2)$$

a in the expression (2) is a constant that is set corresponding to the width N of the image indicated by the image signals. For example, the constant a is set to be 3% of the width N of the image indicated by the image signals.

Figure 8A:
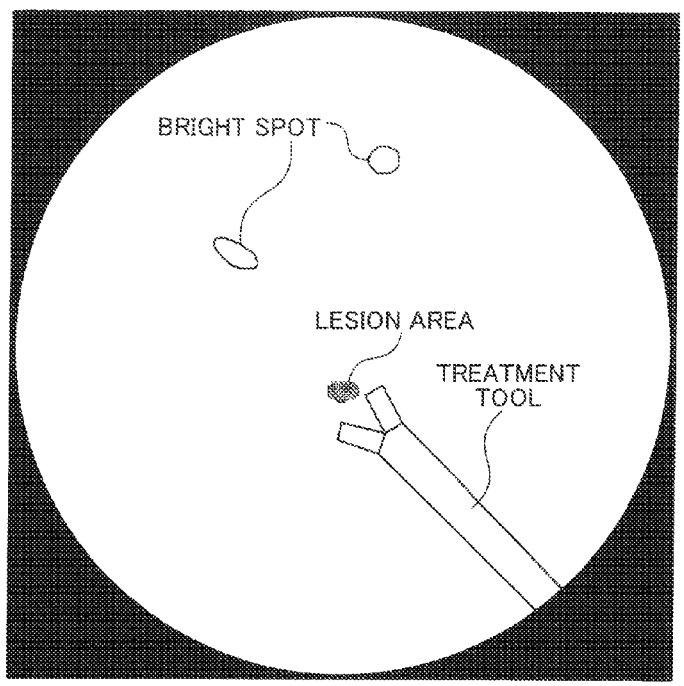
FIGS. 8A and 8B are views illustrating a process performed by an attention area setting section.
Figure 8B:
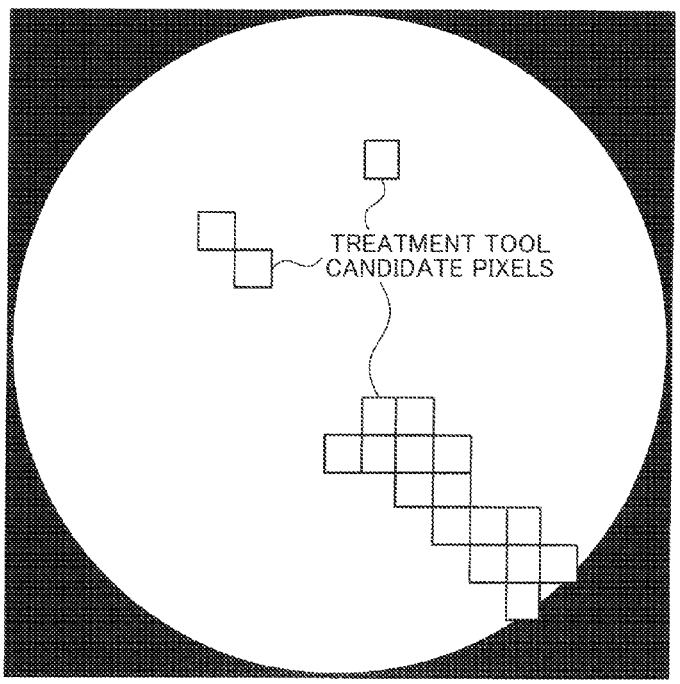

Next, whether or not the luminance signal value of the attention pixel is sufficiently larger than the average luminance Yave(x, y) is determined using the following expression (3).

$$Y(x,y) > Yave(x,y) + Yp \quad (3)$$

where, Yp is a value that is set in advance as a parameter. A pixel that satisfies the expression (3) is determined to be a treatment tool candidate pixel. For example, when the image signals include images of the treatment tool and bright spots (see FIG. 8A), the treatment tool candidate pixels are detected as illustrated in FIG. 8B.

Figure 9:
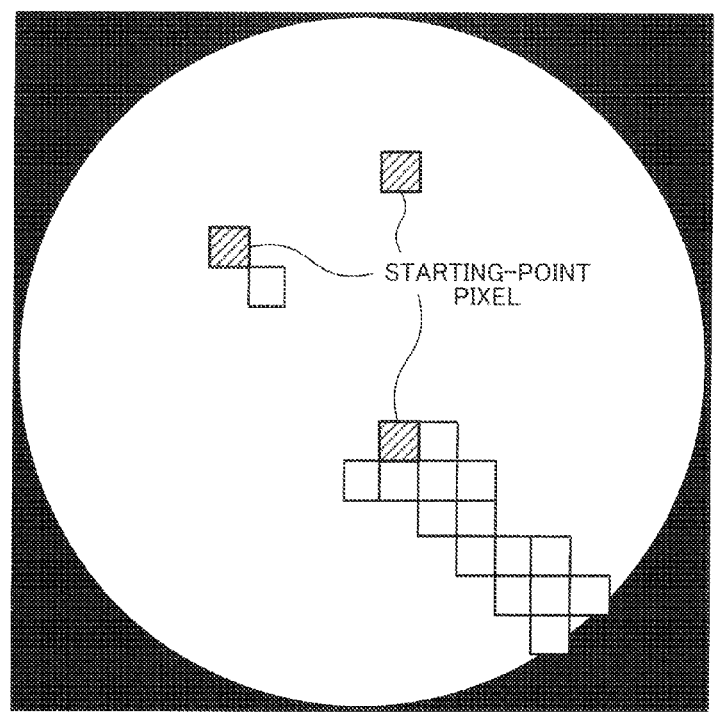
FIG. 9 is a view illustrating a process performed by an attention area setting section.

An area that includes a plurality of adjacent treatment tool candidate pixels is extracted as a treatment tool candidate area. Specifically, the image signals are searched for from the upper left, and the attention pixel (x, y) that corresponds to the treatment tool candidate pixel is set to be a starting-point pixel when the left pixel (x−1,y), the upper left pixel (x−1, y−1), the upper pixel (x, y−1), and the upper right pixel (x+1, y−1)) with respect to the attention pixel are not the treatment tool candidate pixel. As illustrated in FIG. 9, the hatched pixels are set to be the starting-point pixels.

Figure 10:
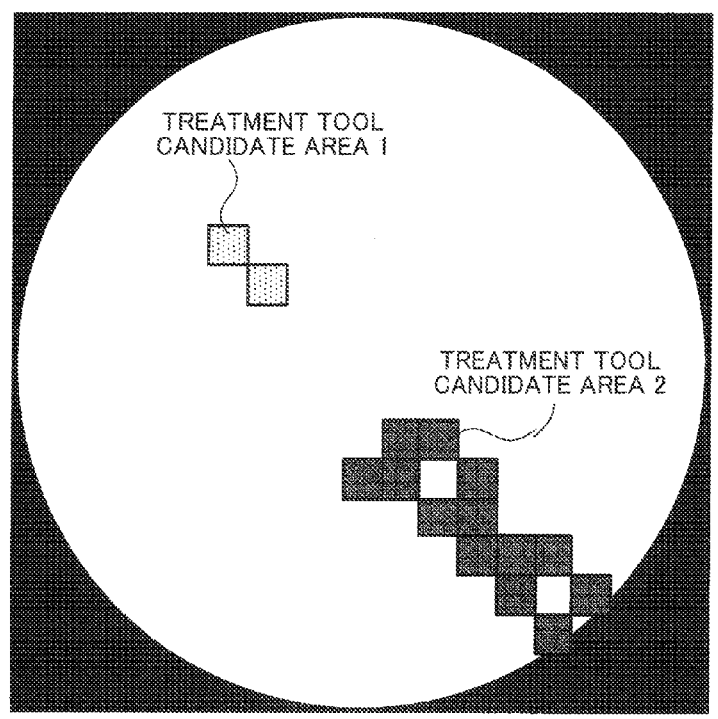
FIG. 10 is a view illustrating a process performed by an attention area setting section.

The treatment tool candidate pixel is then searched counterclockwise from the lower left pixel (x−1, y−1) with respect to the starting-point pixel (x, y). When no treatment tool candidate pixel has been detected around the starting-point pixel, the treatment tool candidate pixel is searched around the next starting-point pixel. When the treatment tool candidate pixel has been detected around the starting-point pixel, the treatment tool candidate pixel is searched counterclockwise around the detected treatment tool candidate pixel. The treatment tool candidate pixel is searched until the starting-point pixel is detected to be the treatment tool candidate pixel. The search process is terminated when the Y-coordinate value of the treatment tool candidate pixel is smaller than that of the starting-point pixel, and the treatment tool candidate pixel is searched around the next starting-point pixel. As illustrated in FIG. 10, an area enclosed by the detected treatment tool candidate pixels is set to be a treatment tool candidate area after completion of the treatment tool candidate pixel detection process. In FIG. 10, the hatched pixels have been detected to be the treatment tool candidate pixels by the search process.

The pixel count of each area extracted as the treatment tool candidate area is determined, and an area having the largest pixel count is extracted. When the pixel count $T_{max}$ of the area having the largest pixel count is larger than a threshold value $TH_t$ set in advance ($T_{max} > TH_t$), the area having the largest pixel count is determined to be the treatment tool area. When the pixel count $T_{max}$ of the area having the largest pixel count is equal to or smaller than the threshold value $TH_t$, it is determined that the image signals do not include an image of the treatment tool, and the treatment tool area is not set to the image signals. As illustrated in FIG. 10, when the treatment tool candidate area 2 has the largest pixel count, whether or not the number of the treatment tool candidate pixels included in the treatment tool candidate area 2 is larger than the threshold value set in advance is determined. When the number of the treatment tool candidate pixels included in the treatment tool candidate area 2 is larger than the threshold value, the treatment tool candidate area 2 is set to be the treatment tool area.

Figure 11:
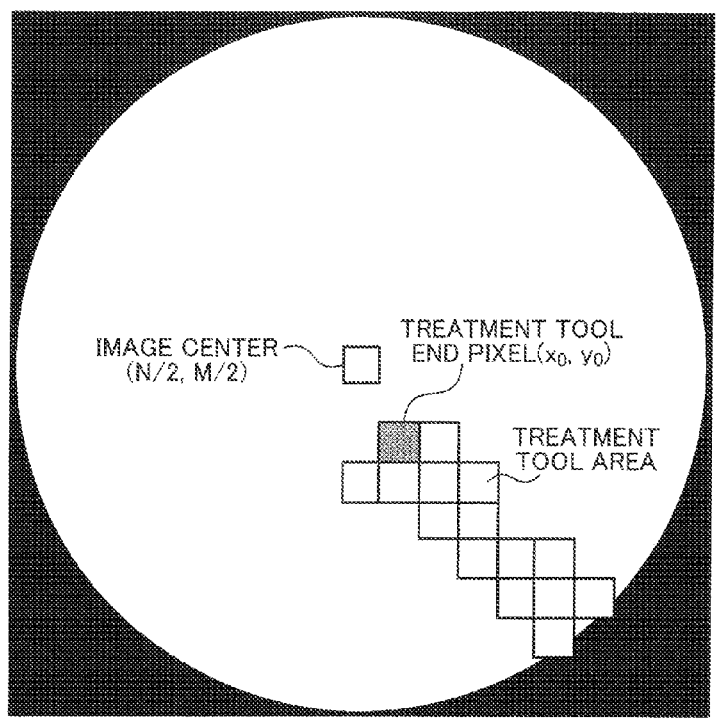
FIG. 11 is a view illustrating a process performed by an attention area setting section.

An area that corresponds to the end of the treatment tool is then extracted from the treatment tool area, and set to be a treatment tool end pixel. As illustrated in FIG. 11, a pixel among the pixels included in the treatment tool area that is closest to the center of the image is extracted as the treatment tool end pixel. In FIG. 11, the coordinates of the center of the image are indicated by (N/2, M/2), and the coordinates of the treatment tool end pixel are indicated by ($x_0$, $y_0$). Note that the treatment tool end pixel may be extracted by selecting a plurality of pixels close to the coordinates (N/2, M/2) of the center of the image from the pixels included in the treatment tool area, and determining the center of gravity of the selected pixels to be the treatment tool end pixel.

As illustrated in FIG. 12, the pixels that are positioned inside a circle that is formed around the treatment tool end pixel ($x_0$, $y_0$) and has a radius R is set to be the attention area. Note that the radius R is a constant that is set corresponding to the width N of the image indicated by the image signals. For example, the radius R is set to be 10% of the width N of the image indicated by the image signals. Whether or not the pixel at the coordinates (x, y) is positioned inside the circle having the radius R is determined using the following expression (4).

$$R^2 > (x-x_0)^2 + (y-y_0)^2 \quad (4)$$

The attention area setting section 413 transmits the set attention area and the center pixel ($x_0$, $y_0$) to the scaling section 414.

Although an example in which the radius R is a constant has been described above, the configuration according to the first embodiment is not limited thereto. For example, the radius R may be a variable that changes corresponding to the distance L between the center ($x_0$, $y_0$) of the attention area and the center (N/2, M/2) of the image. The distance L between the center ($x_0$, $y_0$) of the attention area and the center (N/2, M/2) of the image is calculated by the following expression (5).

$$L = \sqrt{\left(\frac{N}{2} - x_0\right)^2 + \left(\frac{M}{2} - y_0\right)^2} \quad (5)$$

Although an example in which the attention area is a circular area formed around the coordinates ($x_0$, $y_0$) has been described above, the configuration according to the first embodiment is not limited thereto. For example, the attention area may be a rectangular or elliptical area formed around the coordinates ($x_0$, $y_0$).

2.4. Scaling Section

The process performed by the scaling section 414 is described in detail below. The scaling section 414 performs the scaling process locally on the image signals based on the attention area set by the attention area setting section 413 and the center pixel ($x_0$, $y_0$). Note that the scaling section 414 does not perform the scaling process when the attention area has not been set by the attention area setting section 413, the input image signals then being output directly to the post-processing section 415.

Figure 13:
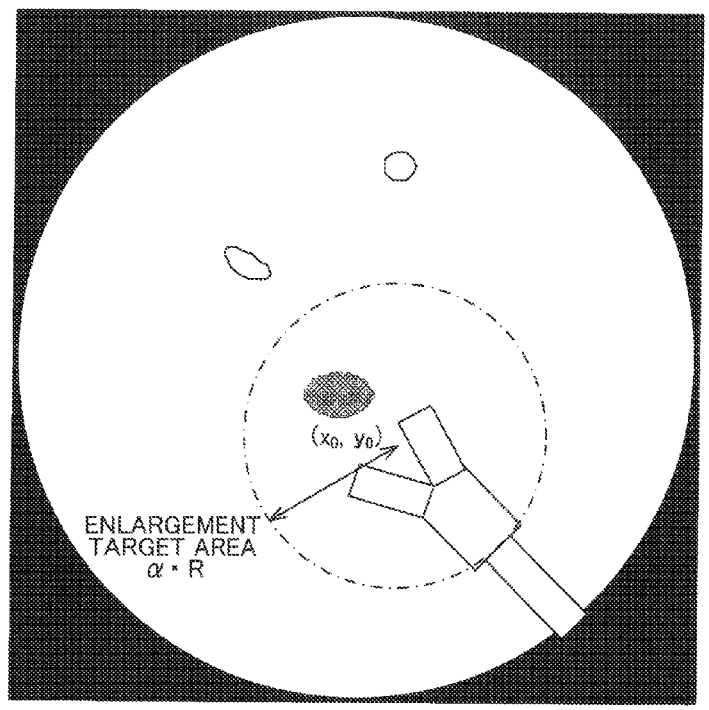
FIG. 13 is a view illustrating a process performed by a scaling section.

As illustrated in FIG. 13, the scaling section 414 enlarges the attention area by an enlargement factor α (scaling factor in a broad sense), and superimposes the enlarged image on the original image. Specifically, the scaling section 414 enlarges the attention area by the enlargement factor α in the radial direction around the center of the circle, and superimposes the enlarged image on the original image so that the center of the enlarged circular area coincides with the center pixel $(x_0, y_0)$ of the original attention area. The enlarged attention area may be hereinafter referred to as "enlargement target area". The coordinates (x', y') obtained by a coordinate transformation process on the pixel at the coordinates (x, y) by a factor of a are calculated by the following expression (6).

$$x'=\alpha(x-x_0)+x_0$$

$$y'=\alpha(y-y_0)+y_0 \qquad (6)$$

Figure 14:
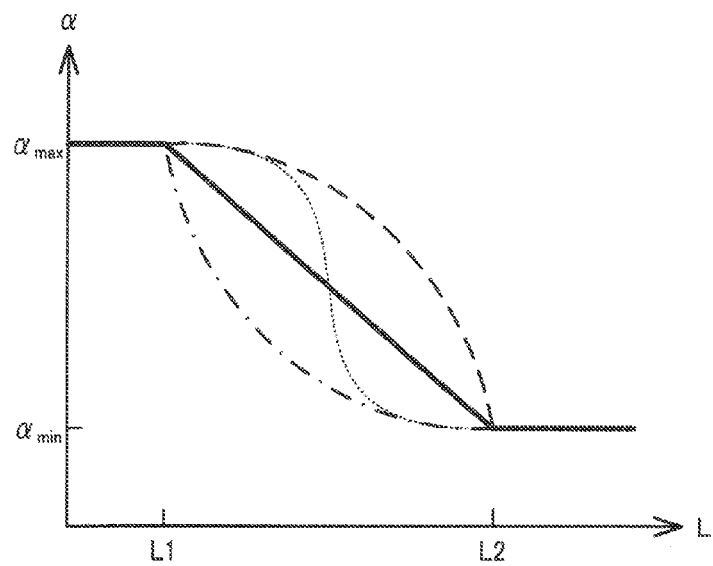
FIG. 14 is a view illustrating a process performed by a scaling section.

Note that α is a constant that is larger than 1 and set in advance. For example, α is set to 1.5. The enlargement factor α is not limited to a fixed constant. The operator may input an arbitrary value as the enlargement factor α. The enlargement factor α may be a variable that changes corresponding to the distance L between the center $(x_0, y_0)$ of the attention area and the center (N/2, M/2) of the image (see FIG. 14).

Figure 15:
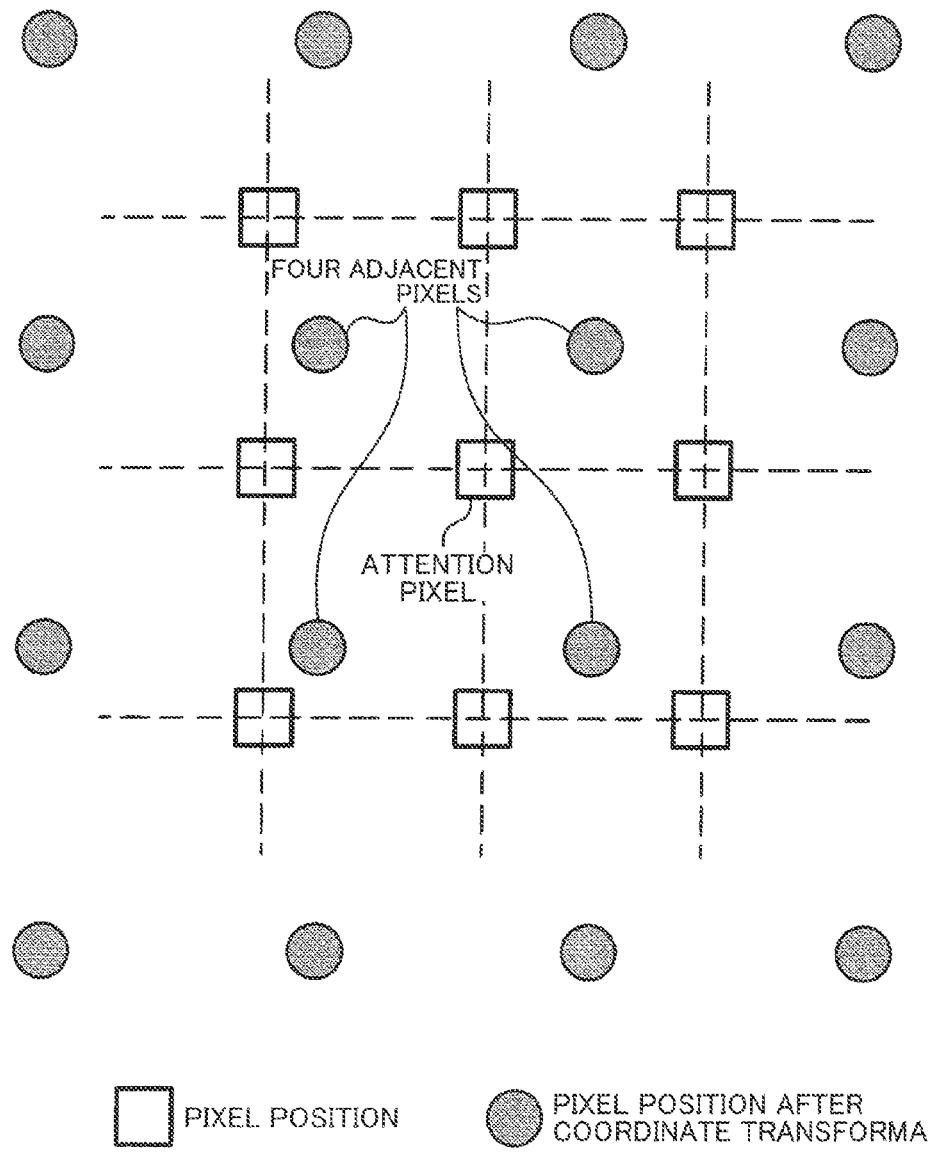
FIG. 15 is a view illustrating a process performed by a scaling section.

The scaling section 414 generates an interpolation pixel at a pixel position within the enlargement target area during the enlargement process. Specifically, the scaling section 414 performs a linear interpolation process on a pixel position within the enlargement target area using four adjacent pixels after the coordinate transformation process using the expression (6) (see FIG. 15). Note that the interpolation process is not limited to the linear interpolation process. For example, an interpolation method such as a nearest neighbor interpolation method or a bicubic convolution interpolation method may be used.

Figure 16:
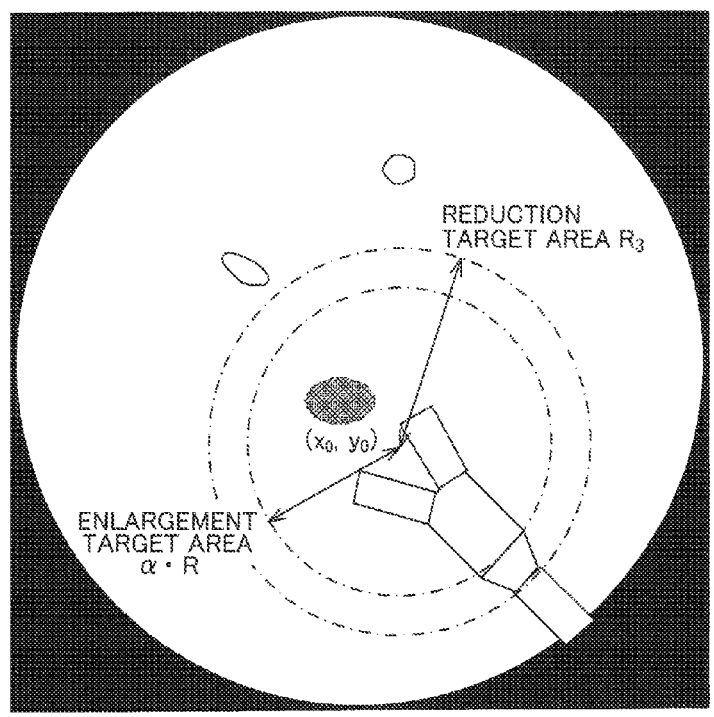
FIG. 16 is a view illustrating a modification of a scaling process.
Figure 17:
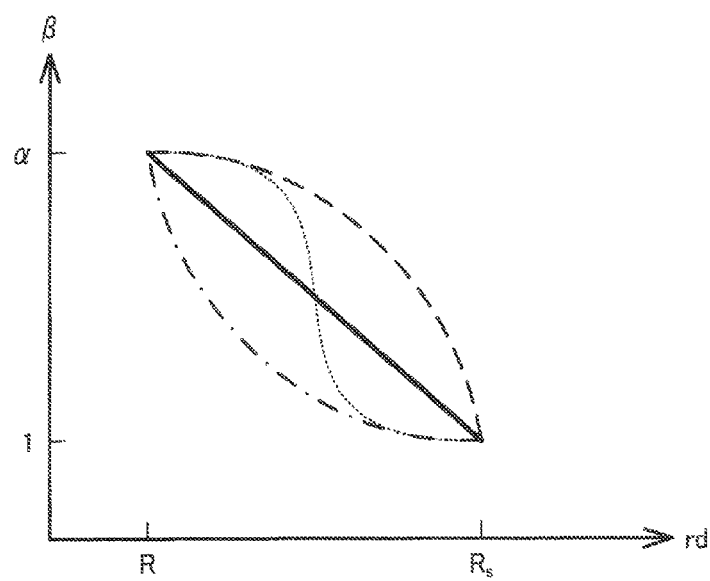
FIG. 17 is a view illustrating a modification of a scaling process.

FIG. 16 illustrates a modification of the scaling process. As illustrated in FIG. 16, a reduction target area may be provided outside the enlargement target area. Specifically, the reduction target area is an area that is positioned inside a circle that is formed around the coordinates $(x_0, y_0)$ and has a radius $R_s$, and is positioned outside the enlargement target area. The scaling section 414 reduces the area positioned between the circle having the radius R and the circle having the radius $R_s$ by a reduction factor β (scaling factor in a broad sense). The reduction factor β is a variable that changes corresponding to the distance rd between the processing target pixel (x, y) and the center coordinates $(x_0, y_0)$. The distance rd is calculated by the following expression (7). As illustrated in FIG. 17, the reduction factor β is a coefficient that decreases as the distance rd increases. β=α when the distance rd is R, and β=1 when the distance rd is $R_s$.

$$rd=\sqrt{(x-x_0)^2+(y-y_0)^2} \qquad (7)$$

The scaling section 414 generates an interpolation pixel at a pixel position within the reduction target area during the reduction process. Specifically, the scaling section 414 performs a linear interpolation process on a pixel position within the reduction target area using a pixel that has been reduced by the reduction factor β. Note that the interpolation process is not limited to the linear interpolation process. For example, an interpolation method such as a nearest neighbor interpolation method or a bicubic convolution interpolation method may be used.

According to the above modification, since the continuity of the image is maintained at the boundary of the enlargement target area by providing the reduction target area outside the enlargement target area, it is possible to obtain appropriate image signals subjected to the scaling process.

Although an example in which the reduction target area is formed by pixels that are positioned inside the circle having the radius $R_s$ has been described above, the configuration according to the first embodiment is not limited thereto. For example, the entire area positioned outside the enlargement target area may be set to be the reduction target area. In this case, the reduction factor β decreases as the distance from the edge of the image decreases, and is set to 1 at the edge of the image.

2.5. Software

In the first embodiment, some or all of the processes performed by each section of the image processing section 410 may be implemented by software. In this case, a CPU of a computer system (described later with reference to FIG. 72, for example) executes an image processing program.

Figure 18:
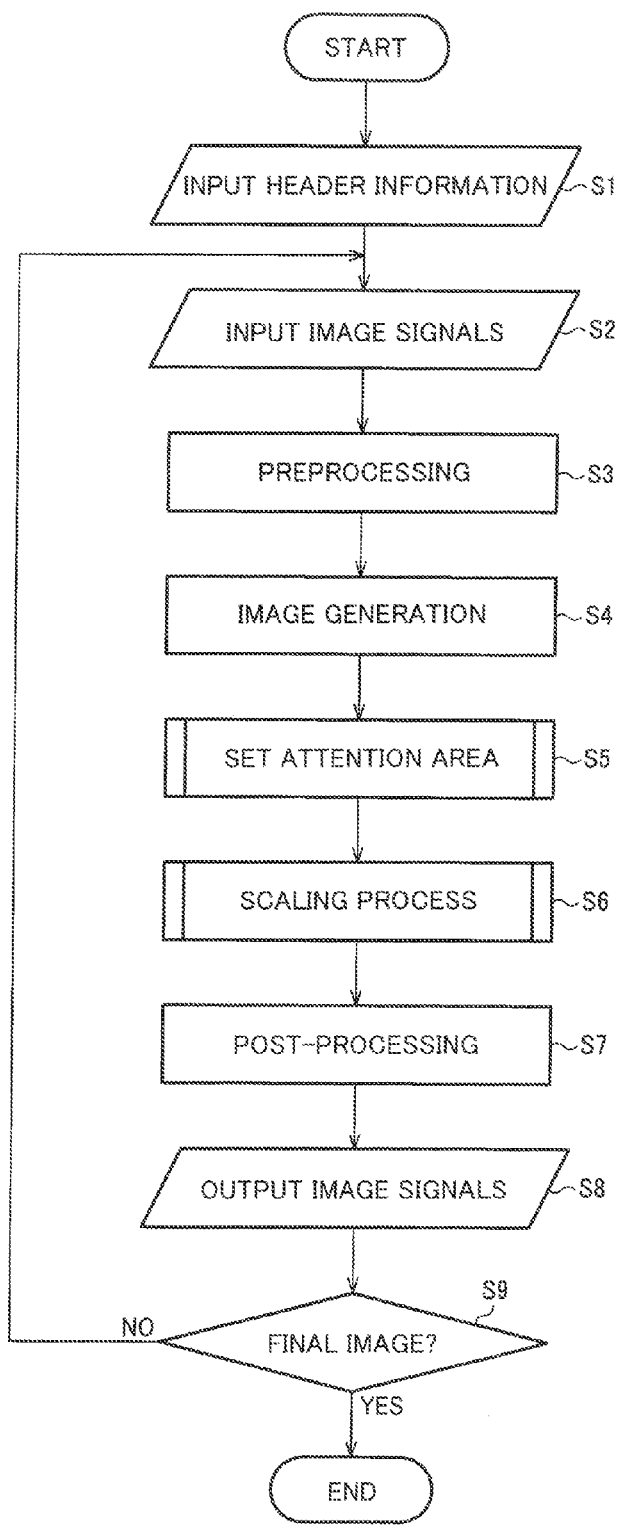
FIG. 18 illustrates an example of a flowchart of an image processing program.

FIG. 18 illustrates an example of a flowchart of the image processing program. As illustrated in FIG. 18, header information (e.g., light source synchronization signal and imaging mode) is input to the time-series images (S1).

The images are input to an image buffer allocated in advance (S2). The OB clamp process, the gain control process, the WB correction process, and the like are performed on the input images (S3). The image generation process is performed on the input time-series images according to the light source synchronization signal (S4).

The attention area setting process is performed on the image (S5). The attention area setting process is described in detail below with reference to FIG. 19. The scaling process is performed on the image signals based on the attention area (S6). The scaling process is described in detail below with reference to FIG. 20. The grayscale transformation process, the color process, the contour enhancement process, and the like are performed on the image subjected to the scaling process (S7). The image subjected to post-processing is output (S8).

Whether or not the final image among the time-series images has been processed is then determined (S9). When it has been determined that the final image has not been processed, the process in the steps S2 to S8 is performed on the subsequent image (S9, No). When it has been determined that each image has been processed, the process is terminated (S9, Yes).

Figure 19:
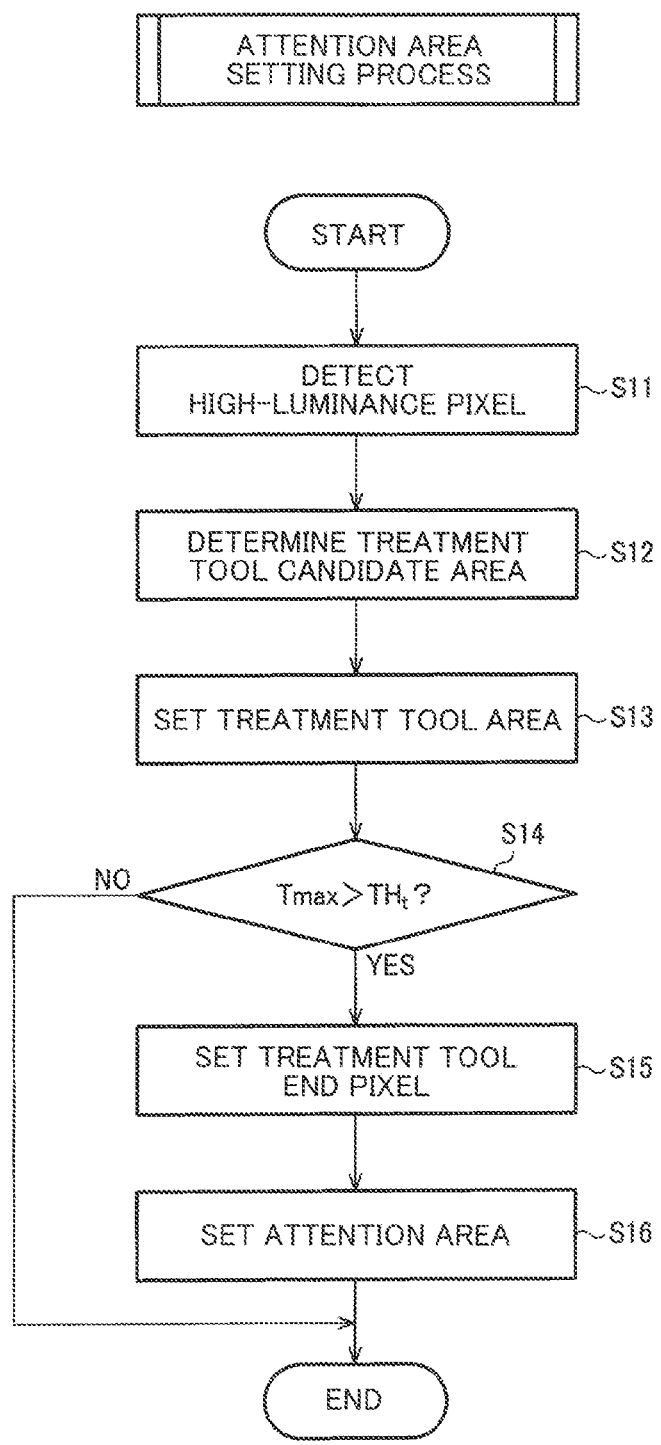
FIG. 19 illustrates an example of a detailed flowchart of an attention area setting process.

FIG. 19 illustrates an example of a detailed flowchart of the attention area setting process (S5). As illustrated in FIG. 19, a high-luminance pixel is detected from the input image signals as the treatment tool candidate pixel (S11).

An area that includes a plurality of adjacent treatment tool candidate pixels is extracted as the treatment tool candidate area (S12). The treatment tool candidate area that has the largest pixel count is detected to be the treatment tool area (S13). Whether or not the pixel count $T_{max}$ of the treatment tool area is larger than the threshold value $TH_t$ set in advance is determined (S14). When it has been determined that the pixel count $T_{max}$ is larger than the threshold value $TH_t$, a step S15 is performed (S14, Yes). When it has been determined that the pixel count $T_{max}$ is equal to or smaller than the threshold value $TH_t$, the process is terminated (S14, No).

A pixel among the pixels included in the treatment tool area that is closest to the center of the image signals is extracted as the treatment tool end pixel (S15). The pixels that are positioned inside a circle that is formed around the treatment tool end pixel and has a radius R are set to be the attention area (S16), and the process is terminated.

Figure 20:
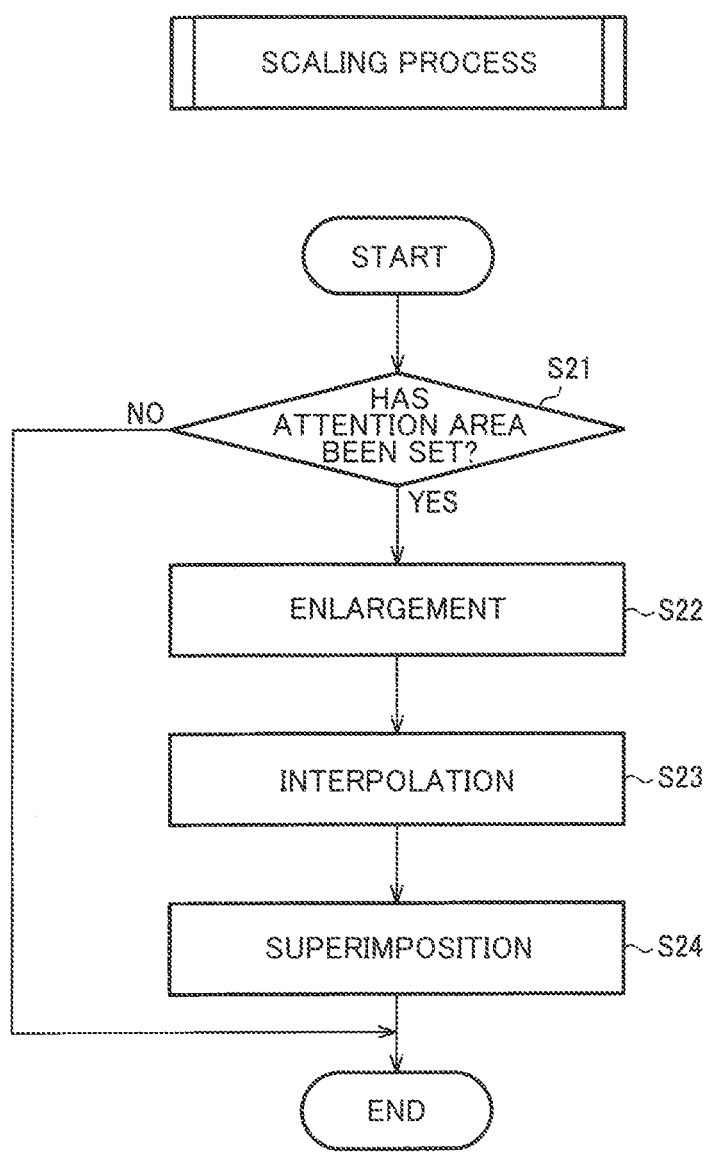
FIG. 20 illustrates an example of a detailed flowchart of a scaling process.

FIG. 20 illustrates an example of a detailed flowchart of the scaling process (S6). As illustrated in FIG. 20, whether or not the attention area has been set by the attention area setting process is determined (S21). When it has been determined that the attention area has been set by the attention area setting process (S21, Yes), a step S22 is performed. When it has been determined that the attention area has not been set by the attention area setting process (S21, No), the process is terminated.

The coordinate transformation process is performed on the pixels included in a circle that is formed around the center of the attention pixel and has the radius R using the enlargement factor α (S22). The area subjected to the coordinate transformation process using the enlargement factor α may be hereinafter referred to as "enlargement target area". An interpolation pixel is generated at a pixel position within the enlargement target area (S23). The enlargement target area is superimposed on the image signals so that the center of the enlargement target area coincides with the center of the attention pixel (S24), and the process is terminated.

This makes it possible to store image data, and process the stored image data by means of software using a computer system (e.g., PC) (e.g., capsule endoscope).

According to the first embodiment, the endoscope system includes an image acquisition section (e.g., A/D conversion section 305), the attention area setting section 413, and the scaling section 414 (see FIG. 6). The image acquisition section acquires a captured image that includes an object image. The attention area setting section 413 sets the attention area within the captured image based on information from the endoscope system. The scaling section 414 performs a local scaling process that relatively enlarges the attention area as compared with another area.

According to the above configuration, since the attention area can be relatively enlarged as compared with another area, it is possible to obtain more detailed information about a small lesion area, and perform appropriate diagnosis and procedures on the attention area.

Note that the information from the endoscope system refers to information acquired by each section of the endoscope system. For example, the information from the endoscope system refers to a captured image captured by an imaging section, a signal obtained by processing the captured image, a control signal that controls each section, and a sensing signal generated by a sensor provided in the endoscope system.

The term "attention area" used herein refers to an area for which the observation priority for the user is relatively high as compared with another area. For example, when the user is a doctor, and desires to perform treatment, the attention area refers to an area that includes a mucosal area or a lesion area. If the doctor desires to observe bubbles or feces, the attention area refers to an area that includes a bubble area or a feces area. Specifically, the attention area for the user differs depending on the objective of observation, but necessarily has a relatively high observation priority as compared with another area.

The scaling section 414 may perform the local scaling process while maintaining the angle of view of the captured image (see FIG. 13 and the like).

The above configuration makes it possible for the operator to closely observe the attention area while observing the entire object image. Since the entire object image and the attention area can be displayed within a single image, the burden imposed on the operator can be reduced as compared with the case where the operator must observe a plurality of images. Moreover, since it is unnecessary to switch the image between the wide-angle image and the enlarged image, the operator need not perform a troublesome operation.

The expression "maintaining the angle of view" used herein means that the range of the object displayed within the image does not change due to the scaling process. Note that the angle of view need not be maintained strictly, but may be maintained substantially.

The attention area setting section 413 may set the attention area using the captured image as the information from the endoscope system.

Specifically, the attention area setting section 413 may include a treatment tool detection section (not illustrated in the drawings). The treatment tool detection section may detect a treatment tool area based on the captured image, a treatment tool that is used to perform procedures on the object being captured within the treatment tool area (see FIG. 13 and the like). The attention area setting section 413 may set the attention area based on the detected treatment tool area.

It is considered that an area that attracts the operator's attention is positioned within the image when the treatment tool is displayed within the image. The above configuration makes it possible to enlarge the attention area using the scaling process. This makes it possible to display a lesion area (procedure target) to have an appropriate size, and obtain an image suitable for the operator to perform procedures.

The treatment tool detection section may detect the end of the treatment tool area. The attention area setting section 413 may set an area inside a circle that is formed around the detected end and has a given radius to be the attention area.

Specifically, the treatment tool detection section may set a pixel among the pixels included in the treatment tool area that is closest to the center (N/2, M/2) of the captured image to be the end of the treatment tool area (treatment tool end pixel $(x_0, y_0)$) (see FIG. 11).

The above configuration makes it possible to set the procedure target area that is considered to be present around the end of the treatment tool to be the attention area, and enlarge the attention area using the scaling process.

Note that the circle (circular area) set to be the attention area is not limited to a true circle. For example, the circle (circular area) set to be the attention area may be an ellipse or the like.

The treatment tool detection section may include a luminance feature quantity calculation section (not illustrated in the drawings). The luminance feature quantity calculation section may calculate a luminance feature quantity (e.g., luminance signal value $Y(x, y)$) relating to the luminance of each pixel of the captured image. The treatment tool detection section may detect the treatment tool area based on the calculated luminance feature quantity.

Specifically, the treatment tool detection section may detect the treatment tool candidate pixel (i.e., a candidate for the treatment tool area) based on the luminance feature quantity, and may determine the treatment tool area based on the detected treatment tool candidate pixel (see FIG. 8B and the like).

More specifically, the treatment tool detection section may include a comparison section (not illustrated in the drawings). The comparison section may compare the luminance feature quantity (luminance signal value $Y(x, y)$) of the processing target pixel with the average luminance feature quantity (average value Yave (x, y)) of the pixels positioned around the processing target pixel (see FIG. 7 and the like). The treatment tool detection section may set a pixel of which the luminance feature quantity is larger than the average luminance feature quantity, to be the treatment tool candidate pixel.

Since the treatment tool is formed of a metal or the like, and has a high illumination light reflectance, the treatment tool is captured as a high-luminance image as compared with another object. Therefore, the treatment tool can be detected from the image by setting the treatment tool candidate pixel based on the luminance feature quantity.

The treatment tool detection section may classify the treatment tool candidate pixel into one or more treatment tool candidate areas (e.g., treatment tool candidate areas 1 and 2) based on position information about the treatment tool candidate pixel (see FIG. 10 and the like). The treatment tool detection section may select the treatment tool area from one or more treatment tool candidate areas.

Specifically, the treatment tool detection section may set one or more treatment tool candidate areas by extracting pixels that serve as the boundary between the treatment tool candidate area and another area from the treatment tool candidate pixels, and setting the treatment tool candidate pixels enclosed by the boundary to be the treatment tool candidate area.

The treatment tool detection section may determine the treatment tool area based on the number of treatment tool candidate pixels included in each treatment tool candidate area.

Specifically, the treatment tool detection section may determine an area (e.g., treatment tool candidate area 2) among one or more treatment tool candidate areas that includes the largest number of treatment tool candidate pixels, and includes treatment tool candidate pixels in a number larger than a given threshold value ($TH_t$), to be the treatment tool area.

The above configuration makes it possible to select an area in which the treatment tool is captured, from a plurality of treatment tool candidate areas, even when a plurality of treatment tool candidate areas are detected due to a high-luminance area (e.g., bright spot) that occurs when the illumination light is reflected by a mucous membrane.

The image acquisition section may acquire the captured image in which the front field of view and the side field of view of the end of the scope (insertion section 300) are captured (see FIGS. 1 and 3 and the like).

Specifically, the captured image may be an image obtained by the objective optical system that forms an image of the front field of view and the side field of view. The objective optical system may have an angle of view of more than 180° (e.g., 230°).

Figure 2C:
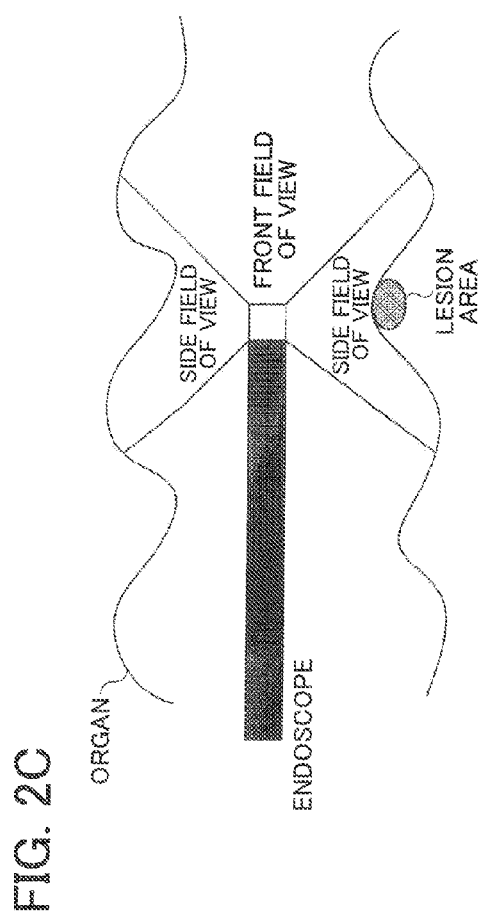

The above configuration makes it possible to simultaneously observe the object positioned on the front side of the scope and the object positioned on the side of the scope (see FIG. 2C and the like). This makes it possible to prevent a situation in which a lesion area positioned on the wall surface of a hollow tubular organ is missed.

Note that the objective optical system is not limited to an objective lens. The objective optical system may be a catoptric system, or may be an optical system formed by combining a lens and a catoptric system (see FIG. 1). The objective optical system is not limited to the objective optical system illustrated in FIG. 1. The objective optical system may utilize a fish-eye lens having an angle of view of more than 180°.

The front field of view (front field-of-view range) refers to a field-of-view range that includes the optical axis direction of the objective optical system. For example, the front field of view refers to a range of 0 to 45° with respect to the optical axis. The side field of view (side field-of-view range) refers to a field-of-view range that includes a direction orthogonal to the optical axis of the objective optical system. For example, the side field of view refers to a range of 45 to 135° with respect to the optical axis. The objective optical system 303 according to the first embodiment has a field-of-view range of 0 to 115° with respect to the optical axis, for example.

3. Second Embodiment

A second embodiment in which insertion of the treatment tool is sensed to set the attention area is described below.

Figure 21:
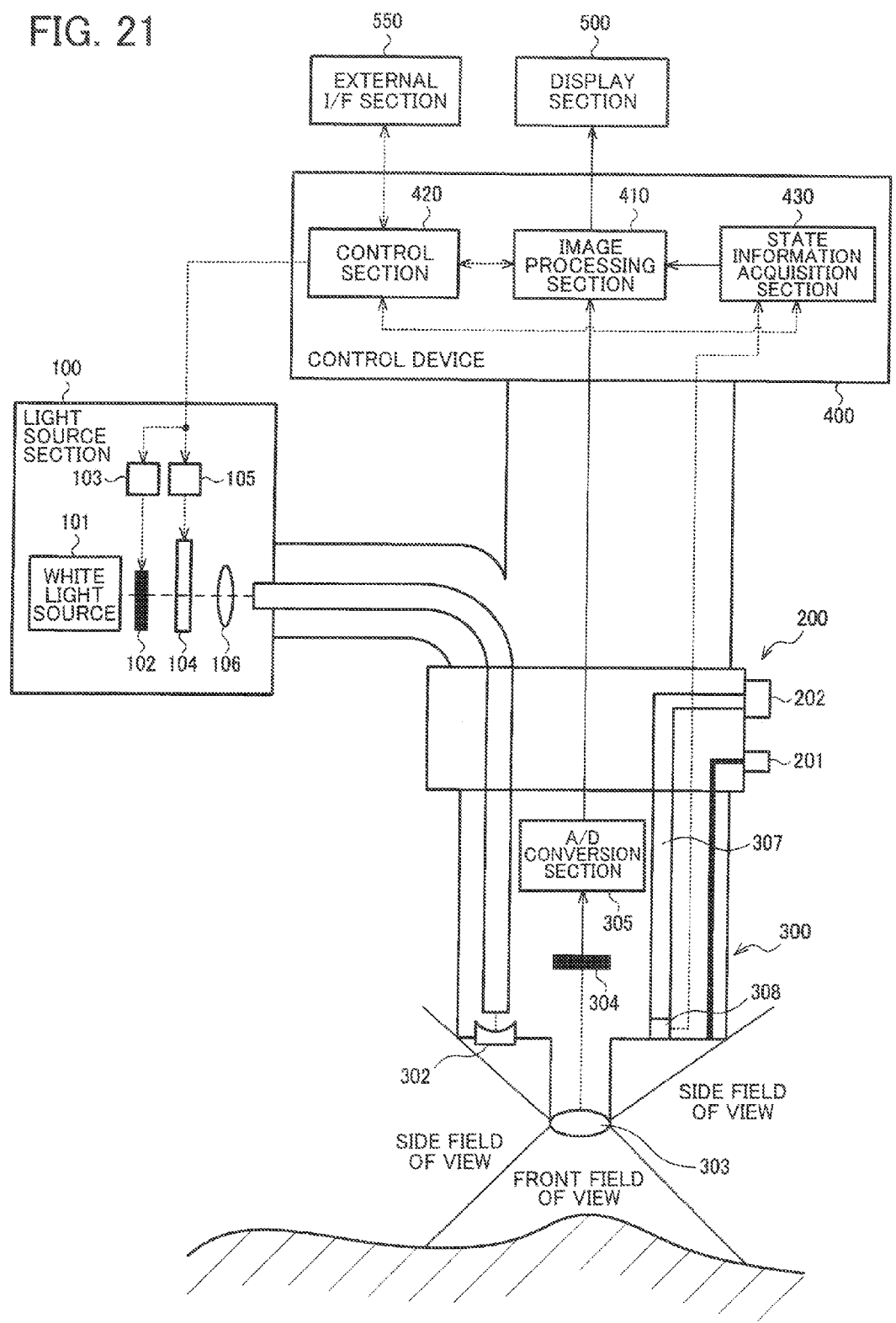
FIG. 21 illustrates a configuration example of an endoscope system according to a second embodiment.

FIG. 21 illustrates a configuration example of an endoscope system according to the second embodiment. The endoscope system includes a light source section 100, an operation section 200, an insertion section 300, a control device 400, a display section 500, and an external I/F section 550. Note that the same elements as those described above with reference to FIG. 3 and the like are indicated by identical reference signs, and description of these elements is appropriately omitted.

The insertion section 300 includes a treatment tool sensor 308. The treatment tool sensor 308 is provided in the insertion channel 307. The treatment tool sensor 308 detects the treatment tool that is inserted through the insertion channel 307 and protrudes forward from the insertion section 300. The treatment tool sensor 308 is connected to a state information acquisition section 430 (described later).

The control device 400 includes the state information acquisition section 430. The state information acquisition section 430 is connected to the image processing section 410. The control section 420 is bidirectionally connected to the state information acquisition section 430.

When the treatment tool sensor 308 has detected that the treatment tool has protruded from the end of the insertion section 300, the state information acquisition section 430 transmits a control signal that indicates that the image signals include the treatment tool to the image processing section 410.

Figure 22:
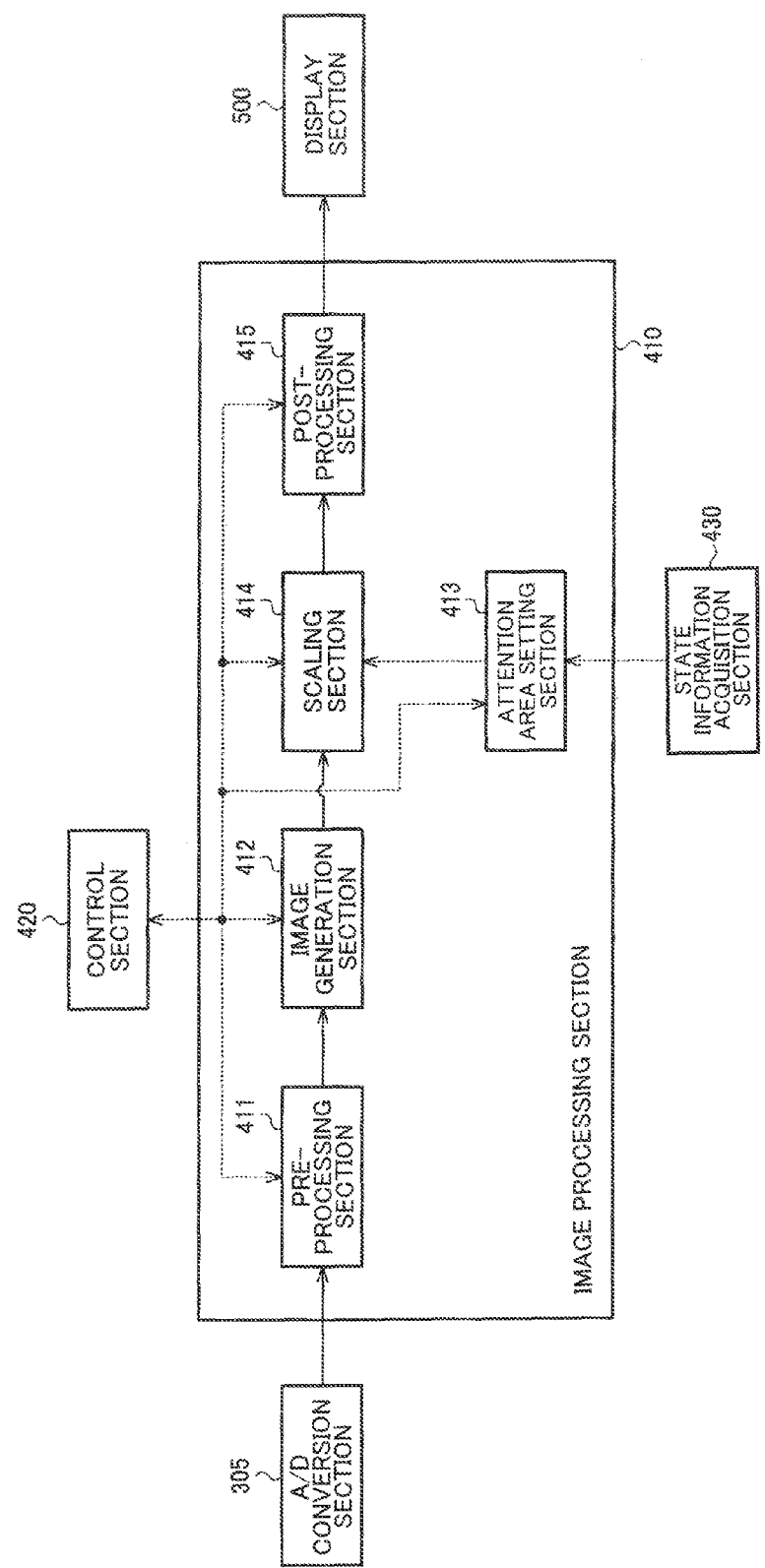
FIG. 22 illustrates a detailed configuration example of an image processing section according to the second embodiment.

FIG. 22 illustrates a detailed configuration example of the image processing section 410 according to the second embodiment. The state information acquisition section 430 is connected to the attention area setting section 413. The attention area setting section 413 is connected to the scaling section 414.

The process performed by the attention area setting section 413 according to the second embodiment differs from the process performed by the attention area setting section 413 according to the first embodiment. Specifically, when the attention area setting section 413 has received the control signal (that indicates that the image signals include the treatment tool) from the state information acquisition section 430, the attention area setting section 413 sets the attention area within the image indicated by the image signals. For example, the attention area setting section 413 sets an area positioned inside a circle that is formed around the center (N/2, M/2) of the image (i.e., the center of the attention area) and has a radius R to be the attention area (see FIG. 23). The attention area setting section 413 transmits the set attention area and the center pixel ($x_0$, $y_0$) to the scaling section 414.

Note that the center of the attention area is not limited to the center (N/2, M/2) of the image. The center of the attention area may be set in advance based on the relative positional relationship between the image sensor and the insertion channel. For example, when the insertion channel is provided in the positive Y-axis direction with respect to the center of the image, the attention area may be set in the positive Y-axis direction with respect to the center of the image.

According to the second embodiment, the endoscope system includes the state information acquisition section 430 that acquires state information about the endoscope system (see FIG. 21). The attention area setting section 413 sets the attention area using the state information as the information from the endoscope system.

Specifically, the attention area setting section 413 detects whether or not the treatment tool that is used to perform procedures on the object has protruded from the end of the scope (based on the sensing signal generated by the treatment tool sensor 308), and acquires the detection result as the state information. The attention area setting section 413 sets the attention area based on the detection result.

Figure 23:
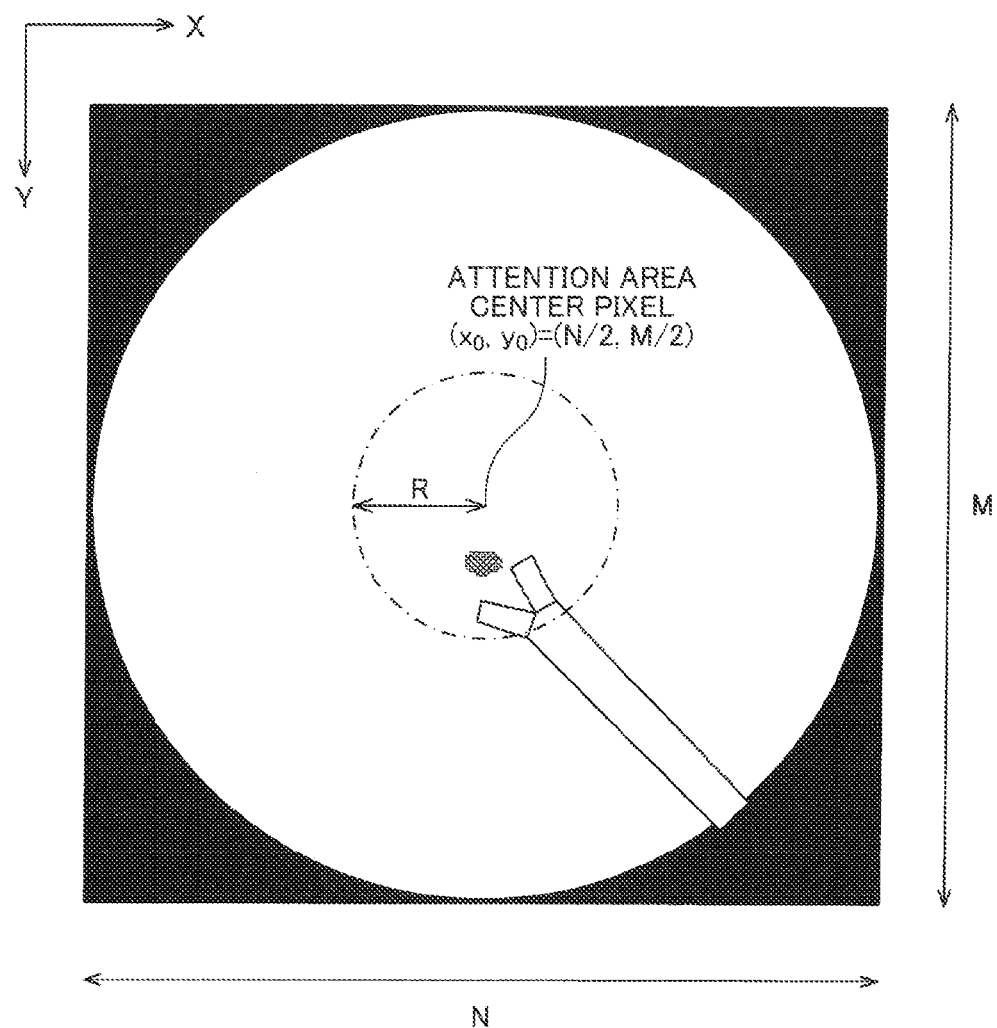
FIG. 23 is a view illustrating a process performed by an attention area setting section according to the second embodiment.

More specifically, when it has been detected that the treatment tool has protruded from the end of the scope, the attention area setting section 413 sets a center area of the captured image, or an area positioned on the treatment tool insertion side with respect to the center of the captured image (e.g., an area positioned in the positive Y-axis direction with respect to the center of the image) to be the attention area (see FIG. 23 and the like).

The above configuration makes it possible to set the attention area when the operator has operated the treatment tool, and enlarge the attention area using the scaling process. It is also possible to set the center or the lower part of the image (where it is considered that the operator normally positions the lesion area) to be the attention area, and enlarge the attention area. This makes it possible to display the lesion area (procedure target) to have an appropriate size irrespective of the image signals, and obtain an image appropriate for the operator to perform procedures.

Note that the state information about the endoscope system refers to information that indicates the state of each section of the endoscope system. For example, the state information refers to information (e.g., travel direction) about the scope obtained by processing the captured image, a control signal that controls the state of each section, and a sensing signal generated by a sensor that senses the state of each section.

4. Third Embodiment
4.1. Endoscope System

A third embodiment in which the attention area and the scaling factor are set based on the curve angle or the curve motion amount of the scope is described below.

Figure 24:
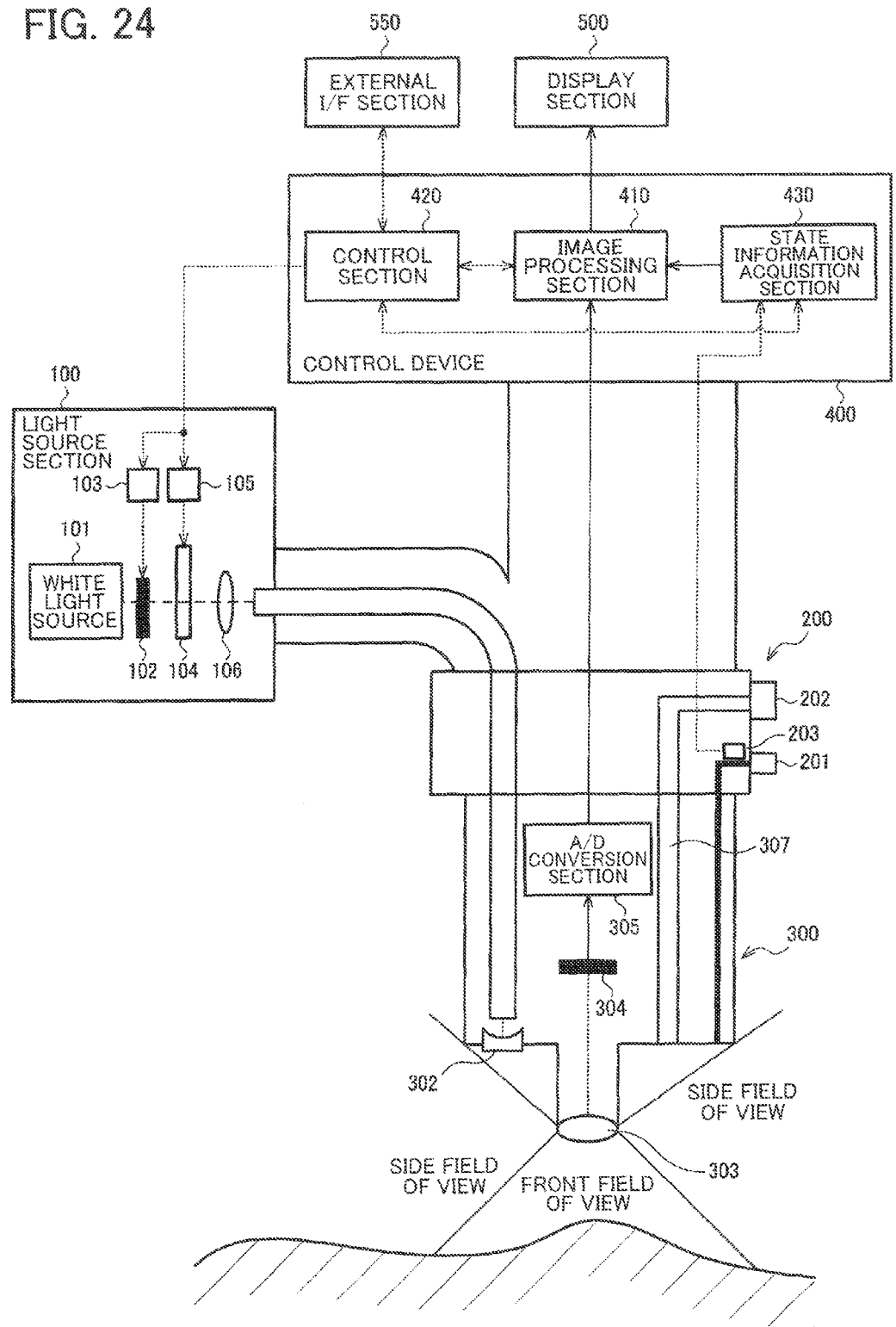
FIG. 24 illustrates a configuration example of an endoscope system according to a third embodiment.

FIG. 24 illustrates a configuration example of an endoscope system according to the third embodiment. The endoscope system includes a light source section 100, an operation section 200, an insertion section 300, a control device 400, a display section 500, and an external I/F section 550. Note that the same elements as those described above with reference to FIG. 3 and the like are indicated by identical reference signs, and description of these elements is appropriately omitted.

The operation section 200 includes a curve operation lever 201 that is used to curve the insertion section 300, an insertion opening 202 into which a treatment tool (e.g., forceps) is inserted, and an operation amount detection sensor 203 that detects operation information (e.g., curve angle and curve motion amount) about a curve operation performed on the end of the insertion section 300. The operation amount detection sensor 203 is connected to a state information acquisition section 430, and transmits the operation information about the curve operation to the state information acquisition section 430.

The control device 400 includes an image processing section 410, a control section 420, and a state information acquisition section 430. The image processing section 410 is configured in the same manner as in the configuration example illustrated in FIG. 22.

The state information acquisition section 430 acquires information about the operation performed on the endoscope using the operation section 200. The attention area setting section 413 sets the attention area based on the acquired information about the operation performed on the endoscope. The scaling section 414 sets the scaling factor, performs the enlargement process or the reduction process on the attention area set by the attention area setting section 413, and generates the image signals that are locally enlarged or reduced. The image signals processed by the scaling section 414 are transmitted to the display section 500.

4.2. Curve Angle Detection Section

Figure 25:
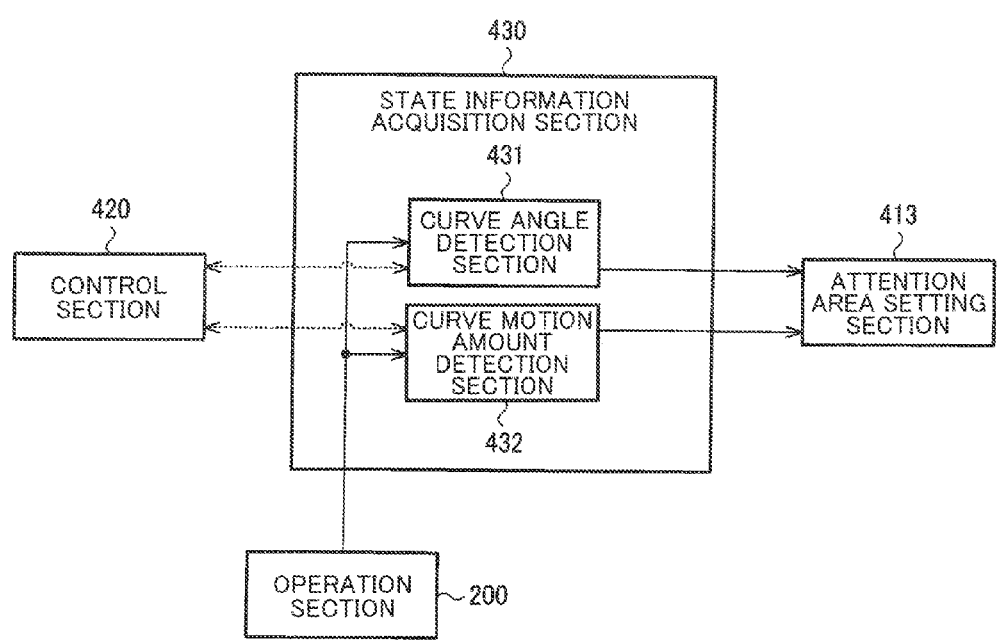
FIG. 25 illustrates a detailed configuration example of a state information acquisition section according to the third embodiment.

FIG. 25 illustrates a detailed configuration example of the state information acquisition section 430 according to the third embodiment. The state information acquisition section 430 includes at least one of a curve angle detection section 431 and a curve motion amount detection section 432.

The curve angle detection section 431 detects the current curve angle of the insertion section 300 that has been curved using the operation section 200. The curve motion amount detection section 432 detects the curve motion amount of the insertion section 300 that has been curved using the operation section 200. The curve motion amount refers to a change in the curve angle per unit time.

Specifically, the curve operation lever 201 is a dial-type lever. A curve operation wire 306 connected to the dial is pulled or pushed when the operator rotates the dial, and the end of the insertion section 300 is curved. The operation amount detection sensor 203 detects the pull/push length of the curve operation wire 306 as the operation amount. The state information acquisition section 430 calculates the curve angle from the detected operation amount. For example, the state information acquisition section 430 calculates the curve angle from the operation amount using a look-up table, a polynomial, or the like.

As illustrated in FIG. 26A, the curve angle $\theta$ is 0° when the operation amount of the wire 306 is 0. As illustrated in FIG. 26B, the curve angle $\theta$ is 45° when the wire 306 has been pulled by LW cm. As illustrated in FIG. 26C, the curve angle $\theta$ is −90° when the wire 306 has been pushed by 2 LW cm.

Note that it suffices that the curve angle information be obtained as information that indicates the curve angle, and the curve angle information may not be the curve angle. For example, the curve angle information may be the operation length of the wire 306. Specifically, since the operation amount of the operation lever 201 in the rotation direction and the pull/push length of the curve operation wire 306 have a one-to-one relationship, the curve angle can be calculated from the operation length of the wire 306.

The operation amount detected by the operation amount detection sensor 203 is not limited to length. For example, the operation amount detected by the operation amount detection sensor 203 may be the operation amount of the curve operation lever 201 in the rotation direction. In this case, the curve angle information may be the curve angle calculated from the operation amount of the curve operation lever 201 in the rotation direction, or may be the operation amount of the curve operation lever 201 in the rotation direction.

As described above with reference to FIG. 2C and the like, a lesion area that is positioned on the back side of folds can be found within the side field of view by performing a screening operation using a wide-angle endoscope. When the operator has found a lesion area, the operator curves the insertion section 300 by operating the curve operation lever 201 so that the lesion area can be observed within the front field of view (i.e., the lesion area can be easily observed within the front field of view as compared with the side field of view). When the lesion area is positioned within the side field of view, the operator desires to display the lesion area at a position close to the center of the front field of view by curving the insertion section to only a small extent.

According to the third embodiment, the peripheral area of the image is enlarged when the curve angle is large. Specifically, the attention area setting section 413 sets the area within the side field of view to be the attention area corresponding to the curve angle acquired by the curve angle detection section 431. For example, the attention area setting section 413 sets the area within the side field of view to be the attention area when the curve angle is equal to or more than a threshold value.

The scaling section 414 performs the enlargement process on the attention area within the captured image while increasing the enlargement factor as the curve angle increases. The scaling section 414 sets the reduction factor corresponding to the enlargement factor and the size of the image, and performs the reduction process on an area within the front field of view (i.e., an area other than the attention area).

4.3. Scaling Section

Figure 27A:
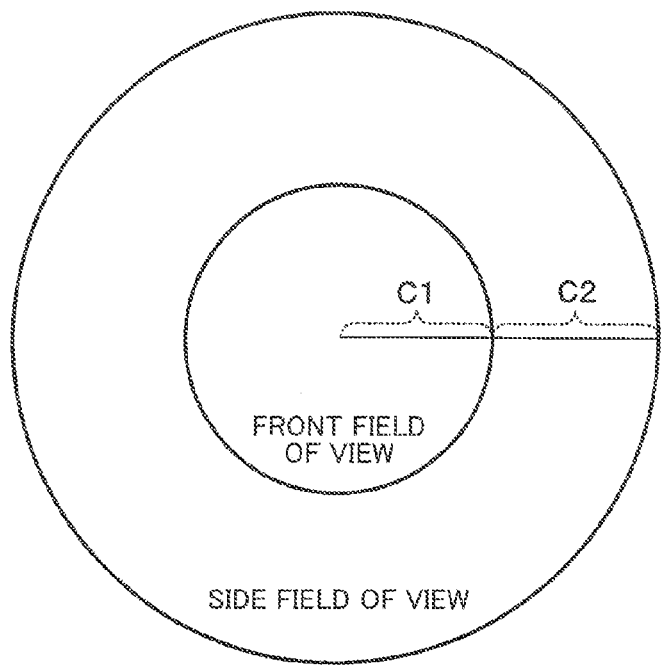
FIGS. 27A and 27B are views illustrating a process performed by a scaling section according to the third embodiment.
Figure 27B:
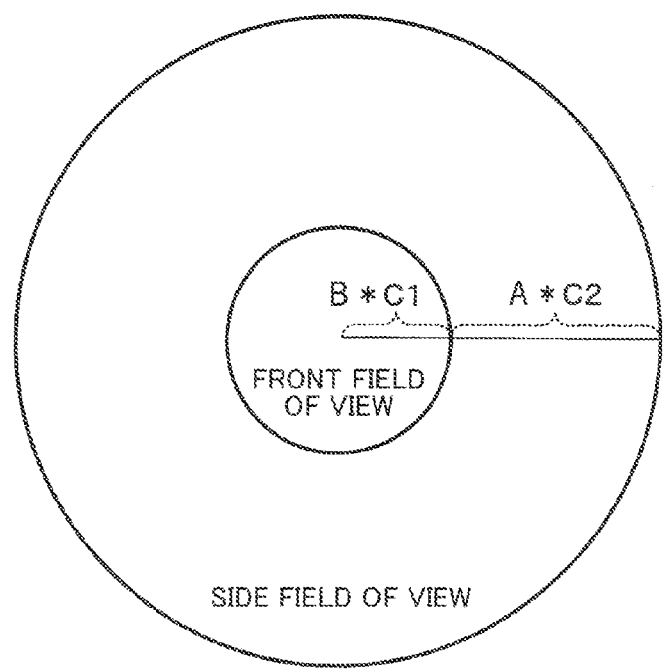

The process performed by the scaling section 414 is described in detail below. As illustrated in FIG. 27A, the radius of the front-field-of-view area is referred to as C1, and the distance obtained by subtracting the radius C1 from the radius of the entire area that includes the side-field-of-view area and the front-field-of-view area is referred to as C2. As illustrated in FIG. 27B, the scaling section 414 enlarges the side-field-of-view area by a scaling factor A (A≥1), and reduces the front-field-of-view area by a scaling factor B (B≤1). The scaling factor A is increased as the curve angle increases.

The relationship between the scaling factor A and the scaling factor B is indicated by the following expression (8). The scaling factor A is set within the range indicated by the following expression (9). The side-field-of-view area can be enlarged, and the front-field-of-view area can be reduced while maintaining the size of the entire image using the expressions (8) and (9).

$$B=1+(1-A)\cdot C2/C1 \quad (8)$$

$$1 \le A \le 1+C1/C2 \quad (9)$$

For example, when the absolute value of the maximum mechanical curve angle (maximum curve angle) is referred to as θmax, and the absolute value of the curve angle is referred to as θ, the scaling factor A is shown by the following expression (10).

$$A=(\theta/\theta max)*(C1/C2)+1 \quad (10)$$

Figures 28, 29:
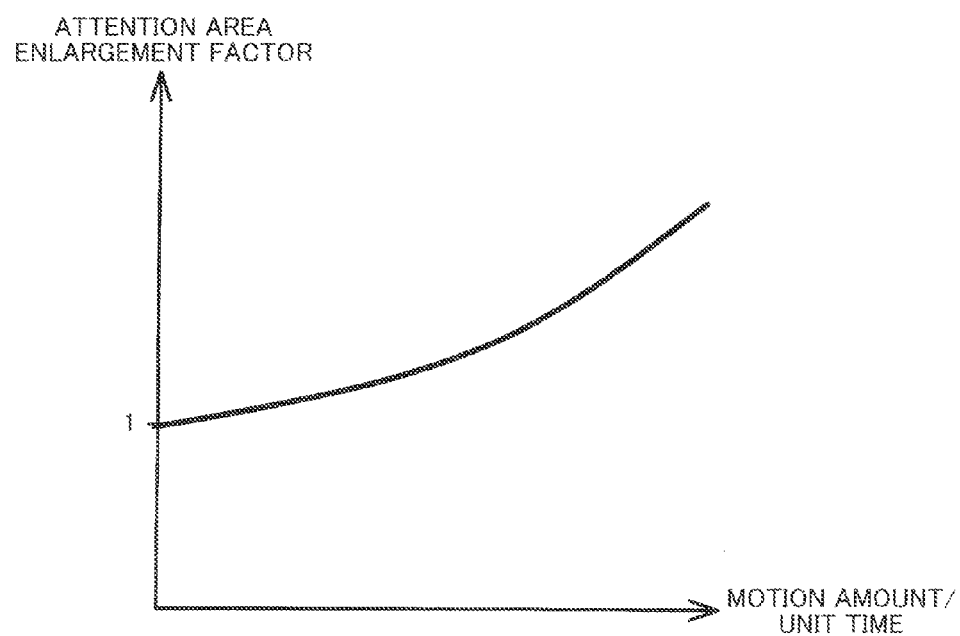
FIG. 28 illustrates an example of a look-up table that links a scaling factor A to a curve angle θ.
FIG. 29 illustrates an example of enlargement factor characteristics with respect to a curve motion amount.

As illustrated in FIG. 28, a look-up table that links the scaling factor A to the curve angle θ may be provided in advance, and the scaling factor A may be set based on the look-up table.

A pixel coordinate transformation process during the scaling process is described below. The following description illustrates an example in which the image is rectangular or elliptical. The vertical dimension or the horizontal dimension of the image, whichever is larger, is used as a reference. As shown by the following expression (11), points within d pixels from the center are reduced by the scaling factor B, and the remaining points are enlarged by the scaling factor A. For example, when the y-coordinate value of the pixel indicates a position within d pixels from the center, and the x-coordinate value of the pixel indicates a position outside d pixels from the center, the coordinates of the pixel are multiplied by B in the y-axis direction, and multiplied by A in the x-axis direction based on the center of the image.

$$x1' = B \cdot x1, \quad (11)$$
$$\ldots$$
$$xi' = B \cdot xi,$$
$$\ldots$$
$$xd' = B \cdot xd,$$
$$xd+1' = xr - A \cdot (r-(d+1)),$$
$$\ldots$$
$$xj' = xr - A \cdot (r-j),$$
$$\ldots$$
$$xr' = xr$$

where, d=C1, r=C1+C2, xi and xj are the coordinates of the pixel before the scaling process, xi' and xj' are the coordinates of the pixel after the scaling process, and i and j are natural numbers that satisfy 0<i≤d≤j≤r.

The pixel position after the scaling process does not necessarily coincide with a discrete pixel position. A pixel value is not necessarily generated at each pixel position after the scaling process. Therefore, the final image is generated by performing the interpolation process using adjacent pixels in the same manner as in the first embodiment.

4.4. Curve Motion Amount Detection Section

The process performed by the curve motion amount detection section 432 is described in detail below. The operation amount detection sensor 203 detects the rotation amount of the curve operation lever 201 per unit time. The curve motion amount detection section 432 calculates the curve motion amount from the detected rotation amount.

Note that the configuration according to the third embodiment is not limited thereto. The curve motion amount may be calculated based on the pull/push length of the curve operation wire 306 per unit time. The curve motion amount is not limited to a change in the curve angle per unit time. It suffices that the curve motion amount information be obtained as information that indicates the curve motion amount. For example, the curve motion amount information may be the rotation amount of the curve operation lever 201 per unit time, or may be the pull/push length of the curve operation wire 306 per unit time.

As described above with reference to FIG. 2C and the like, a lesion area that is positioned on the back side of folds can be found within the side field of view by performing a screening operation using a wide-angle endoscope. When the operator has found a lesion area, the operator curves the insertion section 300 by operating the curve operation lever

201 so that the lesion area can be observed within the front field of view (i.e., the lesion area can be easily observed within the front field of view as compared with the side field of view). Specifically, it is considered that the lesion area is positioned within the side field of view during the curve operation. The operator stops the curve operation when the lesion area is observed within the front field of view.

In the third embodiment, the side field of view is enlarged when the operator has started the curve operation, and the front field of view is enlarged (or displaced by the original scaling factor) when the operator has stopped the curve operation. When the curve operation has stopped after the curve angle has reached the maximum angle, it is considered that the attention area for the operator remains within the side field of view. Therefore, the side field of view is continuously enlarged.

Specifically, the attention area setting section 413 sets the attention area corresponding to the curve motion amount acquired by the curve motion amount detection section 432. The attention area setting section 413 sets an area within the side field of view to be the attention area when the curve motion amount is large (i.e., when the insertion section 300 is curved to a large extent). Note that the attention area setting section 413 may set the attention area only when the curve motion amount is equal to or larger than a threshold value.

As illustrated in FIG. 29, the scaling section 414 increases the enlargement factor as the curve motion amount detected by the curve motion amount detection section 432 increases, and performs the enlargement process on the attention area within the captured image. The scaling section 414 sets the reduction factor corresponding to the enlargement factor and the size of the image, and performs the reduction process on an area within the front field of view. The details of the process are the same as those described above with reference to FIG. 27B and the like.

According to the third embodiment, the state information acquisition section 430 includes the curve angle detection section 431 (see FIG. 25). The curve angle detection section 431 acquires the curve angle information as the state information, the curve angle information indicating the curve angle (i.e., the angle θ in FIGS. 26A to 26C) of the end of the scope. The attention area setting section 413 sets the attention area based on the acquired curve angle information.

The above configuration makes it possible to determine the observation area that attracts the operator's attention from the curve angle, and provide an image that is convenient to the operator by enlarging the observation area.

The attention area setting section 413 may set an area of the captured image that corresponds to the side field of view to be the attention area when it has been determined that the curve angle is larger than a threshold value (see FIG. 27A and the like).

It is considered that the operator curves the end of the scope when a lesion is positioned within the side field of view. The above configuration makes it possible to set the attention area within the side field of view, and enlarge the attention area. It is considered that the curve operation with a small curve angle (i.e., a curve angle equal to or smaller than the threshold value) is an error or a fine adjustment of the front field of view. It is possible to prevent a situation in which the attention area is unnecessarily enlarged or reduced by performing the determination process using the threshold value.

Note that an area that corresponds to the front field of view refers to an area in which the object within the front field of view is captured. For example, an area that corresponds to the front field of view refers to an area in which the object positioned in the direction of the optical axis of the objective optical system is captured. For example, when the optical axis coincides with the center of the image, an area that corresponds to the front field of view refers to a center area that includes the center of the image.

An area that corresponds to the side field of view refers to an area in which the object within the side field of view is captured. For example, an area that corresponds to the side field of view refers to an area in which the object positioned in the direction orthogonal to the optical axis of the objective optical system is captured. For example, when the optical axis coincides with the center of the image, an area that corresponds to the side field of view refers to an area around the center area.

The scaling section 414 may control the scaling factors A and B for the attention area or an area (another area) other than the attention area corresponding to the curve angle (see FIG. 27A and the like).

Specifically, the scaling section 414 may increase the scaling factor (enlargement factor) A for the attention area as the curve angle increases.

Since it is considered that the operator pays attention to the side field of view when the curve angle is large, it is possible to provide an image that can be easily observed by the operator by enlarging the side field of view.

The state information acquisition section 430 may include the curve motion amount detection section 432 (see FIG. 25). The curve motion amount detection section 432 may acquire the curve motion amount information as the state information, the curve motion amount information indicating the curve motion amount (i.e., a change in the angle θ in FIGS. 26A to 26C per unit time) of the end of the scope. The attention area setting section 413 may set the attention area based on the acquired curve motion amount information.

The above configuration makes it possible to determine the observation area that attracts the operator's attention from the curve motion amount, and provide an image that is convenient to the operator by enlarging the observation area.

The attention area setting section 413 may set an area of the captured image that corresponds to the side field of view to be the attention area when it has been determined that the curve motion amount is larger than a threshold value.

It is considered that the operator curves the end of the scope when a lesion is positioned within the side field of view. The above configuration makes it possible to set the attention area within the side field of view, and enlarge the attention area. It is considered that the curve operation with a small curve motion amount (i.e., a curve motion amount equal to or smaller than the threshold value) is an error or a fine adjustment of the front field of view. It is possible to prevent a situation in which the attention area is unnecessarily enlarged or reduced by performing the determination process using the threshold value.

The scaling section 414 may control the scaling factors A and B for the attention area or an area (another area) other than the attention area corresponding to the curve motion amount (see FIG. 27A and the like).

Specifically, the scaling section 414 may increase the scaling factor (enlargement factor) A for the attention area as the curve motion amount increases.

It is considered that the operator desired to quickly move the lesion area within the side field of view to the center area of the image when the curve motion amount is large. It is possible to display the lesion area within the side field of view in the center area of the image by enlarging the side field of view, and provide an image that is convenient to the operator.

5. Fourth Embodiment
5.1. Endoscope System

A fourth embodiment in which the attention area is set based on distance information about the distance to the object that is estimated from the intensity of light emitted from the light source is described below.

Figure 30:
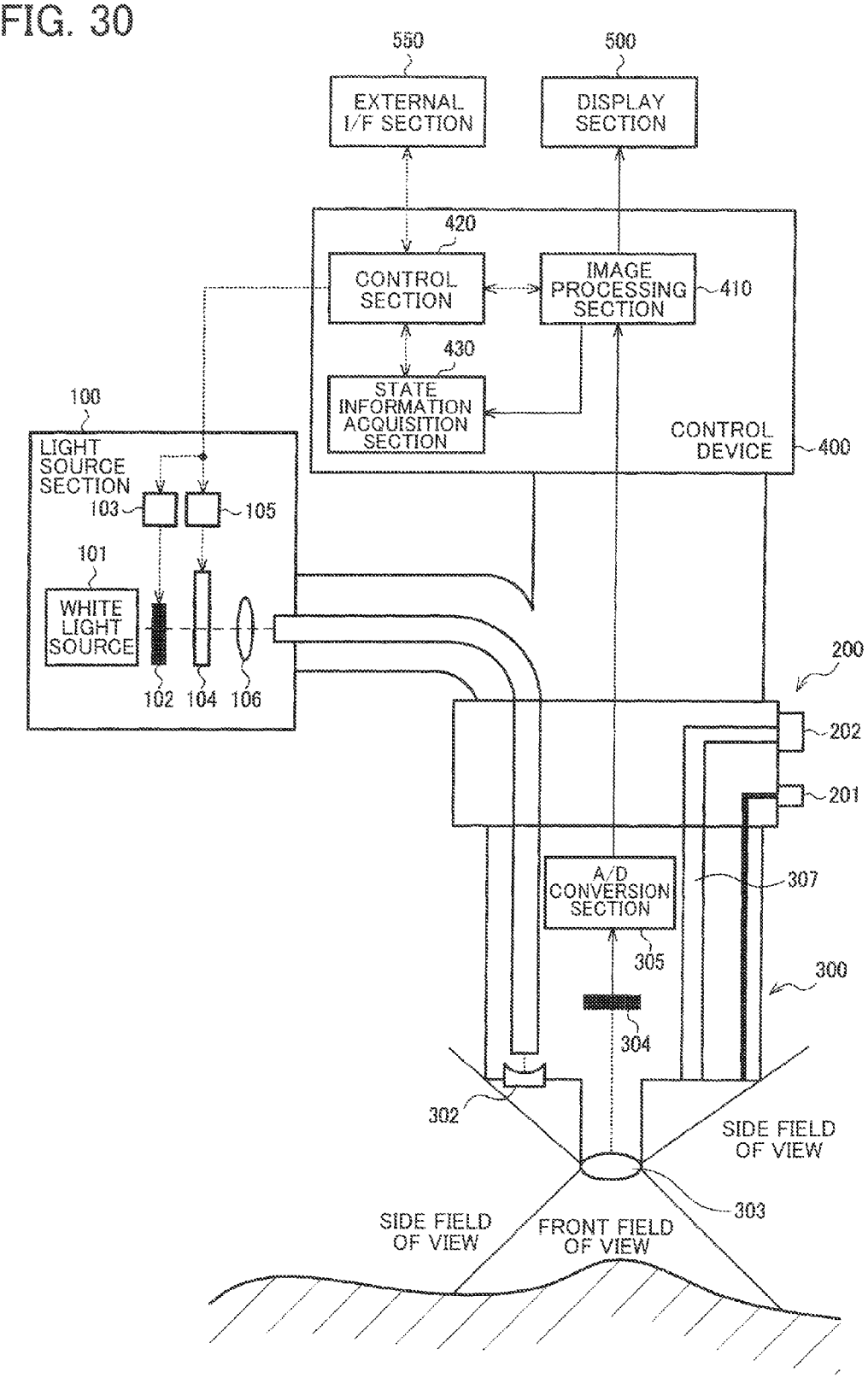
FIG. 30 illustrates a configuration example of an endoscope system according to a fourth embodiment.

FIG. 30 illustrates a configuration example of an endoscope system according to the fourth embodiment. The endoscope system includes a light source section 100, an operation section 200, an insertion section 300, a control device 400, a display section 500, and an external I/F section 550. Note that the same elements as those described above with reference to FIG. 3 and the like are indicated by identical reference signs, and description of these elements is appropriately omitted.

The control device 400 includes an image processing section 410, a control section 420, and a state information acquisition section 430. The image signals processed by the image processing section 410 are transmitted to the display section 500 and the state information acquisition section 430. The control section 420 is connected to a light source aperture driver section 103, a rotation driver section 105, the image processing section 410, the state information acquisition section 430, and an external I/F section 550, and controls the light source aperture driver section 103, the rotation driver section 105, the image processing section 410, the state information acquisition section 430, and the external I/F section 550.

A dimming process performed by the endoscope system is described below. Since the end of the insertion section 300 moves closer to or away from the observation area when the observation area is observed in a state in which the intensity of illumination light is constant, the captured image may be subjected to blown out highlights or blocked up shadows. In order to prevent such a situation, a dimming process that maintains the image signals at an appropriate brightness is used. The dimming process normally maintains the captured image at a constant brightness by adjusting the intensity of light emitted from the light source section 100, the analog gain of the image sensor 304, or the digital gain of the image processing section 410.

In the fourth embodiment, information about the intensity of light emitted from the light source section 100 is acquired in a state in which the dimming process is performed. The distance information about the distance to the object is estimated based on the information about the intensity of light emitted from the light source section 100, and the scaling process performed on the attention area and an area other than the attention area is adaptively controlled based on the distance information.

5.2. State Information Acquisition Section

The method that estimates the distance to the object, and sets the attention area based on the distance is described in detail below.

When the operator has found an area that is considered to be a lesion area during observation using the endoscope system, the operator moves the end of the insertion section 300 closer to the area that is considered to be a lesion area. In this case, the intensity of reflected light from the object increases, and the brightness of the image signals of the captured image increases. In the fourth embodiment, the state information acquisition section 430 performs the dimming process, and decreases the aperture area of the light source aperture 102 until the image has the target observation brightness by controlling the light source aperture driver section 103 through the control section 420.

When the end of the insertion section 300 is positioned away from the observation area, the intensity of reflected light from the object decreases, and the brightness of the image signals of the captured image decreases. In this case, the state information acquisition section 430 increases the aperture area of the light source aperture 102 until the image has the target observation brightness by controlling the light source aperture driver section 103 through the control section 420. Specifically, the end of the insertion section 300 is positioned close to the object when the aperture area of the light source aperture 102 is small, and the end of the insertion section 300 is positioned away from the object when the aperture area of the light source aperture 102 is large.

In the fourth embodiment, an objective optical system that allows the operator to simultaneously observe the object within the front field of view and the object within the (substantially) side field of view (see FIG. 1) is used in order to observe the object over a wide range. Therefore, the front field of view (center area) and the side field of view (peripheral area) are displayed around the coordinates (N/2, M/2) of the center of the image (see FIG. 2D).

Figure 31A:
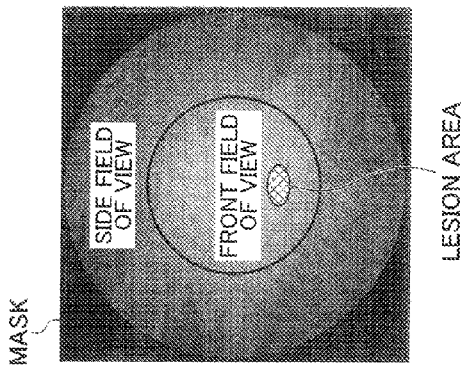
FIGS. 31A to 31D are views illustrating a distance estimation method.
Figure 31B:
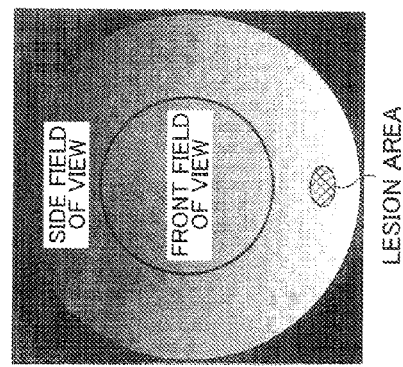
Figure 31C:
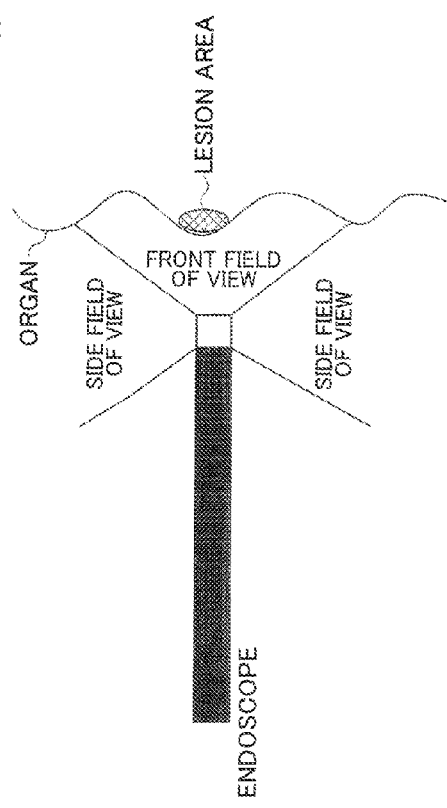
Figure 31D:
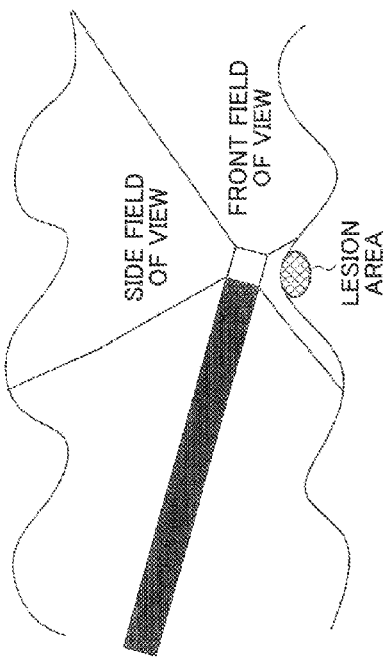

When the operator has found an area that is considered to be a lesion area, the operator normally positions the lesion area within the center area (front field of view) of the image signals (see FIGS. 31A and 31B). However, when observing an elongated hollow tubular part (e.g., intestine), it is difficult to position the lesion area within the front field of view of the image signals due to a limited space (see FIGS. 31C and 31D). Specifically, it is difficult to rotate the end of the insertion section 300 due to a limited space. Therefore, the operator has to position the lesion area within the side field of view of the image signals (see FIG. 31D).

In the fourth embodiment, the dimming process is performed on an area within the front field of view or an area within the side field of view corresponding to the photometric mode. It is determined that the object is observed in a state in which the end of the scope is brought close to the object when the aperture area of the light source aperture 102 is smaller than a threshold value, and the area subjected to the dimming process is set to be the attention area.

Figure 32:
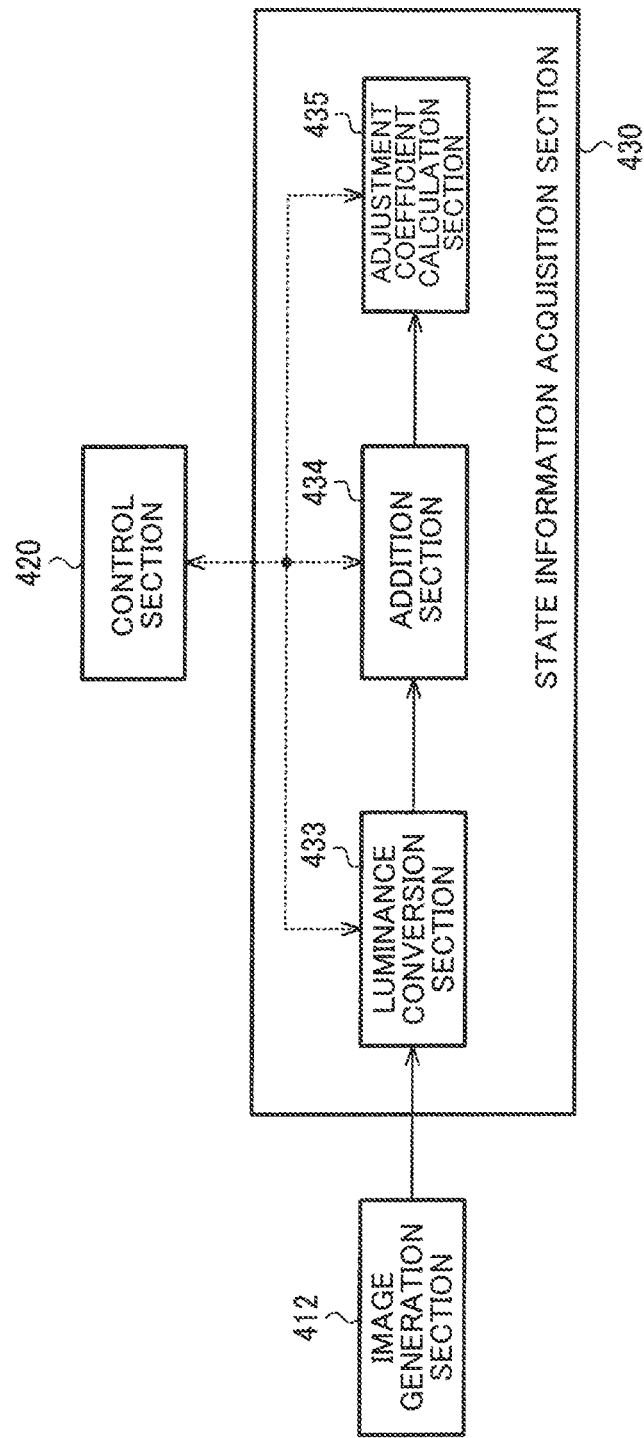
FIG. 32 illustrates a detailed configuration example of a state information acquisition section according to the fourth embodiment.

A process that acquires information about the aperture area of the light source aperture 102 as the state information is described below. FIG. 32 illustrates a detailed configuration example of the state information acquisition section 430 according to the fourth embodiment. The state information acquisition section 430 includes a luminance conversion section 433, an addition section 434, and an adjustment coefficient calculation section 435.

The image generation section 412 is connected to the adjustment coefficient calculation section 435 through the luminance conversion section 433 and the addition section 434. The control section 420 is bidirectionally connected to the luminance conversion section 433, the addition section 434, and the adjustment coefficient calculation section 435.

Figure 33:
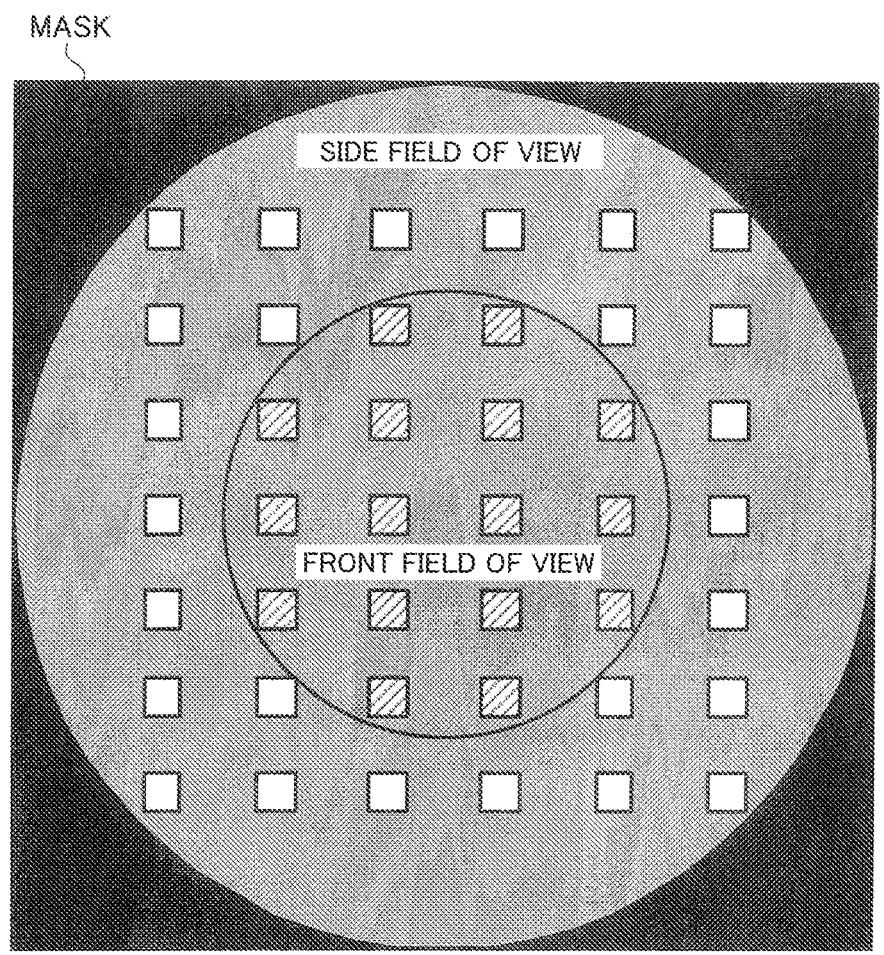
FIG. 33 is a view illustrating a process performed by a state information acquisition section according to the fourth embodiment.

The luminance conversion section 441 sets sampling pixels (coordinates (x, y)) to the image signals obtained by the image generation process at given intervals, calculates the luminance signals $Yi(x, y)$ of the sampling pixels using the expression (1), and transmits the calculated luminance signals $Yi(x, y)$ to the addition section 434 (see FIG. 33).

The addition section 434 averages the luminance signals $Yi(x, y)$ of the sampling pixels using the following expression (12) to calculate a brightness measured value $Yd$. The addition section 434 transmits the calculated brightness measured value Yd to the adjustment coefficient calculation section 435.

$$Yd = \frac{\sum_{i=0}^{n} \{Y_i(x, y) \times a(x, y)\}}{n} \quad (12)$$

where, n is the number (constant) of sampling pixels that is set corresponding to the angle of view of the image signals, and a(x, y) is a weighting coefficient for the sampling pixels.

In the fourth embodiment, a plurality of photometric modes are provided corresponding to the observation state (see FIG. 31A and the like). The operator sets the photometric mode via the external I/F section 550. For example, when the operator desires to pay attention to the front field of view of the image signals, the operator sets the photometric mode to a front mode. When the photometric mode has been set to the front mode, the weighting coefficient for the sampling pixels included within the front field of view in FIG. 33 is set to be larger than the weighting coefficient for the sampling pixels included within the side field of view. Therefore, since the weighting of the dimming process on the front field of view increases, the dimming process when observing the object that is positioned within the front field of view can be performed with high accuracy.

When the operator desires to pay attention to the side field of view of the image signals, the operator sets the photometric mode to a side mode. When the photometric mode has been set to the side mode, the weighting coefficient for the sampling pixels included within the side field of view in FIG. 33 is set to be larger than the weighting coefficient for the sampling pixels included within the front field of view. Therefore, the dimming process when observing the object in a state in which the end of the insertion section 300 is brought close to the object that is positioned within the side field of view (e.g., when observing a lumen) can be performed within high accuracy.

Note that the weighting coefficient a(x, y) may be set using a method other than the above method. For example, the weighting coefficient a(x, y) for the sampling pixels may be set in proportion to the distance from the coordinates (N/2, M/2) of the center of the image.

The adjustment coefficient calculation section 435 calculates a light source aperture adjustment coefficient Lc by the following expression (13) using the brightness measured value Yd output from the addition section 434 and a brightness target value Ybase set in advance.

$$Lc = Ybase/Yd \quad (13)$$

The adjustment coefficient calculation section 435 transmits the light source aperture adjustment coefficient Lc to the control section 420, and the light source aperture driver section 103 controls the aperture area of the light source aperture 102 based on the light source aperture adjustment coefficient Lc output from the control section 420.

5.3. Attention Area Setting Section and Scaling Section

The attention area setting section 413 acquires the information about the aperture area of the light source aperture 102 based on the control signal output from the control section 420. When the object is observed in a state in which the end of the insertion section 300 is brought close to the object, the aperture area of the light source aperture 102 decreases due to the dimming process. Therefore, the attention area setting section 413 sets the attention area within the front field of view or the side field of view when the aperture area is smaller than a given threshold value. Specifically, the attention area setting section 413 sets the attention area within the front field of view when the photometric mode is the front mode, and sets the attention area within the side field of view when the photometric mode is the side mode. The attention area setting section 413 transmits information about the set attention area to the scaling section 414.

The scaling section 414 performs the scaling process on the attention area set by the attention area setting section 413. When the attention area is set within the front field of view, the scaling section 414 enlarges the image within the front field of view by a given enlargement factor in the same manner as in the third embodiment. The scaling section 414 sets a given radius range of the side field of view that is adjacent to the front field of view in the same manner as in the third embodiment, and reduces the radius range by a given reduction factor. The scaling section 414 sets the scaling factor for the remaining side field of view to 1 (i.e., does not perform the scaling process on the remaining side field of view). For example, the scaling section 414 sets the scaling factor for the front field of view to B>1, and sets the scaling factor for the side field of view to A≤1 in FIG. 27B. Note that the scaling factor for the side field of view is not limited thereto. For example, the entire side field of view may be reduced.

When the attention area is set within the side field of view, the scaling section 414 enlarges the image within the side field of view by a given enlargement factor in the same manner as in the third embodiment. The scaling section 414 sets a given radius range of the front field of view that is adjacent to the side field of view in the same manner as in the third embodiment, and reduces the radius range by a given reduction factor. The scaling section 414 sets the scaling factor for the remaining front field of view to 1 (i.e., does not perform the scaling process on the remaining front field of view). For example, the scaling section 414 sets the scaling factor for the front field of view to B≤1, and sets the scaling factor for the side field of view to A>1 in FIG. 27B. Note that the scaling factor for the front field of view is not limited thereto. For example, the entire front field of view may be reduced.

The scaling section 414 returns the scaling factor (enlargement factor) for the attention area to 1 when the aperture area has become larger than the given threshold value (i.e., the attention area is not set) in a state in which the attention area is enlarged by the above process.

It is possible to improve the visibility of the lesion area for the operator by adaptively performing the scaling process on the attention area (within the front field of view or the side field of view) corresponding to the state of the aperture of the light source.

5.4. Modification

Although an example in which the scaling process is adaptively performed corresponding to the state (aperture area) of the light source aperture 102 has been described above, the configuration according to the fourth embodiment is not limited thereto. For example, the scaling process may be performed based on light intensity control information (e.g., drive current) about an LED light source.

Figure 34:
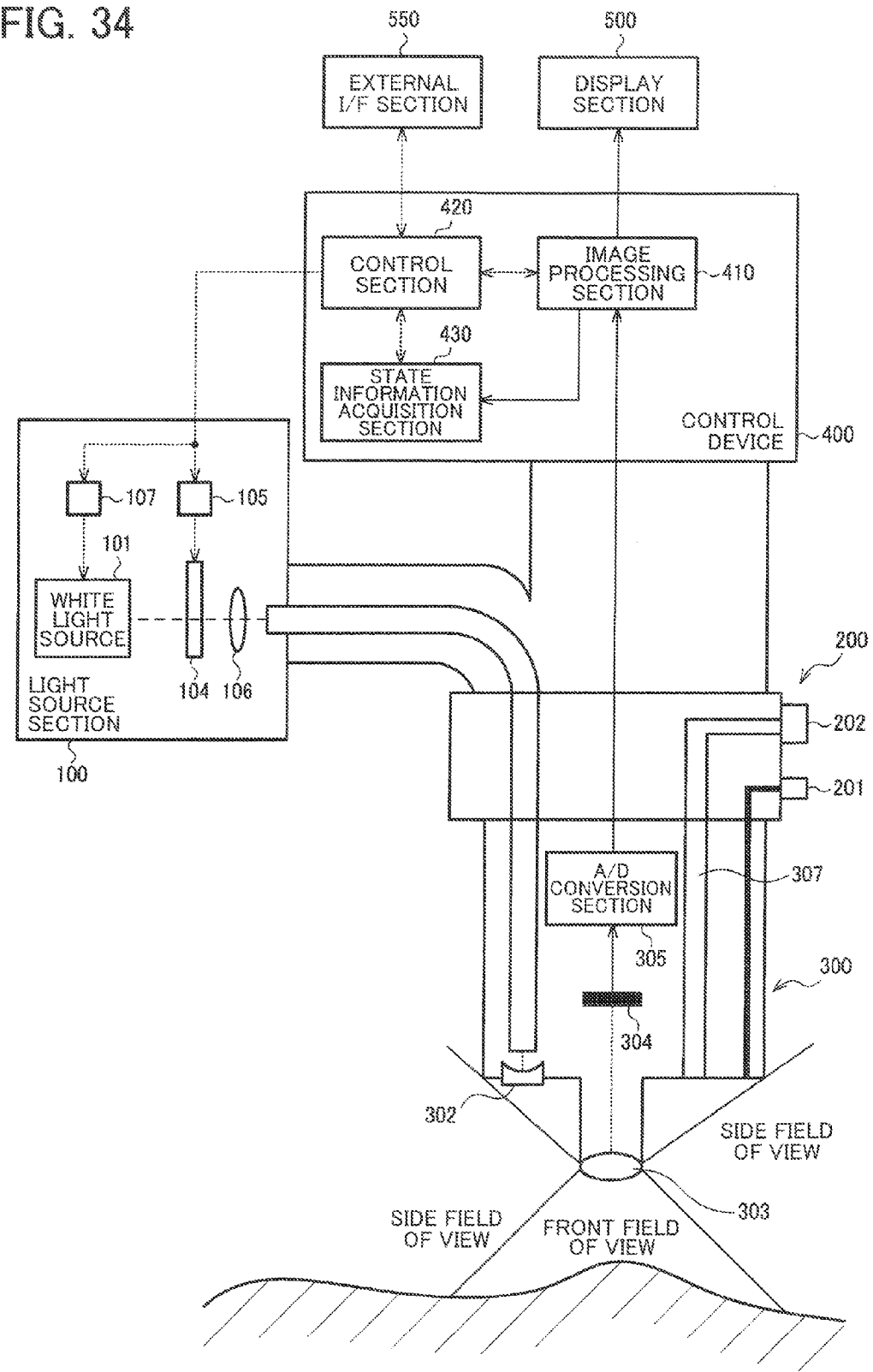
FIG. 34 illustrates a modified configuration example of an endoscope system.

FIG. 34 illustrates a modified configuration example of the endoscope system that performs such a process. The endoscope system includes a light source section 100, an operation section 200, an insertion section 300, a control device 400, a display section 500, and an external I/F section 550. Note that the same elements as those described above with reference to FIG. 3 and the like are indicated by identical reference signs, and description of these elements is appropriately omitted.

The light source section 100 includes a white light source 101, a rotary color filter 104, a rotation driver section 105, a condenser lens 106, and a light source control section 107 that controls the intensity of light emitted from the light source. The white light source 110 is implemented by an LED light source. The light source control section 107 controls the intensity of light emitted from the LED light source based on the control signal output from the control section 420. The control section 420 adjusts the intensity of light emitted from the LED light source based on the adjustment coefficient Lc (see the expression (13)).

The attention area setting section 413 sets the attention area based on a light intensity control signal output from the control section 420. Specifically, when the intensity of emitted light is smaller than a threshold value, the attention area setting section 413 determines that the end of the scope has been brought close to the object, and sets the attention area corresponding to the photometric mode. The scaling section 414 performs the scaling process on the attention area set by the attention area setting section 413.

According to the fourth embodiment, the state information acquisition section 430 acquires the distance information that indicates the distance between the object and the end of the scope based on the intensity of light emitted from the light source section 100 that illuminates the object (see FIG. 32 and the like). The attention area setting section 413 sets the attention area using the distance information as the state information.

Specifically, the attention area setting section 413 sets the attention area when it has been determined that the distance is smaller than a threshold value.

More specifically, the endoscope system includes a mode setting section (i.e., the control section 420 illustrated in FIG. 30) and a dimming control section (i.e., the state information acquisition section 430 and the control section 420 illustrated in FIG. 32). The mode setting section sets the photometric mode to a first photometric mode (front mode) or a second photometric mode (side mode), the first photometric mode being a mode in which the dimming control process is performed on an area that corresponds to the front field of view, and the second photometric mode being a mode in which the dimming control process is performed on an area that corresponds to the side field of view. The dimming control section controls the intensity of emitted light by controlling the aperture area of the aperture (i.e., the light source aperture 102 illustrated in FIG. 30) of the light source section 100 based on the brightness of the area that is subjected to the dimming control process in the photometric mode set by the mode setting section. The distance information is the aperture area controlled by the dimming control section. The attention area setting section 413 sets the area that is subjected to the dimming control process in the photometric mode set by the mode setting section to be the attention area when it has been determined that the aperture area is smaller than a threshold value.

Since it is considered that an area to which the end of the scope has been brought close is the observation target area for the operator, it is possible to appropriately enlarge the observation target area for the operator by setting the attention area corresponding to the distance, and enlarging the attention area. Since the brightness of the image is maintained constant by the dimming control process, whether or not the end of the scope has been brought close to the object can be determined by estimating the distance based on the dimming control process instead of the image.

6. Fifth Embodiment 6.1. Endoscope System

A fifth embodiment in which the attention area is set based on distance information about the distance to the object that is estimated from the brightness of the image is described below.

Figure 35:
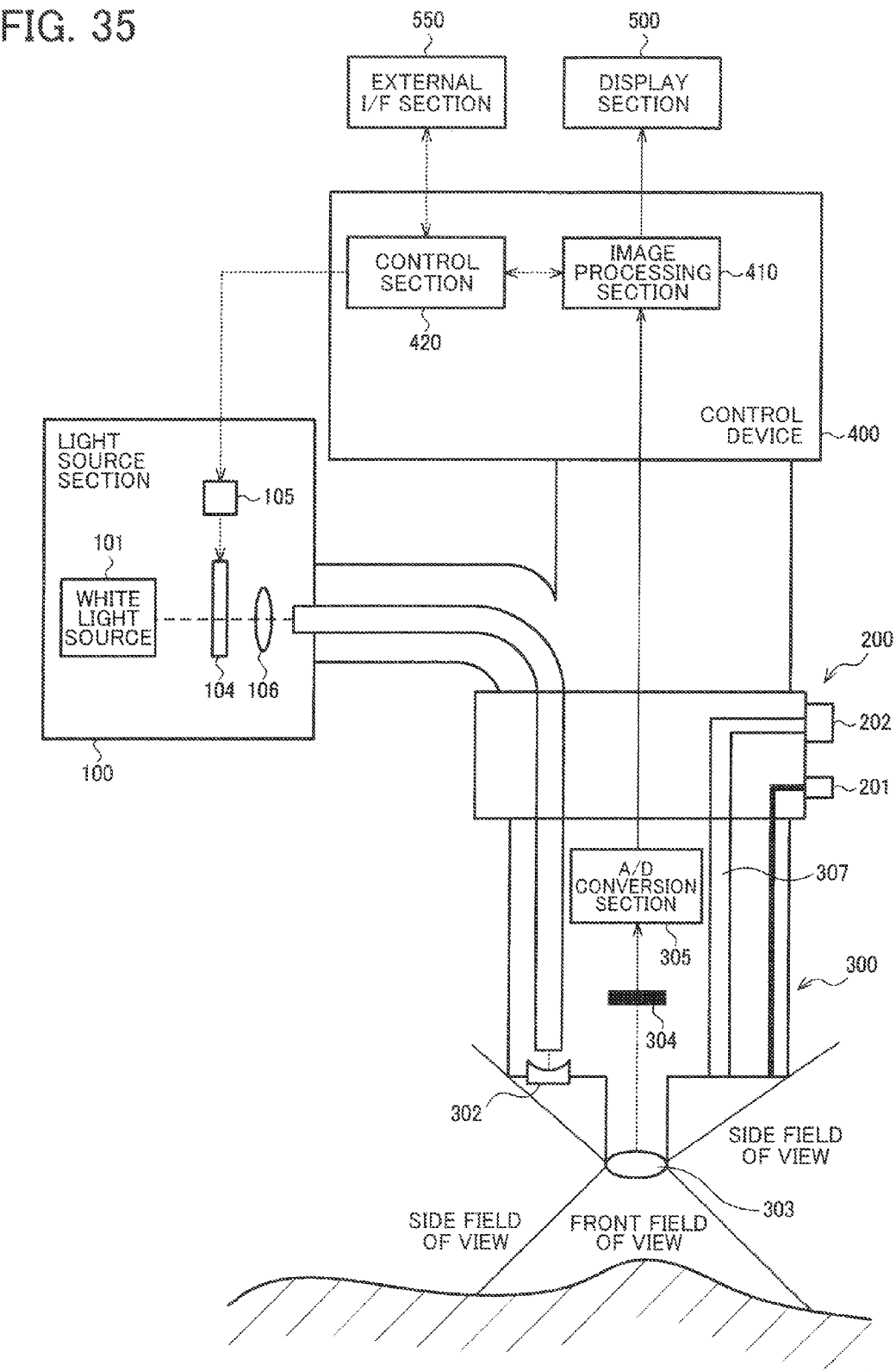
FIG. 35 illustrates a configuration example of an endoscope system according to a fifth embodiment.

FIG. 35 illustrates a configuration example of an endoscope system according to the fifth embodiment. The endoscope system includes a light source section 100, an operation section 200, an insertion section 300, a control device 400, a display section 500, and an external I/F section 550. Note that the same elements as those described above with reference to FIG. 3 and the like are indicated by identical reference signs, and description of these elements is appropriately omitted.

The light source section 100 includes a white light source 101, a rotary color filter 104, a rotation driver section 105, and a condenser lens 106. The configuration of the light source section 100 according to the fifth embodiment differs from the configuration of the light source section 100 according to the first embodiment in that the light source aperture 102 and the light source aperture driver section 103 are omitted.

A relatively bright area of the image signals is considered to be an area in which the distance between the end of the insertion section 300 and the object is short. In the fifth embodiment, the brightness of the image signals is calculated on a local area basis, and a relatively bright local area among a plurality of local areas is set to be the attention area.

6.2. Attention Area Setting Section and Scaling Section

Figure 36:
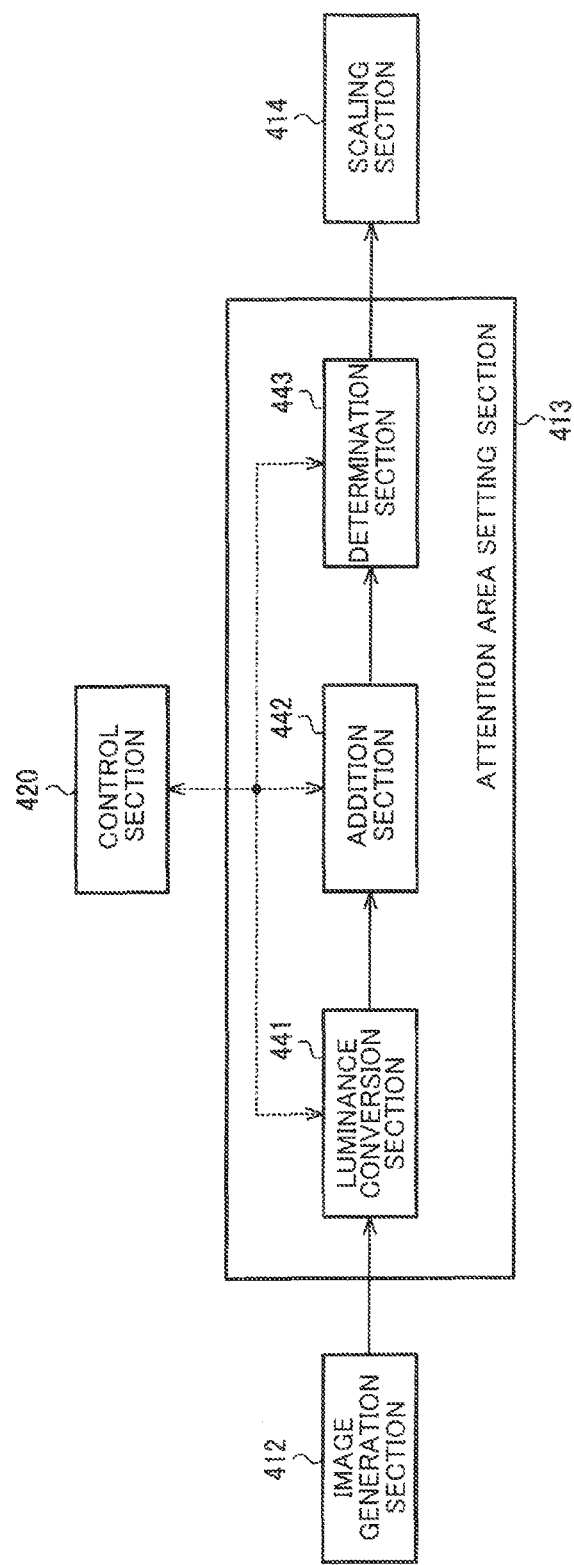
FIG. 36 illustrates a detailed configuration example of an attention area setting section according to the fifth embodiment.

FIG. 36 illustrates a detailed configuration example of an attention area setting section 413 according to the fifth embodiment. The attention area setting section 413 includes a luminance conversion section 441, an addition section 442, and a determination section 443. The image generation section 412 is connected to the luminance conversion section 441. The luminance conversion section 441 is connected to the addition section 442. The addition section 442 is connected to the determination section 443. The determination section 443 is connected to the scaling section 414. The control section 420 is bidirectionally connected to the luminance conversion section 441, the addition section 442, and the determination section 443.

The luminance conversion section 441 calculates the luminance signals of the sampling pixels of the image signals obtained by the image generation process, and transmits the luminance signals of the sampling pixels to the addition section 442 (see FIG. 33).

The addition section 442 averages the luminance signals Yi(x, y) of the sampling pixels using the following expression (14) corresponding to the front field of view and the side field of view to calculate a brightness measured value Ydf of the front field of view and a brightness measured value Yds of the side field of view. Note that the center coordinates (N/2, M/2) of the image signals are set to be the origin, the pixels within a given radius are set to be the front field of view, and the remaining pixels are set to be the side field of view.

$$Ydf = \frac{\sum_{i=0}^{m} \{Y_i(x, y) \times a(x, y)\}}{m}, \tag{14}$$

$$Yds = \frac{\sum_{j=0}^{n} \{Y_j(x, y) \times b(x, y)\}}{n}$$

where, m is the number (constant) of sampling pixels within the front field of view, and n is the number (constant) of sampling pixels within the side field of view. m and n are set corresponding to the angle of view of the image signals. a(x, y) and b(x, y) are weighting coefficients.

Figure 37:
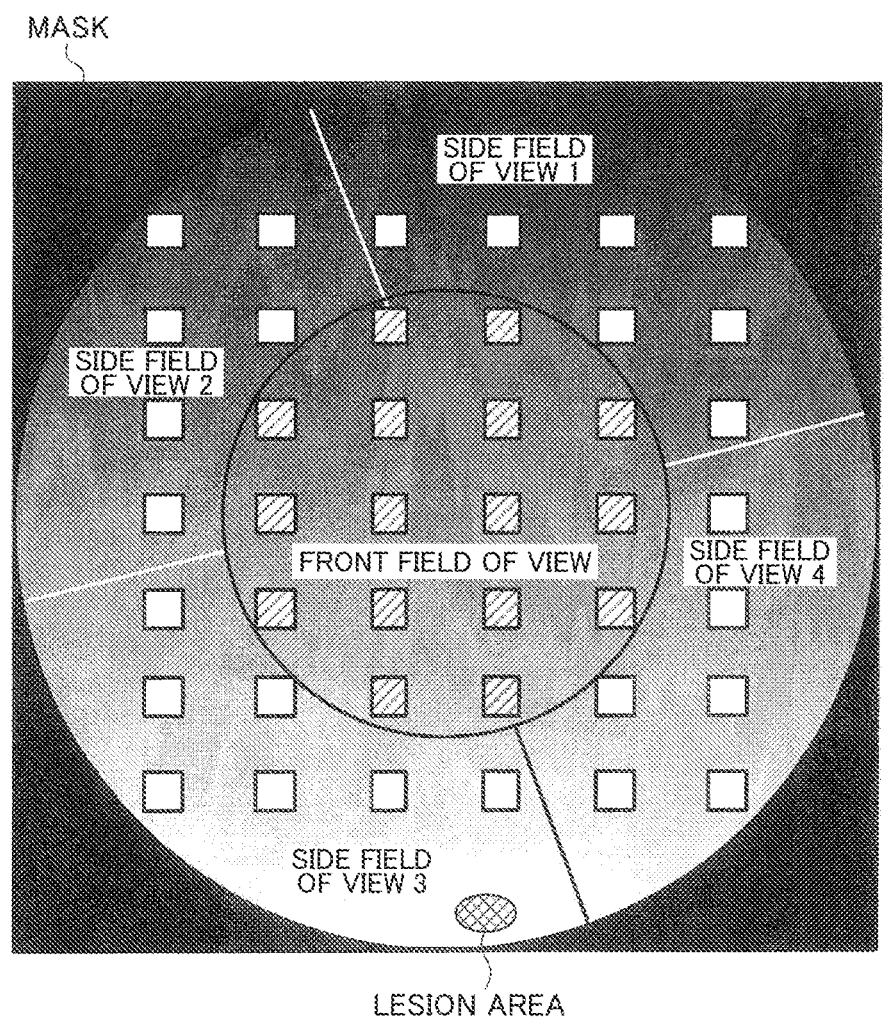
FIG. 37 is a view illustrating a modification of the fifth embodiment.

Although an example in which the image is divided into the front field of view and the side field of view, and the brightness measured value of each field of view is calculated has been described above, the configuration according to the fifth embodiment is not limited thereto. For example, when observing the object in a state in which the end of the insertion section 300 is positioned close to the object, it is unlikely that the entire side field of view is bright. Therefore, the side field of view may be divided into a plurality of areas (see FIG. 37), and the luminance signals Yi(x, y) of the sampling pixels included in each area may be averaged to calculate the brightness measured value of each area. In this case, the maximum value among the calculated brightness measured values of the plurality of areas is determined to the brightness measured value Yds of the side area. In FIG. 37, the brightness measured value of the side field of view 3 is a maximum. In this case, the brightness measured value of the side field of view 3 is transmitted to the determination section 443 as the brightness measured value Yds of the side area.

The determination section 443 sets the attention area based on the brightness measured values Ydf and Yds calculated by the addition section 442. Specifically, the determination section 443 sets an area that corresponds to the front field of view to be the attention area when the brightness measured value Ydf of the front field of view is larger than a given threshold value. The determination section 443 sets an area that corresponds to the side field of view to be the attention area when the brightness measured value Yds of the side field of view is larger than the given threshold value. The determination section 443 sets an area that corresponds to the front field of view or an area that corresponds to the side field of view, whichever is brighter, to be the attention area when the brightness measured values Ydf and Yds are larger than the given threshold value. The determination section 443 transmits information about the set attention area to the scaling section 414.

Figure 38C:
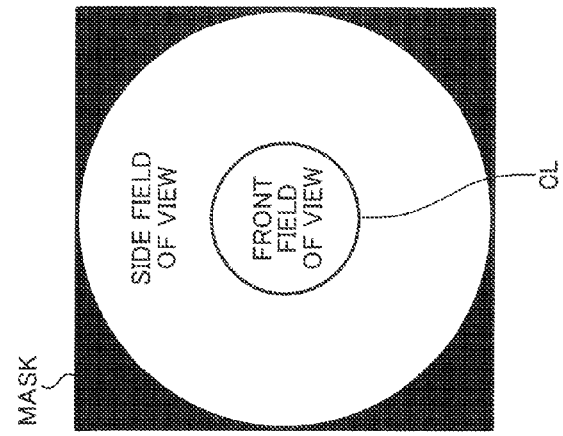
FIGS. 38A to 38C are views illustrating a process performed by a scaling section according to the fifth embodiment.
Figure 38B:
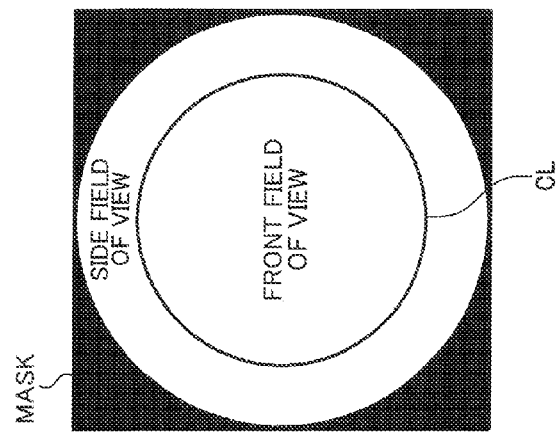
Figure 38A:
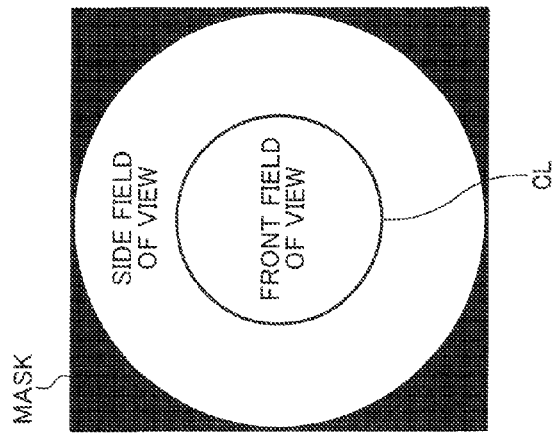

The scaling section 414 performs the scaling process on the attention area set by the determination section 443. The scaling process is performed in the same manner as in the third embodiment. FIG. 38A illustrates an image construction before the scaling process is performed. In FIG. 38A, the solid line CL indicates the boundary between the front field of view and the side field of view. As illustrated in FIG. 38B, when the attention area is set within the front field of view, the area of the front field of view is enlarged, and the area of the side field of view is reduced using the solid line CL as the boundary. As illustrated in FIG. 38C, when the attention area is set within the side field of view, the area of the side field of view is enlarged, and the area of the front field of view is reduced using the solid line CL as the boundary.

When the attention area is set within the front field of view and the side field of view, one of the attention area set within the front field of view and the attention area set within the side field of view may be enlarged, and the other of the attention area set within the front field of view and the attention area set within the side field of view may be reduced based on an instruction from the user, a prior setting, or the like. For example, the attention area that is enlarged/reduced may be changed based on an operation performed by the user.

According to the fifth embodiment, it is possible to improve the visibility of the lesion area for the operator by estimating the distance between the end of the insertion section 300 and the object from the brightness of the image signals, and adaptively performing the scaling process on the front field of view and the side field of view based on the estimated distance.

6.3. Software

In the fifth embodiment, some or all of the processes performed by each section of the image processing section 410 may be implemented by software. In this case, a CPU of a computer system (described later with reference to FIG. 72, for example) executes an image processing program.

Figure 39:
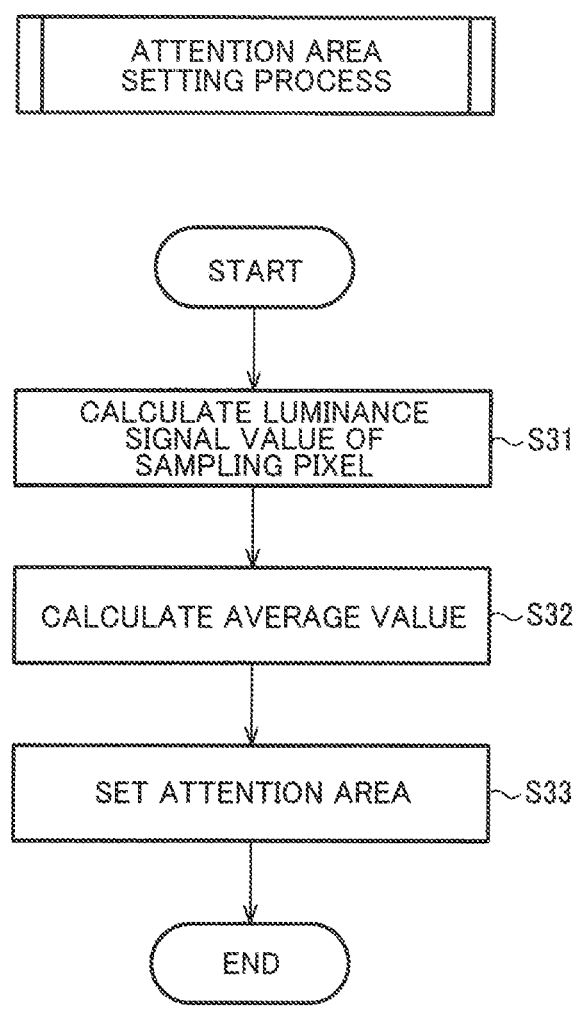
FIG. 39 illustrates an example of a detailed flowchart of an attention area setting process according to the fifth embodiment.

FIG. 39 illustrates an example of a detailed flowchart of the attention area setting process according to the fifth embodiment. The processes of the remaining steps of the image processing program are the same as described above in connection with the first embodiment (see FIG. 18 and the like).

As illustrated in FIG. 39, the luminance values of the sampling pixels of the image signals obtained by the image generation process are calculated using the expression (1) (S31). The average value Ydf of the front field of view and the average value Yds of the side field of view are calculated using the expression (14) (S32). An area that corresponds to the front field of view is set to be the attention area when the average value Ydf of the front field of view is larger than a given threshold value. An area that corresponds to the side field of view is set to be the attention area when the average value Yds of the side field of view is larger than the given threshold value (S33).

According to the fifth embodiment, the attention area setting section 413 includes a distance information acquisition section (i.e., the luminance conversion section 441 and the addition section 442 illustrated in FIG. 36). The distance information acquisition section acquires the distance information that indicates the distance between the object and the end of the scope based on the brightness (e.g., the luminance signal Yi(x, y) (see the expression (14)) of the captured image. The attention area setting section 413 sets the attention area based on the acquired distance information.

Specifically, the distance information acquisition section (e.g., the luminance conversion section 441 (luminance feature quantity calculation section in a broad sense)) calculates the luminance feature quantity relating to the luminance of the pixel of the captured image, and acquires the distance information based on the calculated luminance feature quantity.

More specifically, the distance information acquisition section divides the captured image into a plurality of areas (e.g., an area that corresponds to the front field of view and an area that corresponds to the side field of view), and acquires the brightness (brightness measured values Ydf and Yds) of each area as the distance information (see FIGS. 38A to 38C and the like). The attention area setting section 413 sets the brightest area among the plurality of areas to be the attention area as an area that is closest to the end of the scope.

The above configuration makes it possible to set the attention area based on the brightness of the image, and enlarge the attention area by performing the scaling process. Specifically, when the end of the scope is brought close to the observation target area for the operator, the observation target area becomes brighter due to illumination. Therefore, the observation target area for the operator can be appropriately enlarged by setting the attention area corresponding to the brightness of the image.

7. Sixth Embodiment 7.1. Endoscope System

A sixth embodiment in which a lesion area is detected using special light, and the detected lesion area is set to be the attention area is described below.

Figure 40:
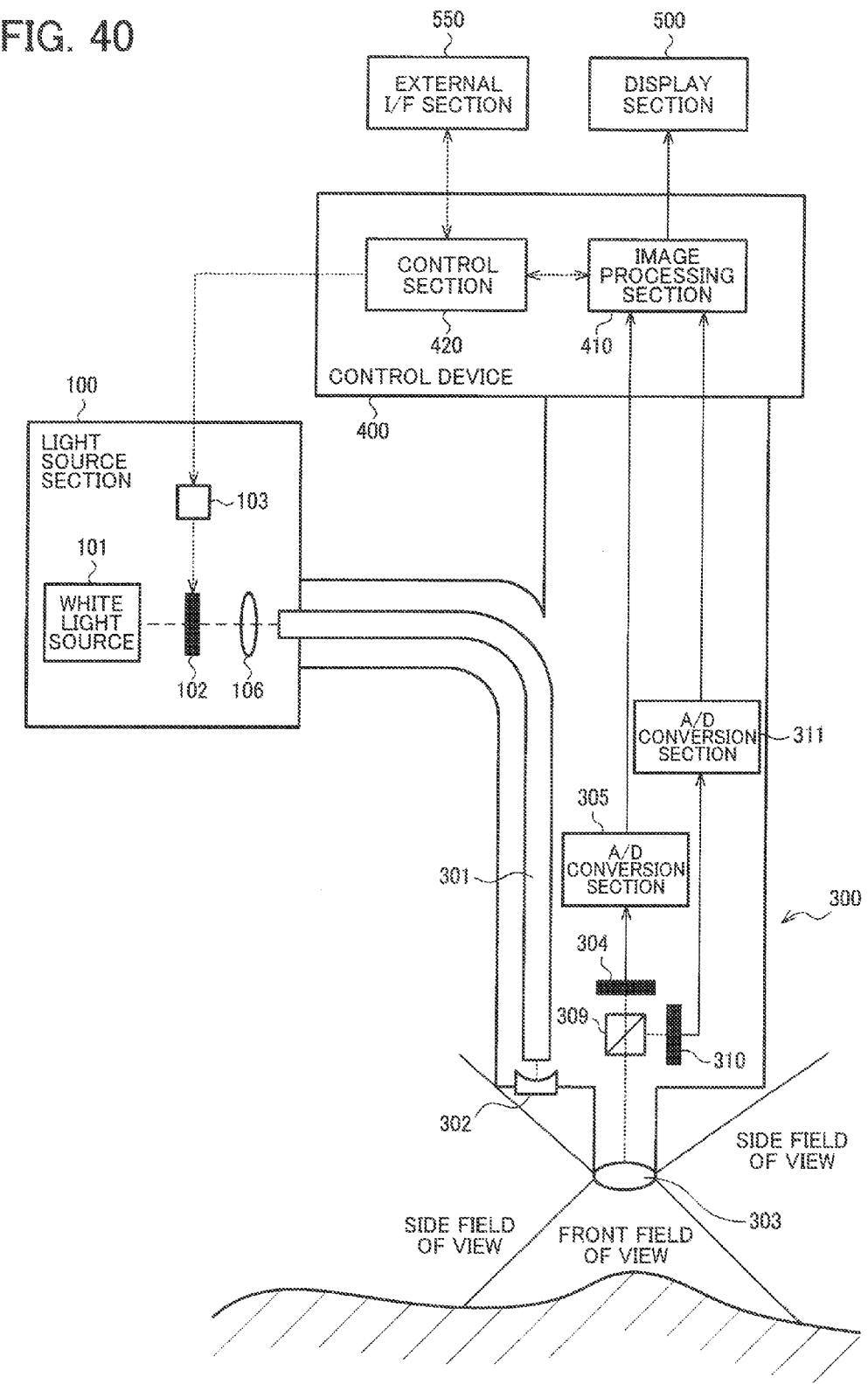
FIG. 40 illustrates a configuration example of an endoscope system according to a sixth embodiment.

FIG. 40 illustrates a configuration example of an endoscope system according to the sixth embodiment. The endoscope system includes a light source section 100, an insertion section 300, a control device 400, a display section 500, and an external I/F section 550. Note that the same elements as those described above with reference to FIG. 3 and the like are indicated by identical reference signs, and description of these elements is appropriately omitted.

The light source section 100 includes a white light source 101, a light source aperture 102, a light source aperture driver section 103, and a condenser lens 106. The light source section 100 according to the sixth embodiment differs from the light source section 100 according to the first embodiment in that the rotary color filter 104 and the rotation driver section 105 are omitted.

The insertion section 300 includes a light guide fiber 301, an illumination lens 302, and an objective optical system 303. The insertion section 300 also includes a half mirror 309 that separates the reflected light focused by the objective optical system 303 into two parts, a first image sensor 304 and a second image sensor 310 that respectively detect the separated reflected lights, a first A/D conversion section 305, and a second A/D conversion section 311.

The A/D conversion section 311 converts analog image signals detected by the second image sensor 310 into digital image signals.

Figures 41, 42:
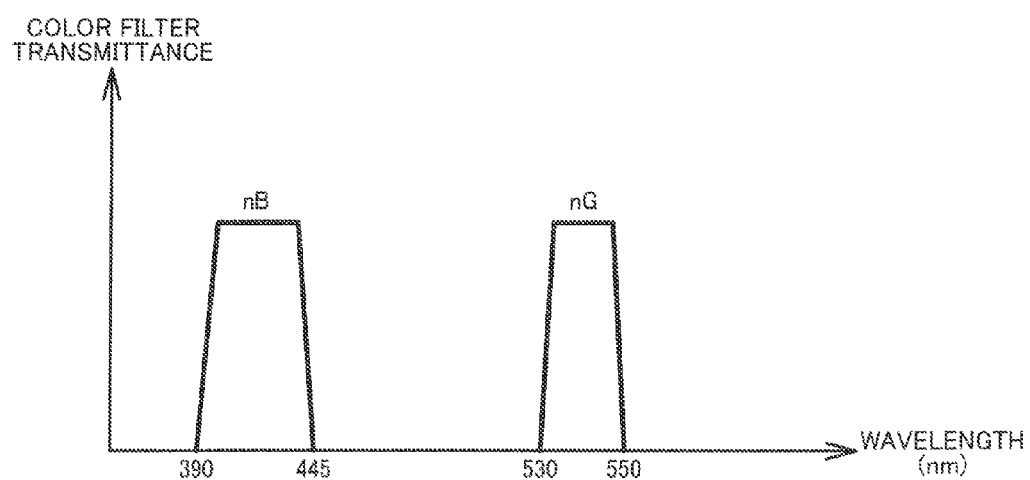
FIG. 41 illustrates a configuration example of a color filter of a second image sensor.
FIG. 42 illustrates an example of the transmittance characteristics of a color filter of a second image sensor.

The first image sensor 304 is a Bayer array image sensor. The second image sensor 310 is an image sensor in which color filters nB and nG are disposed in a staggered arrangement (see FIG. 41). As illustrated in FIG. 42, the color filters nB and nG have characteristics that allow narrow-band light to pass through. For example, the color filter nB has characteristics that allow light having a wavelength of 390 to 445 nm to pass through, and the color filter nG has characteristics that allow light having a wavelength of 530 to 550 nm to pass through. The first image sensor 304 and the second image sensor 310 have an identical pixel count, for example.

The control device 400 includes an image processing section 410 and a control section 420. The A/D conversion sections 305 and 311 output the digital image signals to the image processing section 410. The image processing section 410 processes the image signals, and transmits the processed image signals to the display section 500. The control section 420 is connected to the light source aperture driver section 103, the image processing section 410, and the external I/F section 550, and controls the light source aperture driver section 103, the image processing section 410, and the external OF section 550.

7.2. Image Processing Section

Figure 43:
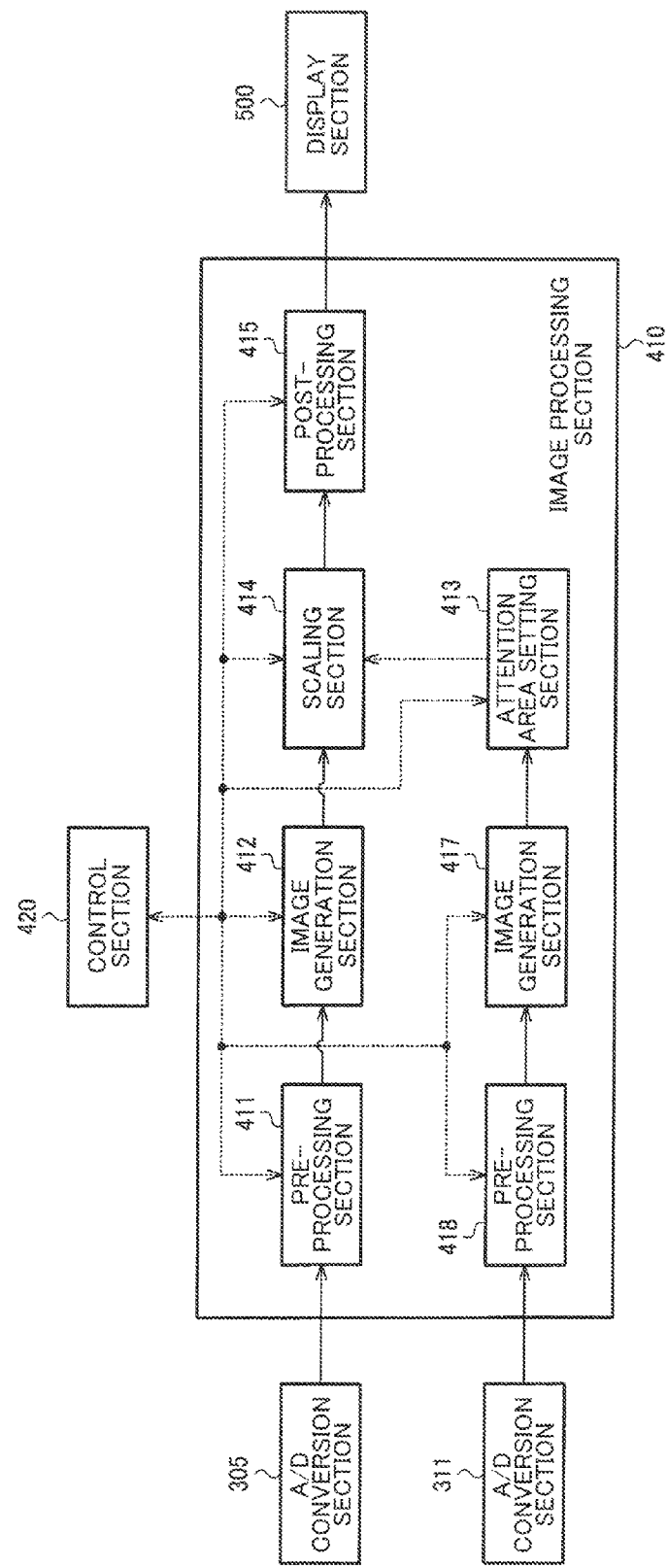
FIG. 43 illustrates a detailed configuration example of an image processing section according to the sixth embodiment.

FIG. 43 illustrates a detailed configuration example of the image processing section 410 according to the sixth embodiment. The image processing section 410 includes a first preprocessing section 411, a second preprocessing section 418, a first image generation section 412, a second image generation section 417, an attention area setting section 413, a scaling section 414, and a post-processing section 415. Note that the processes performed by the preprocessing section 411, the scaling section 414, and the post-processing section 415 are the same as described above in connection with the first embodiment. Therefore, description thereof is omitted.

The image generation section 412 is connected to the scaling section 414. The preprocessing section 418 is connected to the image generation section 417. The image generation section 417 is connected to the attention area setting section 413. The control section 420 is bidirectionally connected to the preprocessing section 418 and the image generation section 417, and controls the preprocessing section 418 and the image generation section 417.

The image generation section 412 performs an image generation process on the image signals processed by the preprocessing section 411. The image signals acquired by the first image sensor 304 are Bayer array image signals. The image generation section 412 generates R, G, and B image signals from the Bayer array image signals using an interpolation process. For example, a known bicubic interpolation process may be used as the interpolation process. The image signals output from the image generation section 412 are hereinafter referred to as "normal light image".

The preprocessing section 418 performs an OB clamp process, a gain control process, and a WB correction process on the image signals input from the A/D conversion section 311 using an OB clamp value, a gain correction value, and a WB coefficient stored in the control section 420. The preprocessing section 418 transmits the resulting image signals to the image generation section 417.

The image generation section 417 performs the image generation process on the image signals processed by the preprocessing section 418. As illustrated in FIG. 41, the second image sensor 310 is an image sensor in which the color filters nB and nG are disposed in a staggered arrangement. Therefore, the image signals processed by the preprocessing section 418 are G and B image signals as illustrated in FIG. 44. In FIG. 44, the image signals acquired by the color filters nB are indicated by B2, and the image signals acquired by the color filters nG are indicated by G2.

The image generation section 417 generates B2 image signals and G2 image signals from the G and B image signals illustrated in FIG. 44 using the following expressions (15) and (16). The B2 image signals are image signals in which each pixel has the B2 signal, and the G2 image signals are image signals in which each pixel has the G2 signal. For example, the image signal B2(1, 1) acquired by the nB filter at the position G2(1, 1) in FIG. 44 is calculated using the expression (15). The image signal G2(1, 2) acquired by the nG filter at the position B2(1, 2) in FIG. 44 is calculated using the expression (16).

$$B2(1,1)=\{B2(0,1)+B2(1,0)+B2(1,2)+B2(2,1)\}/4 \quad (15)$$

$$G2(1,2)=\{G2(0,2)+G2(1,1)+G2(1,3)+G2(2,2)\}/4 \quad (16)$$

The image generation section 417 generates R, G, and B image signals using the B2 image signals and the G2 image signals generated using the expressions (15) and (16). Specifically, the image generation section 417 generates R, G, and B image signals using the G2 image signals as R image signals, and using the B2 image signals as G and B image signals. The image signals output from the image generation section 417 are hereinafter referred to as "narrow-band light image" (special light image in a broad sense).

The attention area setting section 413 detects a lesion area from the narrow-band light image using the method described later, and sets the attention area based on the detected lesion area. The narrow-band light image is characterized in that a lesion area such as epidermoid cancer is drawn as a brown area. Therefore, a lesion area can be detected by detecting an area (brown area) having a specific hue from the narrow-band light image.

The scaling section 414 enlarges an area within the normal light image that corresponds to the set attention area. The attention area is an area within a circle that is formed around the coordinates $(x_0, y_0)$ and has a radius R (described later). The coordinate scaling process is performed in the same manner as in the first embodiment.

7.3. Attention Area Setting Section

Figure 45:
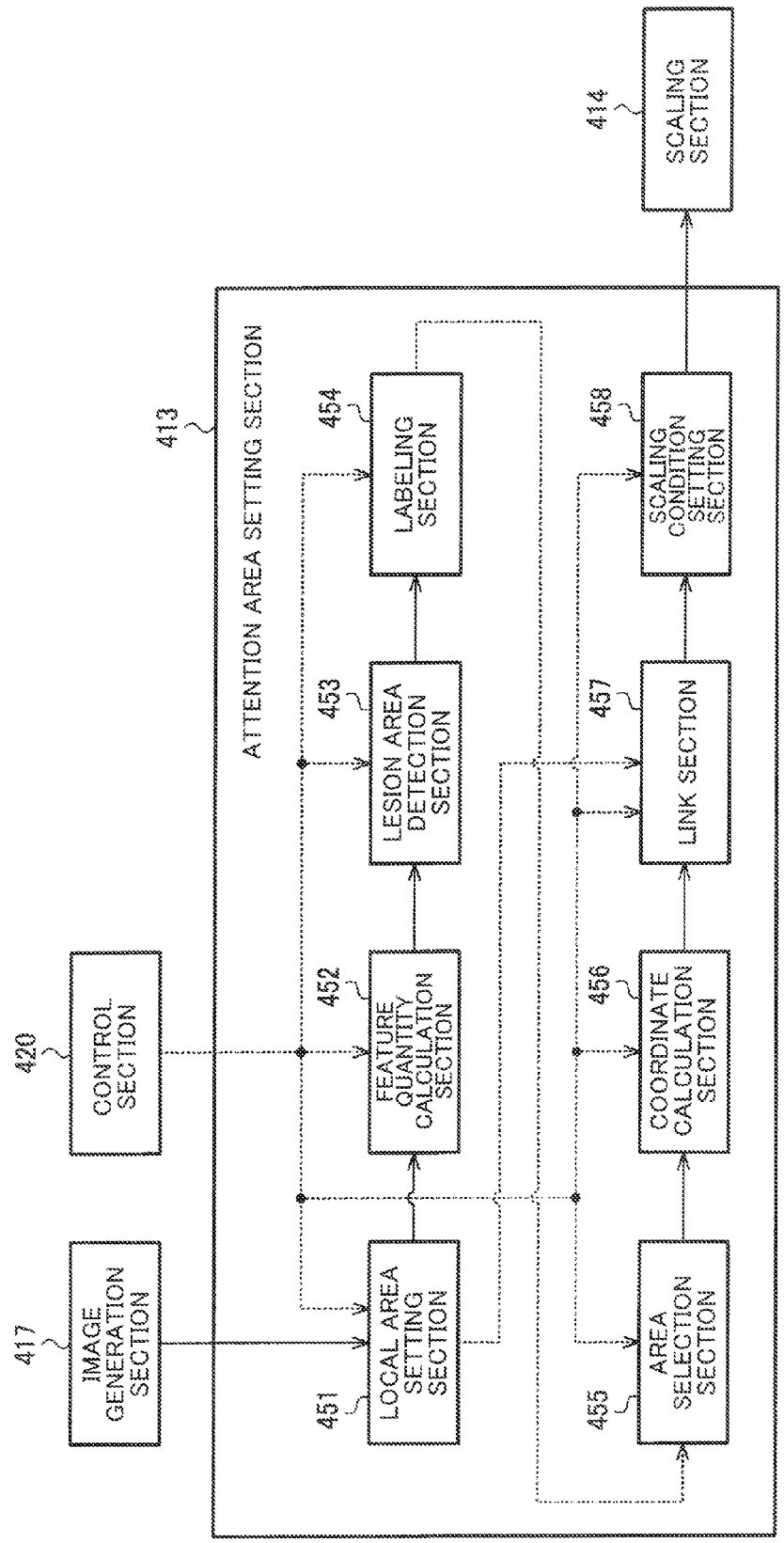
FIG. 45 illustrates a detailed configuration example of an attention area setting section according to the sixth embodiment.

FIG. 45 illustrates a detailed configuration example of the attention area setting section 413 according to the sixth embodiment. The attention area setting section 413 includes a local area setting section 451, a feature quantity calculation section 452, a lesion area detection section 453, a labeling section 454, an area selection section 455, a coordinate calculation section 456, a link section 457, and a scaling condition setting section 458.

The image generation section 417 is connected to the local area setting section 451. The local area setting section 451 is connected to the feature quantity calculation section 452 and the link section 457. The feature quantity calculation section 452 is connected to the lesion area detection section 453. The lesion area detection section 453 is connected to the labeling section 454. The labeling section 454 is connected to the area selection section 455. The area selection section 455 is connected to the coordinate calculation section 456. The coordinate calculation section 456 is connected to the link section 457. The link section 457 is connected to the scaling condition setting section 458. The scaling condition setting section 458 is connected to the scaling section 414.

The local area setting section 451 sets a plurality of local areas within the narrow-band light image output from the image generation section 417. The following description is given taking an example in which the local area setting section 451 divides the narrow-band light image into a plurality of rectangular areas, and sets the plurality of rectangular areas to be the local areas.

Figure 46:
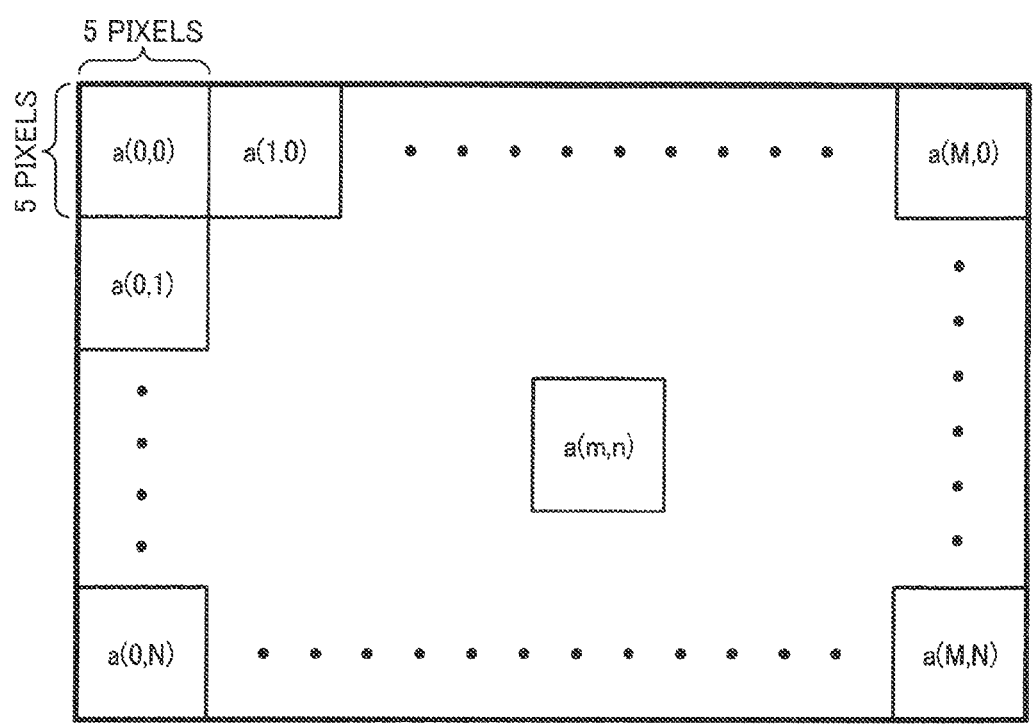
FIG. 46 illustrates a local area setting example.

As illustrated in FIG. 46, each local area includes 5×5 pixels, for example. The narrow-band light image signals includes M×N local areas, and the coordinates of each local area are indicated by (m, n). The local area positioned at the coordinates (m, n) is indicated by a(m, n). The coordinates of the local area positioned at the upper left of the image are indicated by (0, 0). The rightward direction is defined as the positive direction of the coordinate value m, and the downward direction is defined as the positive direction of the coordinate value n. An area that includes a plurality of adjacent pixels is set to be the local area in order to reduce the amount of calculations. Note that one pixel may be set to be the local area. In this case, the subsequent process is performed in the same manner as in the case where each local area includes a plurality of adjacent pixels.

The local area setting section 451 outputs information about the size of the local area and the coordinates of each local area to the feature quantity calculation section 452. The local area setting section 451 outputs information about the coordinates of each local area and the coordinates within the narrow-band light image that correspond to the coordinates of each local area to the link section 457. Note that the coordinates within the narrow-band light image that correspond to the coordinates of each local area refer to the coordinates of the pixel positioned at the center of each local area.

The feature quantity calculation section 452 calculates the feature quantity from each local area set by the local area setting section 451. The following description illustrates an example in which hue is used as the feature quantity.

The hue of the local area a(m, n) is indicated by H(m, n). When calculating the hue H(m, n), the feature quantity calculation section 452 calculates the average values R_ave, G_ave, and B_ave of the R, G, and B signals in each local area. The average value R_ave is the average value of the R signals of the pixels included in each local area. This also applies to the average values G_ave and B_ave. Each signal value is indicated by 8 bits (0 to 255), for example.

The feature quantity calculation section 452 calculates the hue H(m, n) of each local area from the average values R_ave, G_ave, and B_ave using the following expressions (17) to (22), for example. Specifically, the value max is calculated using the expression (17).

$$\mathrm{max}=\mathrm{MAX}(R\_ave, G\_ave, B\_ave) \quad (17)$$

MAX( ) is a function that outputs the maximum argument among a plurality of arguments in parentheses.

When the value max is 0, the hue H is calculated using the expression (18).

$$H=0 \quad (18)$$

When the value max is not 0, the value d is calculated using the expression (19).

$$d=\mathrm{MAX}(R\_ave, G\_ave, B\_ave)-\mathrm{MIN}(R\_ave, G\_ave, B\_ave) \quad (19)$$

MIN( ) is a function that outputs the minimum argument among a plurality of arguments in parentheses.

When the average value R_ave among the average values R_ave, G_ave, and B_ave is a maximum, the hue H is calculated using the expression (20).

$$H=60\times(G\_ave-B\_ave)\div d \quad (20)$$

When the average value G_ave among the average values R_ave, G_ave, and B_ave is a maximum, the hue H is calculated using the expression (21).

$$H=60\times\{2+(B\_ave-R\_ave)\}\div d \quad (21)$$

When the average value B_ave among the average values R_ave, G_ave, and B_ave is a maximum, the hue H is calculated using the expression (22).

$$H=60\times\{4+(R\_ave-G\_ave)\}\div d \quad (22)$$

When H<0, 360 is added to the hue H. The hue H is set to 0 when the hue H is 360.

The lesion area detection section 453 detects the local area having a specific hue H as a lesion area, and outputs the coordinates of each local area detected as the lesion area to the labeling section 454. For example, the lesion area detection section 453 detects an area having a hue H of 5 to 35 (corresponding to a brown area) as the lesion area.

The labeling section 454 assigns an identical label to adjacent lesion areas among the lesion areas output from the lesion area detection section 453. A set of lesion areas to which an identical label is assigned is hereinafter referred to as "lesion area group". The labeling section 454 calculates the size of the lesion area group to which an identical label is assigned. The size of the lesion area group may be the number of lesion areas to which an identical label is assigned. Note that the information about the size of the lesion area group is not limited thereto. It suffices that the information about the size of the lesion area group be information that indicates the area of the lesion area group.

Figure 47:
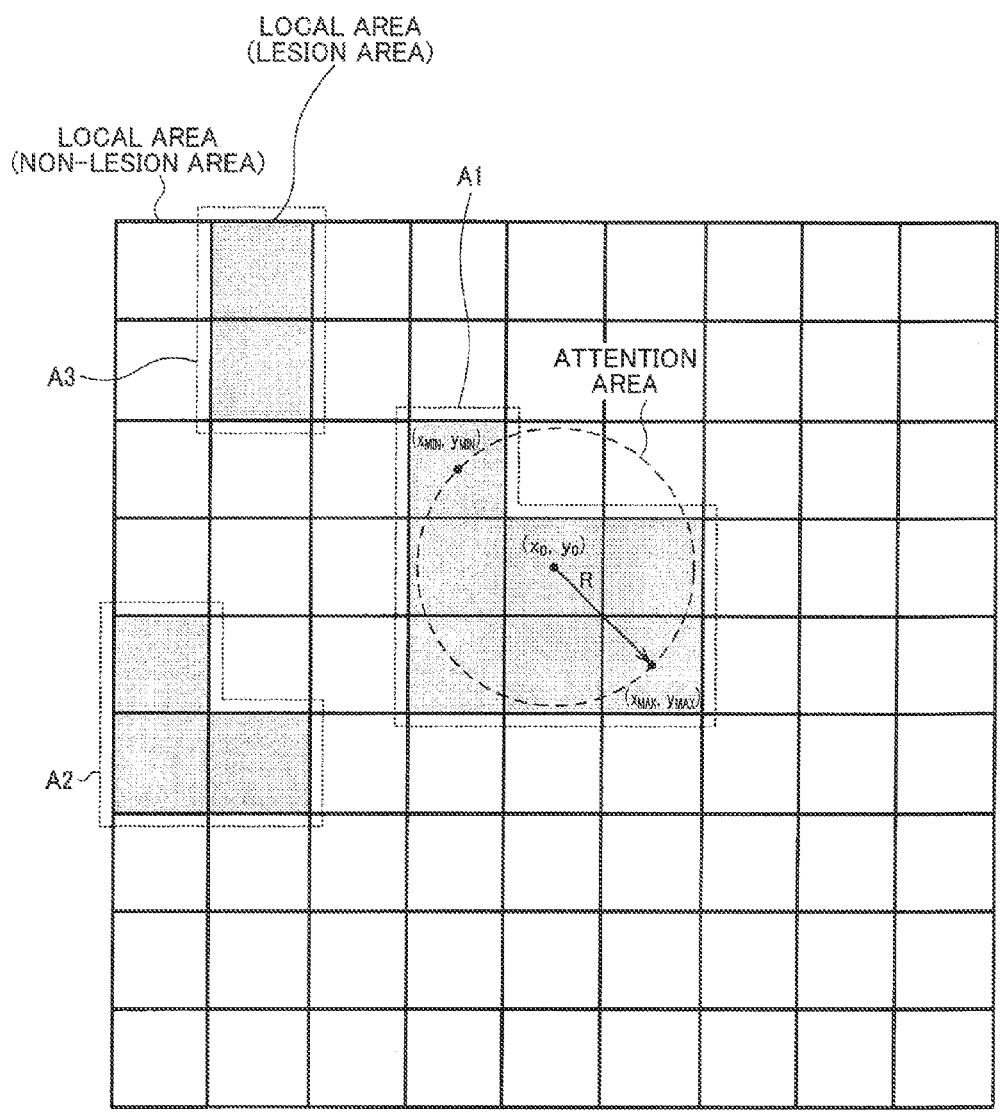
FIG. 47 is a view illustrating a process performed by an attention area setting section according to the sixth embodiment.

The process performed by the labeling section 454 is described in detail below with reference to FIG. 47. For example, when lesion areas have been detected as illustrated in FIG. 47, a label 1 is assigned to the lesion areas that belong to the area indicated by A1. Likewise, a label 2 is assigned to the lesion areas that belong to the area indicated by A2, and a label 3 is assigned to the lesion areas that belong to the area indicated by A3. The labeling section 454 calculates the size of the lesion area group to which an identical label is assigned. The size of the lesion area group 1 (A1) to which the label 1 is assigned is calculated to be 7. The size of the lesion area group 2 (A2) is calculated to be 3, and the size of the lesion area group 3 (A3) is calculated to be 2.

The area selection section 455 selects the lesion area group having the largest size from the plurality of lesion area groups to which the label is assigned by the labeling section 454, and determines the selected lesion area group to be the attention area. The area selection section 455 outputs the coordinates of each local area included in the attention area to the coordinate calculation section 456. In the example illustrated in FIG. 47, the lesion area group 1 indicated by A1 is selected to be the attention area.

The coordinate calculation section 456 calculates the maximum value ($m_{MAX}$, $n_{MAX}$) and the minimum value ($m_{MIN}$, $n_{MIN}$) of the coordinates of the local areas from the coordinates of each local area output from the area selection section 455, and outputs the calculated values to the link section 457.

When the number of local areas output from the area selection section 455 is K, and the local areas output from the area selection section 455 are indicated by $a(m_1, n_1)$ to $a(m_K, n_K)$, the coordinate calculation section 456 calculates the maximum value ($m_{MAX}$, $n_{MAX}$) and the minimum value ($m_{MIN}$, $n_{MIN}$) of the coordinates of the local areas using the expression (23).

$$m_{MAX} = \mathrm{MAX}(m_1, m_2, \ldots m_K),$$

$$m_{MIN} = \mathrm{MIN}(m_1, m_2, \ldots m_K),$$

$$n_{MAX} = \mathrm{MAX}(n_1, n_2, \ldots n_K),$$

$$n_{MIN} = \mathrm{MIN}(n_1, n_2, \ldots n_K) \quad (23)$$

The link section 457 calculates the coordinates within the narrow-band light image that correspond to the maximum value ($m_{MAX}$, $n_{MAX}$) and the minimum value ($m_{MIN}$, $n_{MIN}$). Specifically, the link section 457 calculates the coordinates within the narrow-band light image that correspond to the maximum value ($m_{MAX}$, $n_{MAX}$) and the minimum value ($m_{MIN}$, $n_{MIN}$) based on the relationship between the coordinates of the local areas output from the local area setting section 451 and the coordinates within the narrow-band light image. The coordinates within the narrow-band light image that correspond to the maximum value ($m_{MAX}$, $n_{MAX}$) and the minimum value ($m_{MIN}$, $n_{MIN}$) are indicated by ($x_{MAX}$, $y_{MAX}$) and ($x_{MIN}$, $y_{MIN}$). The link section 457 outputs the coordinates ($x_{MAX}$, $y_{MAX}$) and ($x_{MIN}$, $y_{MIN}$) to the scaling condition setting section 458.

The scaling condition setting section 458 determines scaling conditions (i.e., conditions for the attention area that is to be subjected to the scaling process), and outputs the determined scaling conditions to the scaling section 414. Specifically, the scaling condition setting section 458 calculates the center coordinates ($x_0$, $y_0$) of the attention area using the following expression (24), calculates the radius R of the attention area using the following expression (25), and determines the calculated center coordinates ($x_0$, $y_0$) and radius R to be the scaling conditions. In the example illustrated in FIG. 47, an area enclosed by the circle having the radius R is set to be the scaling target attention area.

$$x_0 = \mathrm{int}\{(x_{MAX} + x_{MIN})/2\},$$

$$y_0 = \mathrm{int}\{(y_{MAX} + y_{MIN})/2\} \quad (24)$$

$$R = \sqrt{\{(x_{MAX} - x_{MIN})/2\}^2 + \{(y_{MAX} - y_{MIN})/2\}^2} \quad (25)$$

where, int( ) is a function that returns an integer of a real number in parentheses.

7.4. Software

In the sixth embodiment, some or all of the processes performed by each section of the image processing section 410 may be implemented by software. In this case, a CPU of a computer system (described later with reference to FIG. 72, for example) executes an image processing program.

Figure 48:
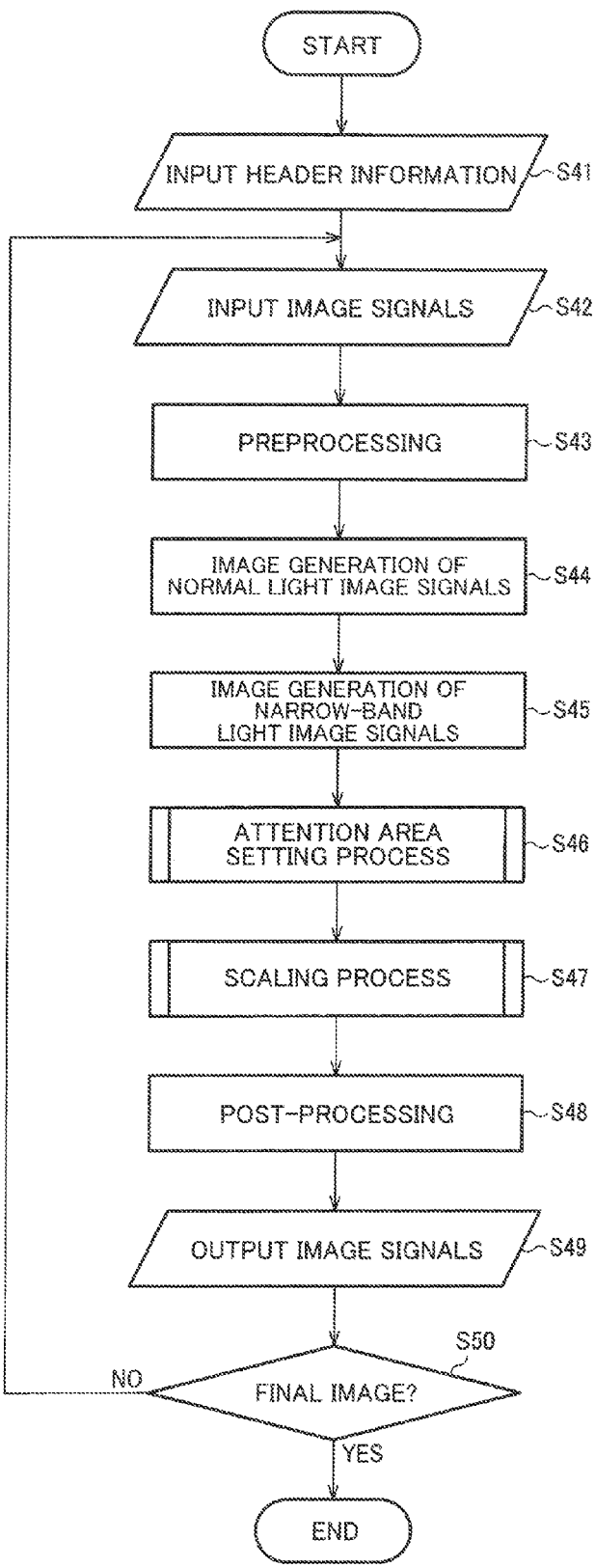
FIG. 48 illustrates an example of a flowchart of an image processing program according to the sixth embodiment.

FIG. 48 illustrates an example of a detailed flowchart of the image processing program according to the sixth embodiment. As illustrated in FIG. 48, the header information is input (S41), and two types of image signals are input to an image buffer allocated in advance (S42). The two types of image signals include the image signals detected by the image sensor having a Bayer array, and the image signals detected by the image sensor having the array illustrated in FIG. 41.

The image signals are subjected to preprocessing (S43). The interpolation process is performed on the image signals detected by the image sensor having a Bayer array to generate R, and B image signals as the normal light image (S44). R, G, and B image signals are generated from the image signals detected by the image sensor having the array illustrated in FIG. 41 using the above method to generate a narrow-band light image (S45).

The attention area is set based on the narrow-band light image (S46). The scaling process is performed on the normal light image based on the attention area (S47). The details of the attention area setting process are described below. The scaling process is performed in the same manner as described above with reference to FIG. 20. The normal light image subjected to the scaling process is subjected to post-processing (S48), and then output (S49). When the final image has been output, the process is terminated (S50, Yes). When the final image has not been output, the process in the step S42 is performed (S50, No).

Note that the processes other than the image signal input process (S42), the normal light image generating process (S44), the narrow-band light image generating process (S45), and the attention area setting process (S46) are performed in the same manner as in the first embodiment.

Figure 49:
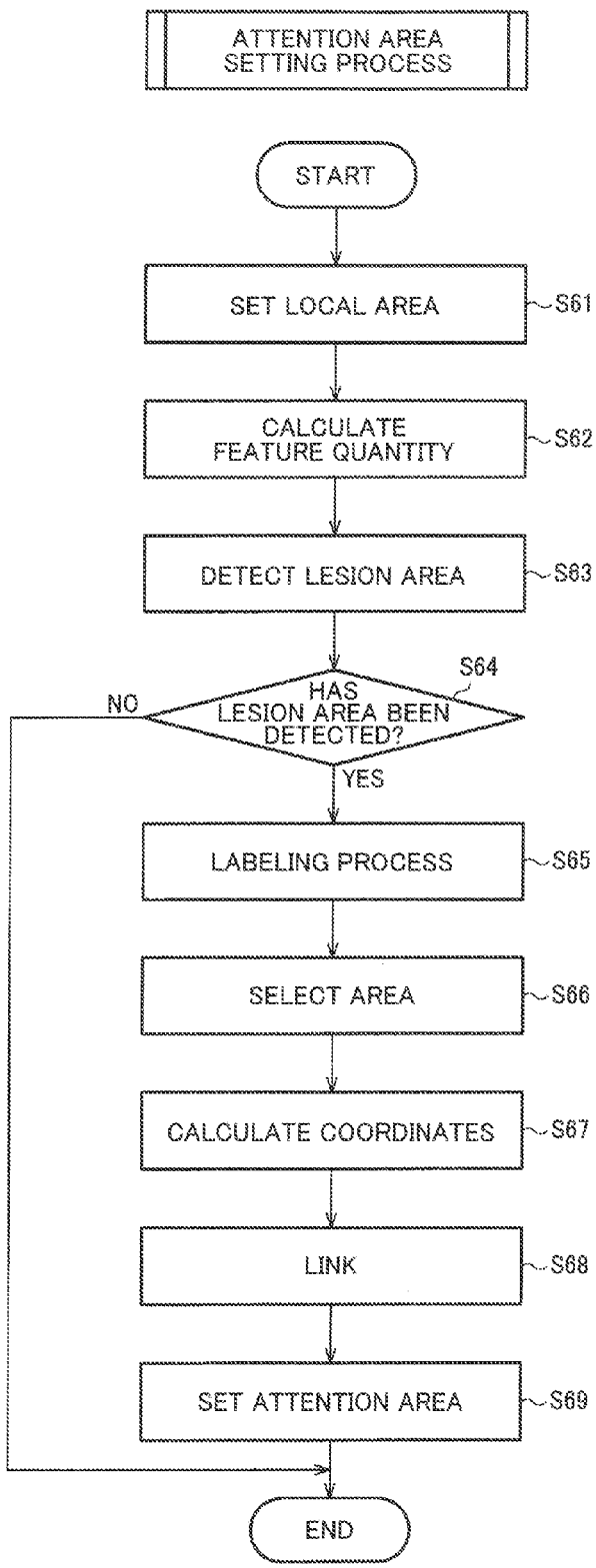
FIG. 49 illustrates an example of a detailed flowchart of an attention area setting process according to the sixth embodiment.

FIG. 49 illustrates an example of a detailed flowchart of the attention area setting process (S46) according to the sixth embodiment. The following description illustrates an example in which the attention area setting process is performed on the narrow-band light image.

As illustrated in FIG. 49, the local areas (see FIG. 46) are set within the narrow-band light image (S61). The feature quantity (hue H) of each local area is calculated by the above method (S62). A local area having a hue H of 5 to 35 is detected to be a lesion area (S63). Whether or not a lesion area has been detected in the step S63 is determined (S64). When it has been determined that a lesion area has not been detected in the step S63, the process is terminated (S64, No).

When it has been determined that a lesion area has been detected in the step S63 (S64, Yes), the labeling process is performed on the detected lesion area (S65). A lesion area group having the largest size is selected (S66). The maximum value ($m_{MAX}$, $n_{MAX}$) and the minimum value ($m_{MIN}$, $n_{MIN}$) of the local area coordinates are calculated from the coordinates of each local area included in the selected lesion area group using the above method (S67). The coordinates ($x_{MAX}$, $y_{MAX}$) and ($x_{MIN}$, $y_{MIN}$) within the narrow-band light image that correspond to the maximum value ($m_{MAX}$, $n_{MAX}$) and the minimum value ($m_{MIN}$, $n_{MIN}$) are calculated (S68). The center coordinates ($x_0$, $y_0$) of the attention area and the radius R are calculated based on the coordinates ($x_{MAX}$, $y_{MAX}$) and ($x_{MIN}$, $y_{MIN}$) (S69), and the process is terminated.

According to the sixth embodiment, the attention area setting section 413 calculates the feature quantity (e.g., hue value) based on the captured image, and sets the attention area based on an area having a given feature quantity (e.g., an area that has a hue value of 5 to 35).

The above configuration makes it possible to set the attention area based on the feature quantity of the image that is characteristic of a lesion area, and enlarge the attention area by performing the scaling process. This makes it possible to provide the operator with an image in which the lesion area is appropriately enlarged.

The attention area setting section 413 may select an area having the largest area from a plurality of areas having the given feature quantity, and may set a circular area that includes the selected area to be the attention area (see FIG. 47 and the like).

Since the operator brings the scope close to the observation target lesion area, it is considered that the observation target lesion area is displayed to have a large size. Therefore, it is possible to appropriately enlarge the area that is considered to attract the operator's attention by setting the lesion area group having the largest size to be the attention area.

Although the sixth embodiment has been described above taking an example in which the feature quantity is the hue value, the configuration according to the sixth embodiment is not limited thereto. It suffices that the feature quantity allow discrimination between a lesion area and another area. For example, the R pixel value may be used as the feature quantity when determining a bleeding site.

Although the sixth embodiment has been described above taking an example in which the attention area is set based on the lesion area group (among the lesion area groups to which the label is assigned by the labeling section 454) that has the largest size, the configuration according to the sixth embodiment is not limited thereto. For example, the attention area may be set based on all of the lesion areas detected by the lesion area detection section 453. In this case, the area selection section 455 outputs the coordinates of the local areas included in all of the lesion area groups output from the labeling section 454 to the coordinate calculation section 456.

The above configuration makes it possible to relatively enlarge a plurality of lesion area groups when a plurality of lesion area groups are present.

Although the sixth embodiment has been described above taking an example in which the normal light image is used as the display image, the configuration according to the sixth embodiment is not limited thereto. For example, the narrow-band light image may be used as the display image.

The captured image may be a special light image in which an object image having information within a specific wavelength band is captured, and a normal light image (white light image) in which an object image having information within the wavelength band of white light is captured. The attention area setting section 413 may set the attention area based on the special light image.

The scaling section 414 may perform the scaling process on the normal light image based on the attention area set by the attention area setting section 413.

The above configuration makes it possible to easily extract the feature quantity of the lesion area by acquiring the special light image that corresponds to the detection target lesion area, and set the attention area based on the extracted feature quantity. It is also possible to perform the scaling process on the normal light image (that is normally used for observation) corresponding to the attention area set using the special light image.

The specific wavelength band may be a band that is narrower than the wavelength band (e.g., 380 to 650 nm) of white light (i.e., narrow-band imaging (NBI)). The normal light image and the special light image may be an in vivo image, and the specific wavelength band included in the in vivo image may be the wavelength band of light absorbed by hemoglobin in blood, for example. The wavelength band of light absorbed by hemoglobin may be 390 to 445 nm (first narrow-band light nB) or 530 to 550 nm (second narrow-band light nG), for example.

This makes it possible to observe the surface area of tissue and the structure of blood vessels situated in a deep area. A lesion area (e.g., epidermoid cancer) that is difficult to observe using normal light can be displayed as a brown area or the like by inputting the resulting signals to given channels (G2→R, B2→G and B), so that the lesion area can be reliably detected (i.e., a situation in which the lesion area is missed can be prevented). Note that the wavelength band of 390 to 445 nm or 530 to 550 nm is selected from the viewpoint of absorption by hemoglobin and the ability to reach the surface area or the deep area of tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach the surface area or the deep area of tissue).

The normal light image and the special light image may be an in vivo image, and the specific wavelength band included in the in vivo image may be the wavelength band of fluorescence emitted from a fluorescent substance. For example, the specific wavelength band may be 490 to 625 nm This makes it possible to implement autofluorescence imaging (AFI). Intrinsic fluorescence (490 to 625 nm) emitted from a fluorescent substance (e.g., collagen) can be observed by applying excitation light (390 to 470 nm). In this case, the lesion area can be highlighted in a color differing from that of a normal mucous membrane, and can be reliably detected, for example. The wavelength band of 490 to 625 nm is the wavelength band of intrinsic fluorescence emitted from a fluorescent substance (e.g., collagen) upon application of the excitation light. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudocolor image may be generated by also applying light within the wavelength band (540 to 560 nm) absorbed by hemoglobin.

The specific wavelength band included in the in vivo image may be the wavelength band of infrared light. For example, the specific wavelength band may be 790 to 820 nm or 905 to 970 nm.

This makes it possible to implement infrared imaging (IRI). Information about the blood vessels and the blood flow in the deep area of a mucous membrane that are difficult to observe visually, can be highlighted by intravenously injecting indocyanine green (ICG) (infrared marker) that easily absorbs infrared light, and applying infrared light within the above wavelength band. This makes it possible to determine the depth of cancer invasion and the therapeutic strategy, for example. The above wavelength band is selected because an infrared marker exhibits maximum absorption within the wavelength band of 790 to 820 nm, and exhibits minimum absorption within the wavelength band of 905 to 970 nm. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by the infrared marker).

The endoscope system may include a special light image acquisition section that generates the special light image based on the acquired normal light image. For example, the half mirror 309, the image sensor 310, and the A/D conversion section 311 (see FIG. 40) may be omitted, and the preprocessing section 418 and the image generation section 417 (see FIG. 43) may generate the special light image based on the normal light image as the special light image acquisition section.

Specifically, the special light image acquisition section may include a signal extraction section that extracts signals within the wavelength band of white light from the acquired normal light image. The special light image acquisition section may generate the special light image that includes signals within the specific wavelength band based on the extracted signals within the wavelength band of normal light. For example, the signal extraction section may estimate the spectral reflectivity characteristics of the object from the RGB signals of the normal light image at intervals of 10 nm, and the special light image acquisition section may integrate the estimated signal components within the specific wavelength band to generate the special light image.

More specifically, the special light image acquisition section may include a matrix data setting section that sets matrix data for calculating the signals within the specific wavelength band from the signals within the wavelength band of normal light. The special light image acquisition section may calculate the signals within the specific wavelength band from the signals within the wavelength band of white light using the matrix data set by the matrix data setting section to generate the special light image. For example, the matrix data setting section may set table data as the matrix data, the spectral characteristics of illumination light within the specific wavelength band being stored in the table data at intervals of 10 nm. The special light image acquisition section may multiply the estimated spectral reflectivity characteristics of the object by the spectral characteristics (coefficient) stored in the table data, and may perform the integration process to generate the special light image.

According to the above configuration, since the special light image can be generated based on the normal light image, it is possible to implement the system using only one light source that emits normal light and one image sensor that captures normal light. This makes it possible to reduce the size of a capsule endoscope or the size of the insertion section of a scope-type endoscope. Moreover, a reduction in cost can be achieved since the number of parts can be reduced.

8. Seventh Embodiment 8.1. Endoscope System

A seventh embodiment in which the attention area is set based on a scope ID is described below.

Figure 50:
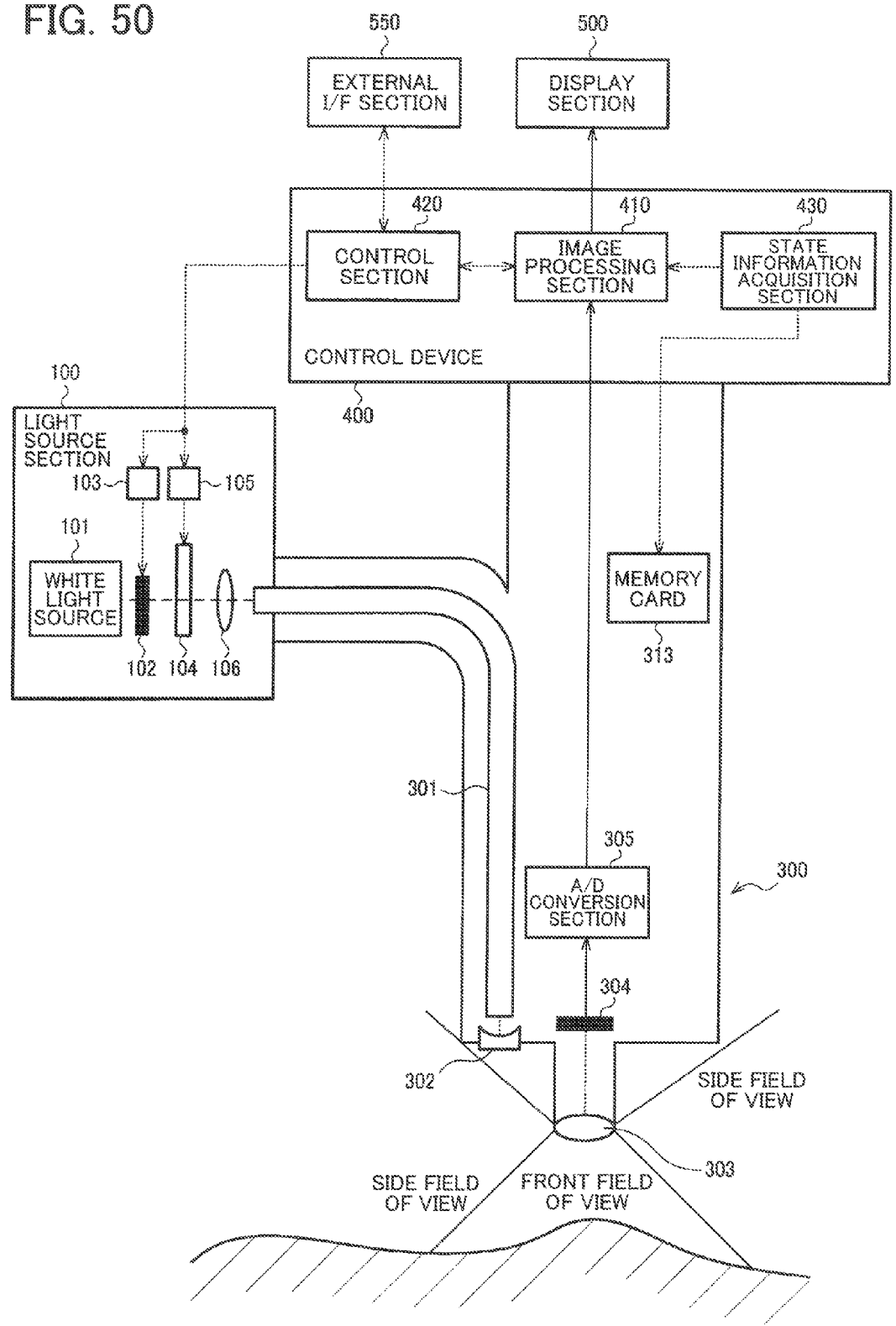
FIG. 50 illustrates a configuration example of an endoscope system according to a seventh embodiment.

FIG. 50 illustrates a configuration example of an endoscope system according to the seventh embodiment. The endoscope system includes a light source section 100, an insertion section 300, a control device 400, a display section 500, and an external I/F section 550. Note that the same elements as those described above with reference to FIG. 3 and the like are indicated by identical reference signs, and description of these elements is appropriately omitted.

The insertion section 300 includes a light guide fiber 301, an illumination lens 302, an objective optical system 303, an image sensor 304, an A/D conversion section 305, and a memory 313. Note that the configuration of each section other than the memory 313 is the same as described above in connection with the first embodiment, and description thereof is omitted.

The insertion section 300 is generally referred to as "scope". Therefore, the insertion section 300 is hereinafter appropriately referred to as "scope". A different scope is used for endoscopic diagnosis depending on the diagnosis target site. For example, an upper gastrointestinal scope is used for the diagnosis of a gullet or a stomach, and a lower gastrointestinal scope is used for the diagnosis of a large intestine. An identification number (scope ID) of each scope is stored in the memory 313 included in the scope.

The control device 400 includes an image processing section 410, a control section 420, and a state information acquisition section 430. The state information acquisition section 430 determines the type of the connected scope referring to the identification number of each scope stored in the memory 313. Note that the scope is either an upper gastrointestinal scope or a lower gastrointestinal scope, for example. The state information acquisition section 430 outputs the determined type of the connected scope to an attention area setting section 413.

8.2. Image Processing Section

Figure 51:
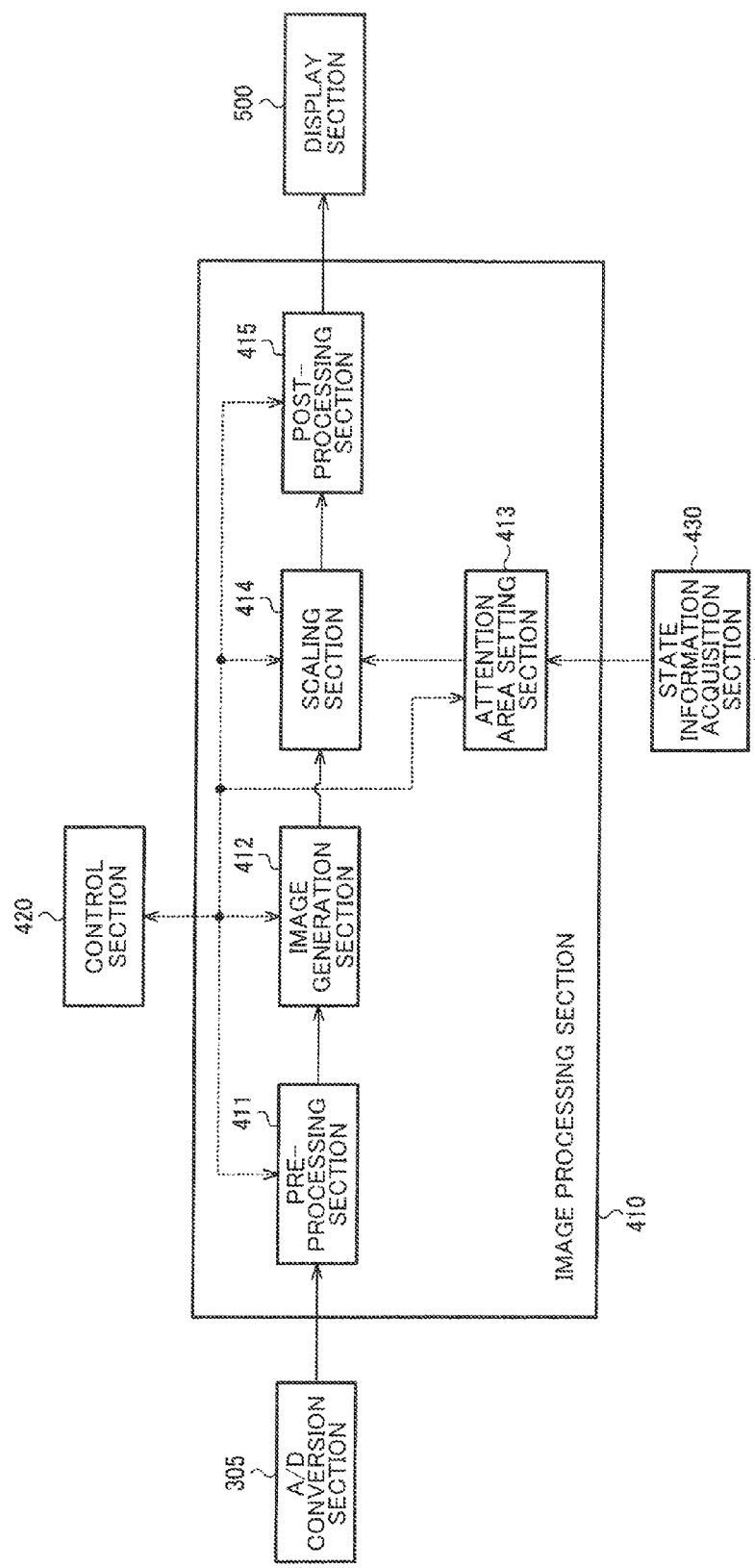
FIG. 51 illustrates a detailed configuration example of an image processing section according to the seventh embodiment.

FIG. 51 illustrates a detailed configuration example of the image processing section 410 according to the seventh embodiment. The image processing section 410 includes a preprocessing section 411, an image generation section 412, an attention area setting section 413, a scaling section 414, and a post-processing section 415. Note that the process performed by each section other than the attention area setting section 413 and the scaling section 414 is the same as described above in connection with the first embodiment, and description thereof is omitted.

The attention area setting section 413 sets the attention area corresponding to the type of scope output from the state information acquisition section 430. The attention area is set in the same manner as in the third embodiment. Specifically, when the scope is the lower gastrointestinal scope, an area within the side field of view is set to be the attention area (enlargement target area). When the scope is the upper gastrointestinal scope, an area within the front field of view is set to be the attention area.

The scaling section 414 performs the scaling process on the image in the same manner as in the third embodiment.

Specifically, the scaling section 414 enlarges the attention area while reducing the remaining area using the scaling factors A and B (see FIG. 27B). For example, a look-up table may be provided in advance that links the type of scope and the scaling factors A and B.

According to the seventh embodiment, the scope (insertion section 300) can be removably attached to the endoscope system (see FIG. 50 and the like). The state information acquisition section 430 acquires identification information (scope ID) that indicates the attached scope. The attention area setting section 413 sets the attention area based on the acquired identification information.

According to the above configuration, it is possible to allow the operator to observe the lesion area at an appropriate size while observing the entire object by applying an appropriate scaling process corresponding to the connected scope.

Specifically, the scope may include an objective optical system that forms an image of the front field of view and the side field of view. The attention area setting section 413 may set an area of the captured image that corresponds to the side field of view to be the attention area when the identification information indicates a lower gastrointestinal scope.

It is considered that a lesion situated on the back side of the folds of a large intestine that is subjected to diagnosis using the lower gastrointestinal scope is displayed within the side area of the image. Therefore, a situation in which the lesion area is missed can be suppressed by enlarging an area that corresponds to the side field of view.

The attention area setting section 413 may set an area of the captured image that corresponds to the front field of view to be the attention area when the identification information indicates an upper gastrointestinal (e.g., stomach or gullet) scope.

Since a gullet and a stomach that are subjected to diagnosis using the upper gastrointestinal scope has a small number of folds, the front field of view is important for diagnosis as compared with the side field of view. Therefore, the visibility of the important field of view can be improved by enlarging an area that corresponds to the front field of view.

9. Eighth Embodiment
9.1. Attention Area Setting Section

An eighth embodiment in which the motion amount (motion information in a broad sense) of the object is calculated from the image, and the attention area is set based on the motion amount, is described below.

An endoscope system and an image processing section 410 according to the eighth embodiment are configured in the same manner as in the first embodiment (see FIGS. 3 and 6). Therefore, description thereof is appropriately omitted. An attention area setting section 413 according to the eighth embodiment differs in configuration from the attention area setting section 413 according to the first embodiment. The attention area setting section 413 according to the eighth embodiment is described in detail below.

Figure 52:
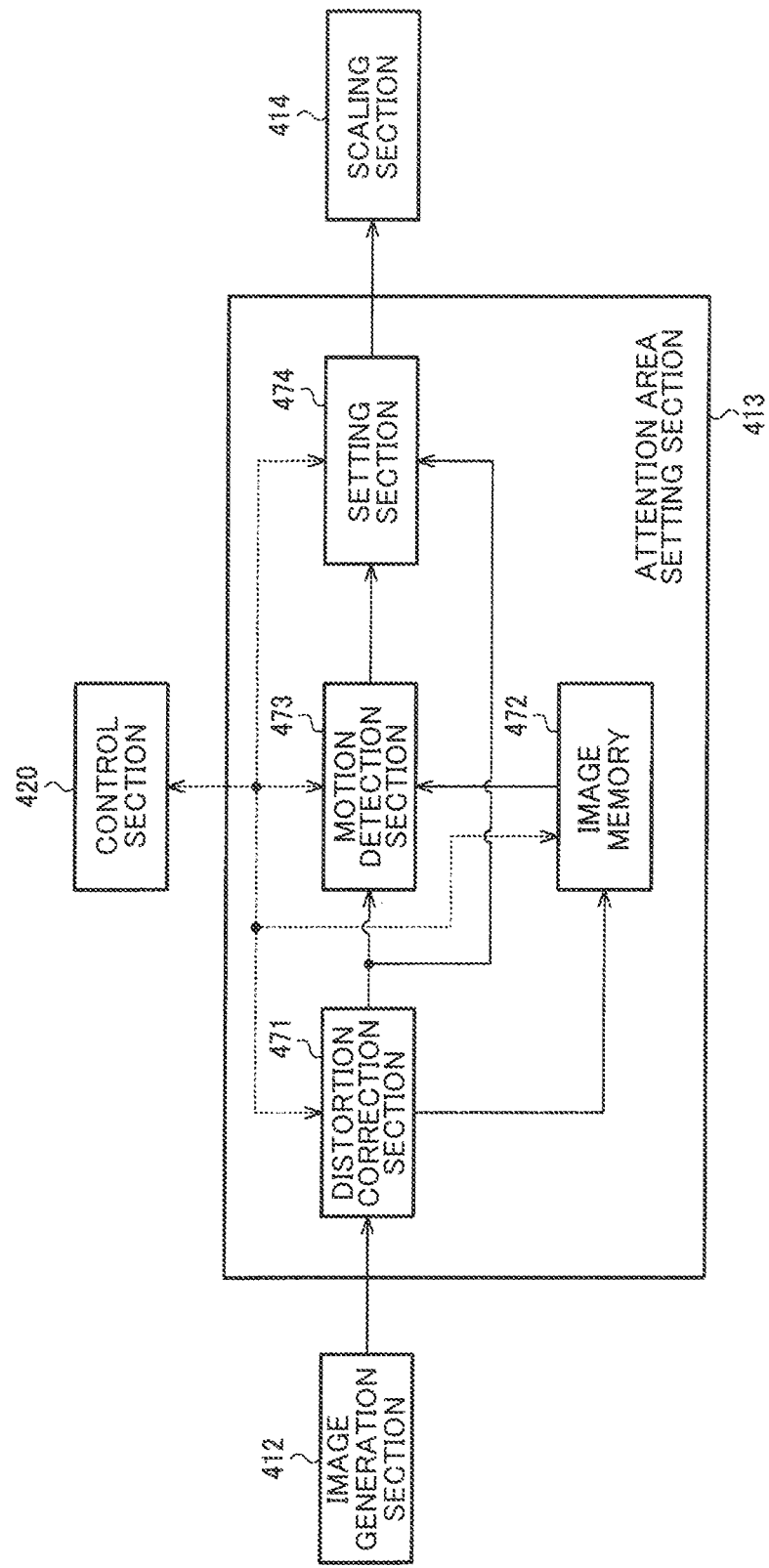
FIG. 52 illustrates a detailed configuration example of an attention area setting section according to an eighth embodiment.

FIG. 52 illustrates a detailed configuration example of the attention area setting section 413 according to the eighth embodiment. The attention area setting section 413 includes a distortion correction section 471, an image memory 472, a motion detection section 473 (motion information acquisition section in a broad sense), and a setting section 474.

The image generation section 412 outputs the image signals obtained by the image generation process to the distortion correction section 471. The distortion correction section 471 is connected to the image memory 472, the motion detection section 473, and the setting section 474. The motion detection section 473 is connected to the setting section 474. The setting section 474 is connected to the scaling section 414. The control section 420 is bidirectionally connected to the distortion correction section 471, the image memory 472, the motion detection section 473, and the setting section 474, and controls the distortion correction section 471, the image memory 472, the motion detection section 473, and the setting section 474.

Figure 53:
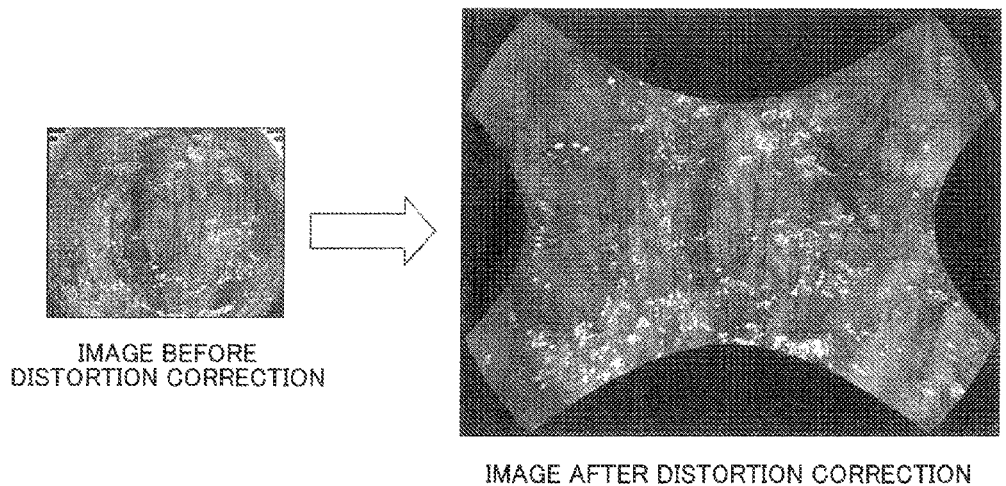
FIG. 53 illustrates an example of an image before being subjected to a distortion correction process and an image obtained by the distortion correction process.

The distortion correction section 471 performs a distortion (i.e., aberration) correction process on the image signals obtained by the image generation process. FIG. 53 illustrates an example of an image before being subjected to the distortion correction process, and an image obtained by the distortion correction process.

The distortion correction section 471 acquires the pixel coordinates of the image obtained by the distortion correction process. The size of the image obtained by the distortion correction process is acquired in advance based on the distortion of the optical system. The distortion correction section 471 transforms the acquired pixel coordinates (x, y) into coordinates (x', y') around the optical center (i.e., origin) using the following expression (26).

$$\begin{pmatrix} x' \\ y' \end{pmatrix} = \begin{pmatrix} x \\ y \end{pmatrix} - \begin{pmatrix} \text{center\_x} \\ \text{center\_y} \end{pmatrix} \quad (26)$$

where, (center_x, center_y) are the coordinates of the optical center after the distortion correction process. For example, the optical center after the distortion correction process is the center of the image obtained by the distortion correction process.

The distortion correction section 471 calculates the object height r using the following expression (27) based on the pixel coordinates (x', y').

$$r = (x'^2 + y'^2)^{1/2} / \text{max\_}r \quad (27)$$

where, max_r is the maximum object height in the image obtained by the distortion correction process.

The distortion correction section 471 then calculates the ratio (R/r) of the image height to the object height based on the calculated object height r. Specifically, the distortion correction section 471 stores the relationship between the ratio R/r and the object height r as a table, and acquires the ratio R/r that corresponds to the object height r referring to the table. The distortion correction section 471 then acquires the pixel coordinates (X, Y) before the distortion correction process that correspond to the pixel coordinates (x, y) after the distortion correction process using the following expression (28).

$$\begin{pmatrix} X \\ Y \end{pmatrix} = (R/r) \cdot \begin{pmatrix} x' \\ y' \end{pmatrix} + \begin{pmatrix} \text{center\_X} \\ \text{center\_Y} \end{pmatrix} \quad (28)$$

where, (center_X, center_Y) are the coordinates of the optical center before the distortion correction process. For example, the optical center before the distortion correction process is the center of the image before being subjected to the distortion correction process.

The distortion correction section 471 then calculates the pixel value at the pixel coordinates (x, y) after the distortion correction process based on the calculated pixel coordinates (X, Y) before the distortion correction process. When the pixel coordinates (X, Y) are not integers, the pixel value is calculated by performing a linear interpolation process based on the peripheral pixel values. The distortion correction section 471 performs the above process on each pixel of the image obtained by the distortion correction process. The distortion correction section 471 outputs the image (distortion-corrected image) of which the distortion has thus been corrected, to the image memory 472 and the motion detection section 473.

The image memory 472 stores the distortion-corrected image obtained by the distortion correction section 471. The distortion-corrected image stored in the image memory 472 is output to the motion detection section 473 in synchronization with the timing at which the subsequent distortion-corrected image is output from the distortion correction section 471.

The motion detection section 473 detects a local motion of the image based on the distortion-corrected image obtained by the distortion correction section 471 and the distortion-corrected image stored in the image memory 472. Note that the distortion-corrected image obtained by the distortion correction section 471 may be hereinafter referred to as "current frame image", and the distortion-corrected image stored in the image memory 472 may be hereinafter referred to as "preceding frame image" for convenience.

Figure 54:
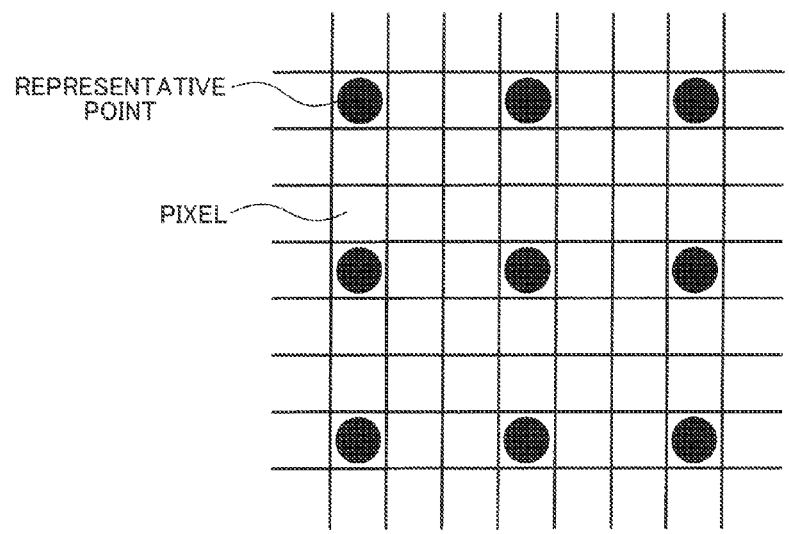
FIG. 54 illustrates a representative point setting example.

Specifically, the motion detection section 473 sets a representative point within the current frame image, the representative point being a point at which a local motion is detected. As illustrated in FIG. 54, the motion detection section 473 sets a plurality of representative points (indicated by each black circle in FIG. 54) to pixels of the current frame image in a grid-like pattern at given intervals. The motion detection section 473 calculates the motion vector between the current frame image and the preceding frame image at each representative point as the local motion amount. For example, the motion detection section 473 detects the motion vector using a known block matching technique. The motion detection section 473 outputs the coordinates of each representative point and the motion vector detected at each representative point to the setting section 474.

The setting section 474 sets the attention area based on the current frame image output from the distortion correction section 471, and the coordinates of each representative point and the motion vector at each representative point output from the motion detection section 473. Specifically, the setting section 474 determines whether or not the current state is a withdrawal state based on the current frame image and the motion vector. The setting section 474 sets the attention area within the side field of view when the current state is the withdrawal state, and sets the attention area within the front field of view when the current state is not the withdrawal state. The setting section 474 transmits information about the set attention area to the scaling section 414.

Note that the term "withdrawal state" used herein refers to a state in which the object is observed while withdrawing the endoscope after the endoscope has been inserted into the interior of a hollow tubular organ. A large intestine is observed in such a withdrawal state. Therefore, the attention area is set within the side field of view when the current state is the withdrawal state so that the back side of folds can be easily observed, and set within the front field of view when the current state is not the withdrawal state so that the endoscope can be easily operated.

9.2. Withdrawal State Determination Method

The withdrawal state determination method is described below with reference to FIGS. 55A to 55D. The vanishing point of the motion vector is detected based on the motion vector at each representative point.

Figure 55A:
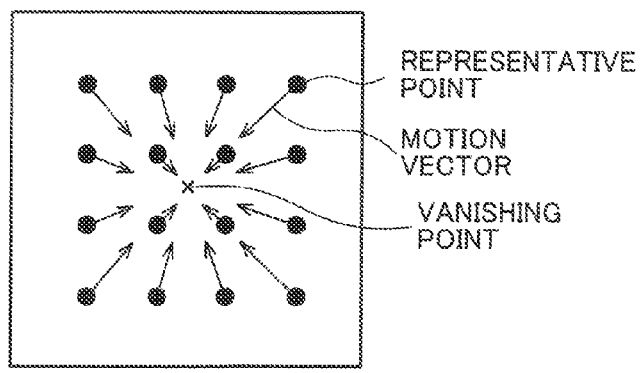
FIGS. 55A to 55D are views illustrating a withdrawal state determination method.

In FIG. 55A, each black circle indicates the representative point, each solid arrow indicates the motion vector, and the cross indicates the vanishing point. The term "vanishing point" used herein refers to the intersection point of straight lines that extend respectively from the representative points in the direction along the motion vector. For example, when the observation target is a cylindrical body having a constant inner diameter, and a motion vector occurs due to the motion of only the endoscope, straight lines that extend respectively from the representative points intersect at the vanishing point. However, since the inner diameter of a hollow tubular organ (observation target) is not constant, and a motion vector also occurs due to pulsation, straight lines that extend respectively from the representative points do not intersect at the vanishing point even in the withdrawal state. Therefore, the sum of squares of the distance from each representative point is used as a first evaluation value, and a point at which the first evaluation value becomes a minimum is determined to be a vanishing point candidate. The first evaluation value is calculated by the following expression (29) where a straight line is indicated by ax+by+c=0, and a point is indicated by (p, q).

$$D = \sum \frac{(ap + bq + c)^2}{a^2 + b^2} \tag{29}$$

Note that the sum in the expression (29) is the sum of squares of the distance from each representative point.

The coordinates (xsk, ysk) of the vanishing point candidate that minimizes the first evaluation value D are calculated by the least-square method using the following expression (30).

$$\begin{pmatrix} xsk \\ ysk \end{pmatrix} = \begin{pmatrix} \sum \frac{2a^2}{a^2+b^2} & \sum \frac{2ab}{a^2+b^2} \\ \sum \frac{2ab}{a^2+b^2} & \sum \frac{ab^2}{a^2+b^2} \end{pmatrix}^{-1} \begin{pmatrix} -\sum \frac{2ac}{a^2+b^2} \\ -\sum \frac{2bc}{a^2+b^2} \end{pmatrix} \tag{30}$$

When the coordinates of the representative point are indicated by (Px, Py), and the motion vector at the representative point is indicated by (Mx, My), a=My, b=−Mx, and c=MxPy−MyPx.

When the first evaluation value D of the vanishing point candidate is equal to or smaller than a given first threshold value, and the vanishing point candidate is present within the image, the vanishing point candidate is determined to be the vanishing point. It is determined that the vanishing point cannot be detected when the vanishing point candidate does not satisfy the above conditions.

Figure 55B:
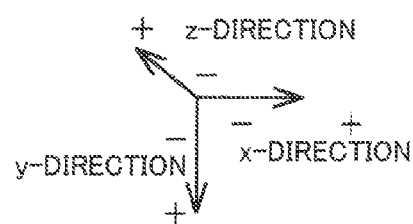
Figure 55C:
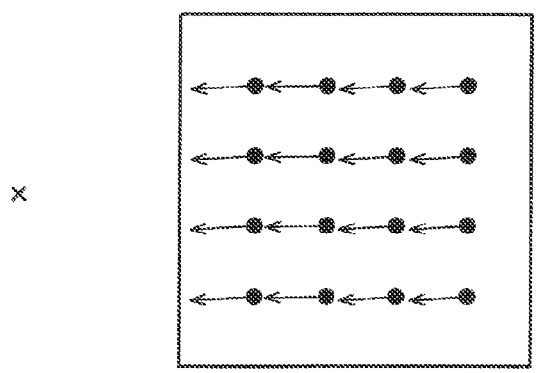

The reasons that the withdrawal state can be detected using the above conditions are described in detail below. The motion direction of the endoscope is defined as illustrated in FIG. 55B. The x-direction, the y-direction, and the z-direction respectively correspond to the horizontal direction, the vertical direction, and the depth direction that is orthogonal to the horizontal direction and the vertical direction. The motion in the direction indicated by the arrow is defined as a positive motion, and the motion in the direction opposite to the direction indicated by the arrow is defined as a negative motion. The end of the endoscope makes a motion in the negative z-direction in the withdrawal state. When the end of the endoscope makes a motion in the positive x-direction, for example, the motion vectors are almost parallel (see FIG. 55C), and the vanishing point candidate is present outside the image. Even if the vanishing point candidate is present within the image, the first evaluation value D of the vanishing point candidate is large. Specifically, the motion in the z-direction can be detected using the conditions whereby the vanishing point candidate is present within the image, and the first evaluation value D is smaller than the first threshold value.

Figure 55D:
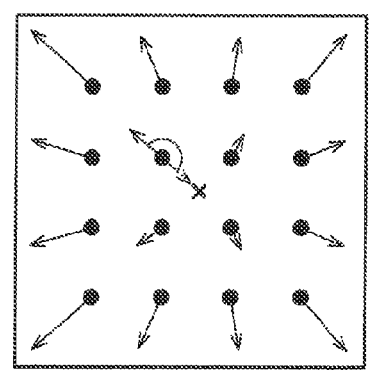

Whether or not the current state is the withdrawal state is then determined. As illustrated in FIG. 55D, the vanishing point is also detected when the endoscope is inserted. Therefore, whether or not the current state is the withdrawal state is determined based on the vector (broken arrow) from each representative point to the vanishing point and the motion vector (solid arrow). Specifically, it is determined that the vanishing point is not detected when the number of representative points for which the inner product of the vector to the vanishing point and the motion vector is negative is equal to or larger than a given number. It is determined that the current state is not the withdrawal state when the vanishing point is not detected.

The pixel value of the current frame image at the coordinates of the detected vanishing point is used as a second evaluation value, and whether or not the observation target is a hollow tubular organ is determined based on the second evaluation value. When the coordinates of the vanishing point are not an integer, the second evaluation value is calculated by linear interpolation based on the peripheral pixel values. It is determined that the observation target is a hollow tubular organ when the second evaluation value is equal to or smaller than a given second threshold value. The above determination process is necessary since the vanishing point is detected when the end of the endoscope makes a motion in the negative z-direction even if the observation target does not have a hollow tubular shape (i.e., the observation target is flat).

Specifically, when the observation target has a hollow tubular shape, the second evaluation value decreases since the vanishing point is situated in the interior of the hollow tubular organ to which the illumination light is applied to only a small extent in the current frame image. When the observation target is flat, the second evaluation value increases since the vanishing point is situated in an area in which the illumination light is sufficiently applied in the current frame image. Therefore, whether or not the current state is the withdrawal state (i.e., a state in which the hollow tubular observation target is observed while withdrawing the endoscope) can be determined by determining whether or not the second evaluation value is equal to or smaller than the second threshold value.

Although the eighth embodiment has been described above taking an example in which the attention area is immediately set within the front field of view when it has been determined that the current state is a non-withdrawal state, the configuration according to the eighth embodiment is not limited thereto. For example, the attention area may be set within the front field of view when it has been successively determined that the current state is a non-withdrawal state over a given number of frames. Likewise, the attention area may be set within the side field of view when it has been successively determined that the current state is the withdrawal state over a given number of frames. It is possible to prevent a situation in which the attention area frequently changes, and the display screen becomes unstable when the endoscope is repeatedly inserted and withdrawn little by little, by setting the attention area as described above.

9.3. Software

In the eighth embodiment, some or all of the processes performed by each section of the image processing section 410 may be implemented by software. In this case, a CPU of a computer system (described later with reference to FIG. 72, for example) executes an image processing program.

Figure 56:
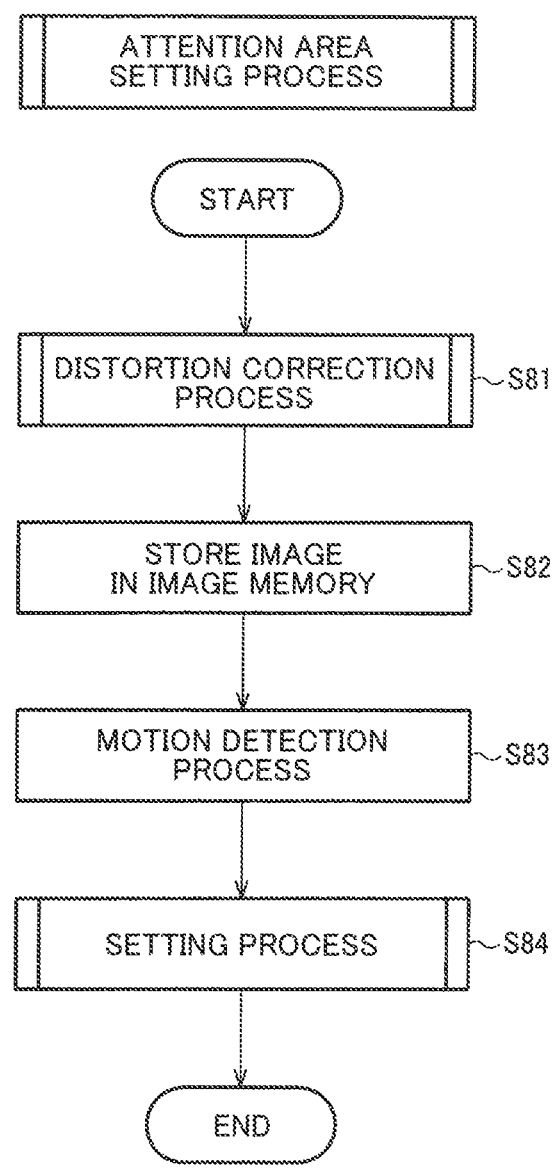
FIG. 56 illustrates an example of a detailed flowchart of an attention area setting process according to the eighth embodiment.

FIG. 56 illustrates an example of a detailed flowchart of the attention area setting process according to the eighth embodiment. The processes of the remaining steps of the image processing program are the same as described above in connection with the first embodiment (see FIG. 18 and the like).

As illustrated in FIG. 56, the distortion correction process is performed on the image signals obtained by the image generation process (S81). The distortion correction process is described in detail below with reference to FIG. 57. The image obtained by the distortion correction is stored in a memory (S82). A local motion vector is detected based on the image obtained by the distortion correction, and the image obtained by the distortion correction that has been stored in the image memory in the preceding frame (S83). The attention area is set based on the image obtained by the distortion correction process and the motion vector (S84). The setting process is described in detail below with reference to FIG. 58.

Figure 57:
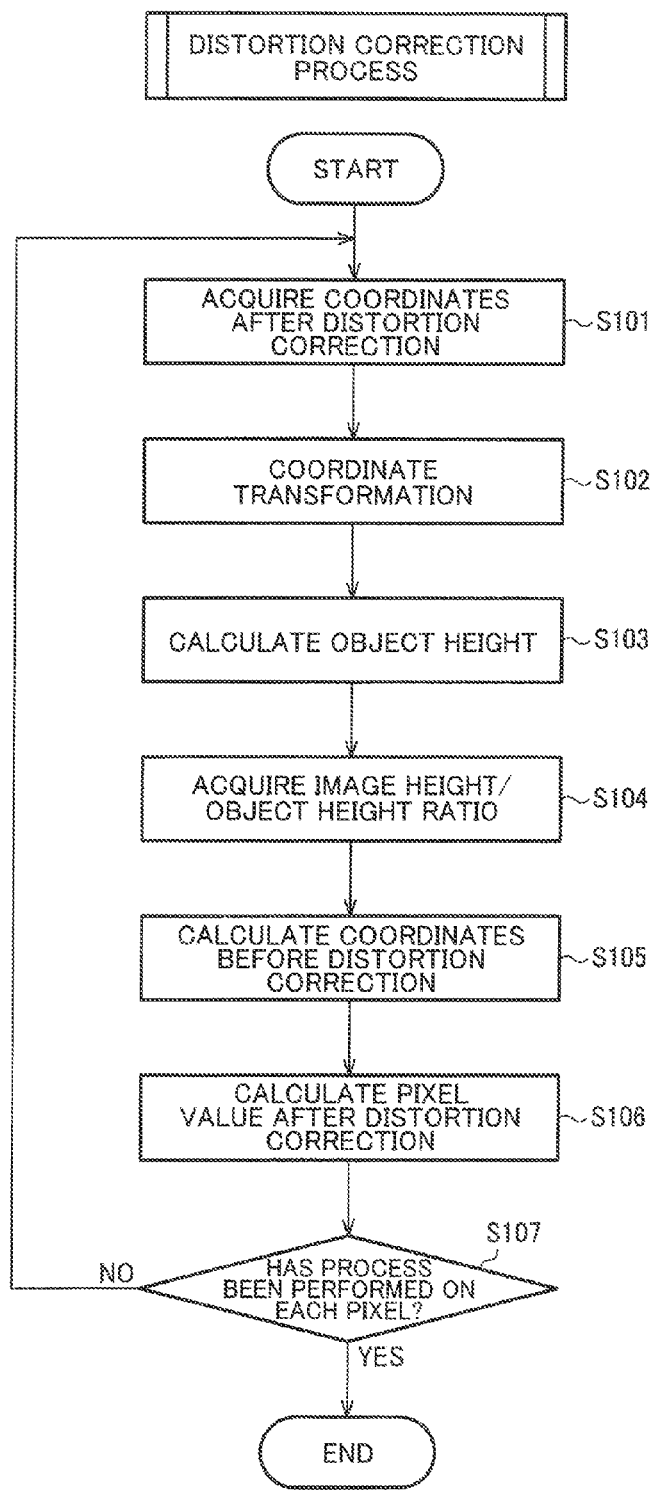
FIG. 57 illustrates an example of a detailed flowchart of a distortion correction process.

FIG. 57 illustrates an example of a detailed flowchart of the distortion correction process (S81). As illustrated in FIG. 57, the pixel coordinates of the image obtained by the distortion correction process are acquired (S101). The acquired pixel coordinates are converted into coordinates around the optical center (origin) using the expression (26) (S102). The object height r is calculated using the expression (27) based on the resulting pixel coordinates (S103). The image height/object height ratio (R/r) is calculated based on the calculated object height r (S104). For example, the relationship between the ratio R/r and the object height r is stored as a table, and the ratio R/r that corresponds to the object height r is acquired referring to the table.

The pixel coordinates (X, Y) before the distortion correction process that corresponds to the pixel coordinates (x, y) after the distortion correction process are acquired using the following expression (28) based on the calculated image height/object height ratio (S105). The pixel value at the pixel coordinates (x, y) after the distortion correction process is calculated based on the pixel coordinates (X, Y) before the distortion correction process (S106). When the pixel coordinates (X, Y) are not integers, the pixel value is calculated by performing a linear interpolation process based on the peripheral pixel values. Whether or not the above process has been performed on each pixel of the image obtained by the distortion correction process is determined (S107). When the above process has not been performed on each pixel, the process in the steps S101 to S106 is performed on the pixel that has not been subjected to the above process (S107, No). When the above process has been performed on each pixel, the process is terminated (S107, Yes).

Figure 58:
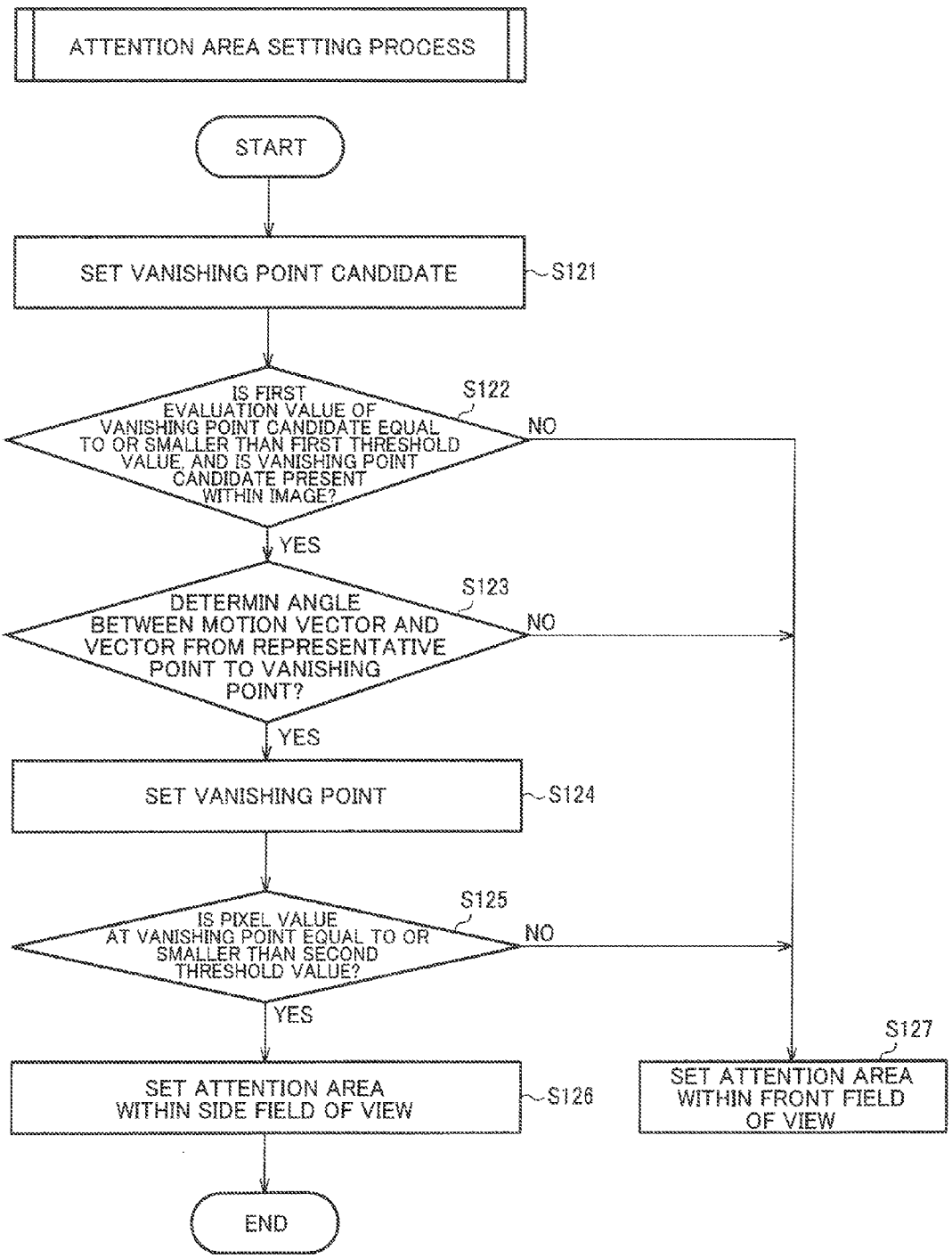
FIG. 58 illustrates an example of a detailed flowchart of a setting process.

FIG. 58 illustrates an example of a detailed flowchart of the setting process (S84). As illustrated in FIG. 58, the vanishing point candidate of the motion vector is detected based on the motion vector at the representative point (S121). Whether or not the first evaluation value of the vanishing point candidate is equal to or smaller than a given first threshold value, and the vanishing point candidate is present within the image is determined (S122).

When the first evaluation value of the vanishing point candidate is equal to or smaller than a given first threshold value, and the vanishing point candidate is present within the image (S122, Yes), whether or not the number of representative points for which the inner product of the vector to the vanishing point and the motion vector is negative is equal to or larger than a given number is determined (S123). When the number of representative points for which the inner product of the vector to the vanishing point and the motion vector is negative is equal to or larger than a given number (S123, yes), the vanishing point is set (S124).

The pixel value of the current frame image at the coordinates of the detected vanishing point is used as a second evaluation value, and whether or not the second evaluation value is equal to or smaller than a second threshold value is determined (S125). When the second evaluation value is equal to or smaller than the second threshold value (S125, Yes), the attention area is set within the side field of view (S126), and the process is terminated. When the determination result in the step S122, S123, or S125 is "No", the attention area is set within the front field of view (S127), and the process is terminated.

According to the eighth embodiment, the attention area setting section 413 includes the motion detection section 473 (see FIG. 52). The motion detection section 473 acquires the motion amount of the object based on the captured image. The attention area setting section sets the attention area based on the acquired motion amount.

Specifically, the attention area setting section 413 sets an area of the captured image that corresponds to the side field of view to be the attention area when it has been determined that the scope is being withdrawn based on the motion amount (see FIG. 55A and the like).

A large intestine is normally observed while withdrawing the scope. Therefore, information useful for performing diagnosis on the back side of the folds of a large intestine or the like can be acquired by setting an area that corresponds to the side field of view to be the attention area when the scope is withdrawn, and enlarging the attention area.

The motion detection section 473 may calculate the motion vectors of a plurality of representative points as the motion amount, and may calculate the vanishing point of the calculated motion vectors. The attention area setting section 413 may determine that the scope is being withdrawn when the calculated vanishing point is present within the captured image, and the inner product of the vector from each representative point to the vanishing point and the motion vector is positive.

According to the above configuration, whether the scope is being inserted or withdrawn can be determined by determining the position of the vanishing point, and determining the direction of the motion vector.

The attention area setting section 413 may determine that the scope is being withdrawn when it has been determined that the pixel value of the vanishing point is smaller than a threshold value (second threshold value).

According to the above configuration, since whether the scope faces the wall surface or faces in the direction along a lumen can be determined, whether or not the scope is being withdrawn (i.e., whether or not the scope is moving in the direction along a lumen) can be determined.

The attention area setting section 413 may set an area of the captured image that corresponds to the front field of view to be the attention area when it has been determined that the scope is not being withdrawn based on the motion amount.

The above configuration makes it possible to set the attention area within the front field of view that is considered to be mainly used when the scope is not being withdrawn, and enlarge the attention area. For example, since the endoscope is operated using the front field of view during insertion, it is possible to present information within the front field of view that is useful for the operation.

The motion detection section 473 may include the distortion correction section 471 (see FIG. 52). The distortion correction section 471 may perform the distortion correction process on the captured image based on the distortion of the optical system included in the scope. The motion detection section 473 may acquire the motion amount based on the captured image that has been subjected to the distortion correction process.

The above configuration makes it possible to correct the distortion of the image when using a wide-angle optical system such as the objective optical system illustrated in FIG. 1. This makes it possible to reduce the effects of distortion on the motion amount detection process.

10. Ninth Embodiment 10.1. Endoscope System

A ninth embodiment in which shape information about the object is acquired using a shape detection section, and the attention area is set based on the shape information is described below.

Figure 59:
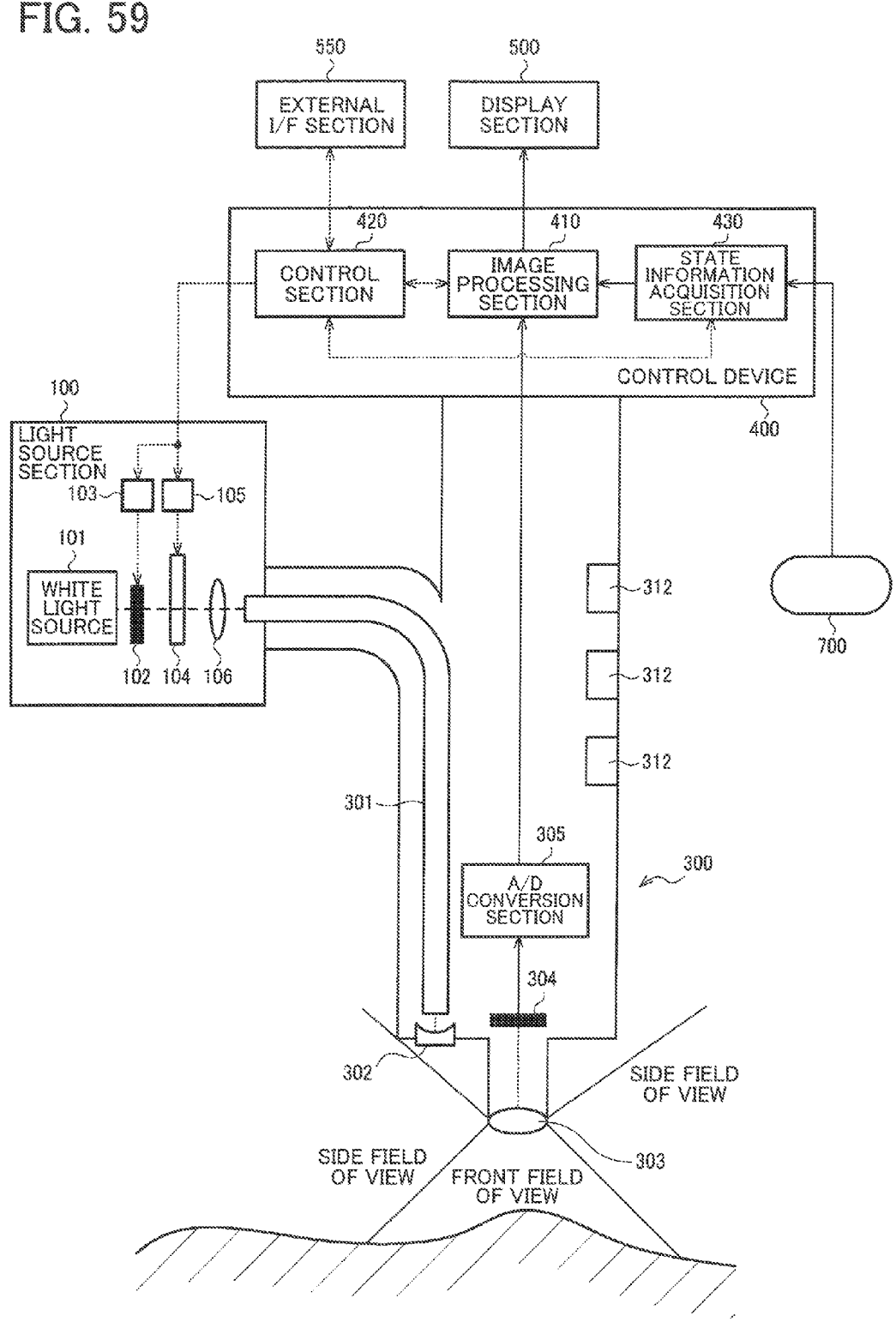
FIG. 59 illustrates a configuration example of an endoscope system according to a ninth embodiment.

FIG. 59 illustrates a configuration example of an endoscope system according to the ninth embodiment. The endoscope system includes a light source section 100, an insertion section 300, a control device 400, a display section 500, an external I/F section 550, and a shape detection section 700 (e.g., position detecting unit (PDU)). Note that the same elements as those described above with reference to FIG. 21 and the like are indicated by identical reference signs, and description of these elements is appropriately omitted.

The insertion section 300 includes a light guide fiber 301, an illumination lens 302, an objective optical system 303, an image sensor 304, an A/D conversion section 305, and a magnetic coil 312. Note that the configuration of each section other than the magnetic coil 312 is the same as described above in connection with the first embodiment, and description thereof is omitted.

For example, more than a dozen magnetic coils 312 are provided in the insertion section 300, and each magnetic coil 312 transmits magnetism to the shape detection section 700 (shape information acquisition section in a broad sense). The magnetic coils 312 are arranged along the lengthwise direction of the insertion section 300, for example.

The shape detection section 700 receives the magnetism transmitted from each magnetic coil 312 provided in the insertion section 300 through an antenna (not illustrated in FIG. 43) to acquire three-dimensional position information about each magnetic coil in real time. The shape detection section 700 acquires endoscope shape information (that indicates the shape of the insertion section 300) in real time from the acquired three-dimensional position information about each magnetic coil.

The control device 400 includes an image processing section 410, a control section 420, and a state information acquisition section 430. Note that the configuration of the control section 420 is the same as described above in connection with the first embodiment, and description thereof is omitted.

10.2. State Information Acquisition Section

Figure 60:
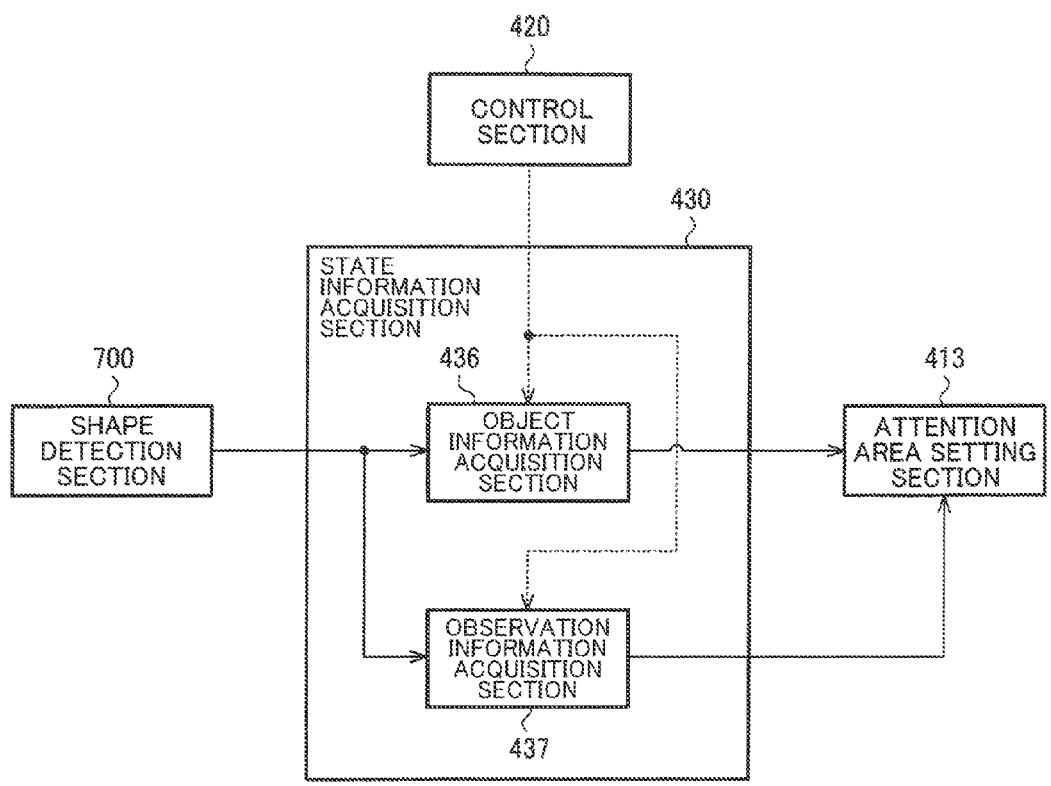
FIG. 60 illustrates a detailed configuration example of a state information acquisition section according to the ninth embodiment.

FIG. 60 illustrates a detailed configuration example of the state information acquisition section 430 according to the ninth embodiment. The state information acquisition section 430 includes an object information acquisition section 436 and an observation information acquisition section 437. The shape detection section 700 outputs the detected endoscope shape information to the object information acquisition section 436 and the observation information acquisition section 437. The object information acquisition section 436 is connected to the attention area setting section 413. The observation information acquisition section 437 is also connected to the attention area setting section 413.

The object information acquisition section 436 determines whether or not the object is a lower gastrointestinal tract based on the endoscope shape information acquired by the shape detection section 700. Specifically, the object information acquisition section 436 acquires the length of the part of the endoscope that is inserted into a body, and a determination result as to whether the endoscope has a loop shape based on the endoscope shape information, and determines whether or not the object is a lower gastrointestinal tract based on the acquired length and determination result.

When observing a lower gastrointestinal tract using the endoscope, the endoscope is inserted deeply as compared with the case of observing another internal organ. Therefore, the object information acquisition section 436 determines that the object is a lower gastrointestinal tract when the length of the part of the endoscope that is inserted into a body is equal to or larger than a given value. An insertion technique that facilitates insertion by forming a loop using the endoscope is used only when inserting the endoscope into a lower gastrointestinal tract. Therefore, the object information acquisition section 436 determines that the object is a lower gastrointestinal tract when the endoscope forms a loop.

The object information acquisition section 436 determines that the object is not a lower gastrointestinal tract until the length of the part of the endoscope that is inserted into a body exceeds a given value, or the endoscope forms a loop. The object information acquisition section 436 determines that the object is a lower gastrointestinal tract when one of the above conditions has been satisfied, and maintains the determination result thereafter. The object information acquisition section 436 outputs the determination result to the attention area setting section 413 as object information.

The observation information acquisition section 437 determines whether or not the endoscope is being withdrawn based on the endoscope shape information acquired by the shape detection section 700. Specifically, the observation information acquisition section 437 determines whether or not the length of the part of the endoscope that is inserted into a body has decreased with the lapse of time based on the endoscope shape information, and determines that the endoscope is being withdrawn when the length of the part of the endoscope that is inserted into a body has decreased with the lapse of time. The observation information acquisition section 437 outputs the withdrawal state determination result to the attention area setting section 413 as observation information.

10.3 Image Processing Section

Figure 61:
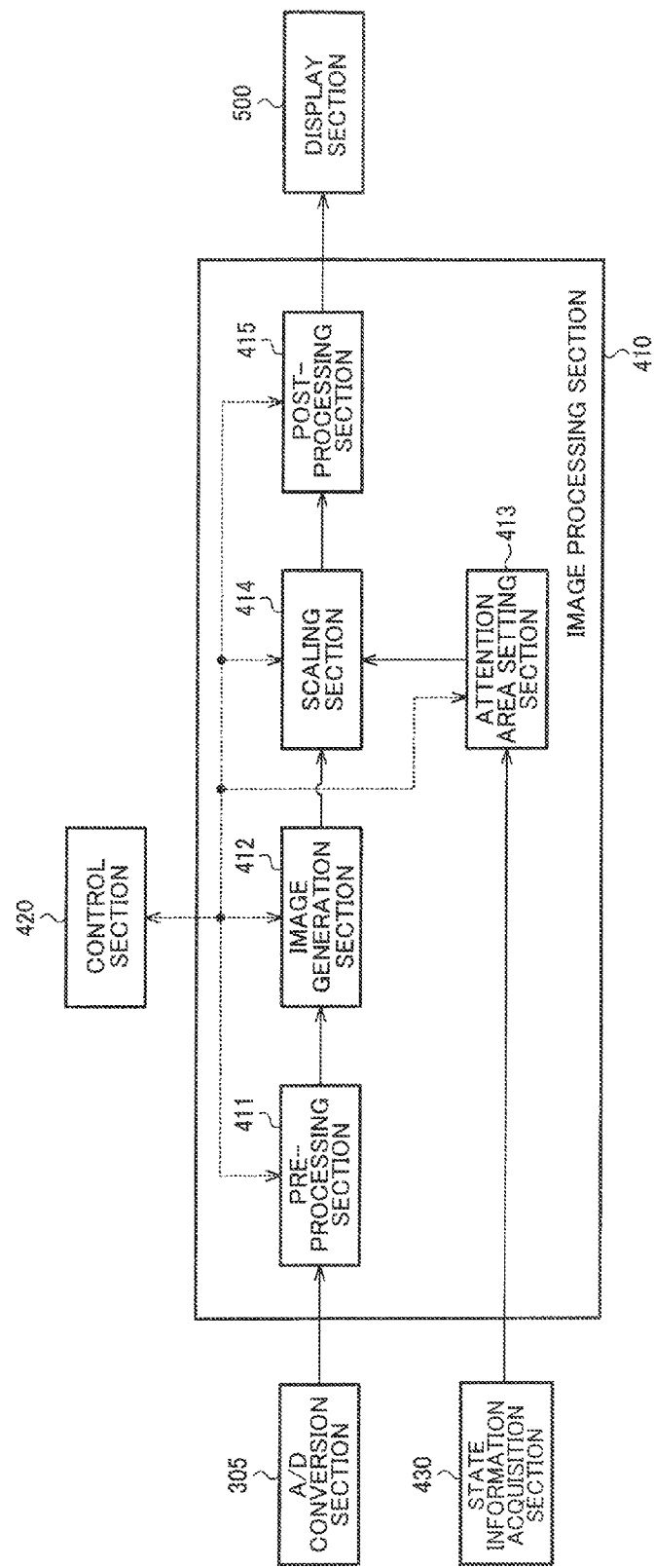
FIG. 61 illustrates a detailed configuration example of an image processing section according to the ninth embodiment.

FIG. 61 illustrates a detailed configuration example of the image processing section 410 according to the ninth embodiment. The image processing section 410 includes a preprocessing section 411, an image generation section 412, an attention area setting section 413, a scaling section 414, and a post-processing section 415. The configuration other than the attention area setting section 413 is the same as described above in connection with the second embodiment, and description thereof is omitted.

The attention area setting section 413 sets the attention area based on the object information and the observation information output from the state information acquisition section 430. Specifically, the attention area setting section 413 sets the attention area within the side field of view when it has been determined that the object is a lower gastrointestinal tract based on the object information, and it has been determined that the endoscope is being withdrawn based on the observation information. Otherwise the attention area setting section 413 sets the attention area within the front field of view. The attention area setting section 413 outputs information about the set attention area to the scaling section 414.

According to the ninth embodiment, the endoscope system includes the shape detection section 700 that acquires the shape information (e.g., the three-dimensional position information about the magnetic coil 312 illustrated in FIG. 59) about a scope insertion section (insertion section 300) (see FIG. 60). The state information acquisition section 430 includes the object information acquisition section 436. The object information acquisition section 436 acquires the acquired shape information as the state information, and acquires the object information based on the shape information. The attention area setting section 413 sets the attention area based on the acquired object information.

Specifically, the object information acquisition section 436 may determine the object based on the shape information, and may acquire the determined object as the object information. The attention area setting section 413 may set an area of the captured image that corresponds to the side field of view to be the attention area when it has been determined that the part observed as the object is a lower gastrointestinal tract.

More specifically, the object information acquisition section 436 may determine that the part observed as the object is a lower gastrointestinal tract when it has been determined that the scope insertion section has a loop shape.

The above configuration makes it possible to set the attention area based on the part that has been determined based on the shape information, and enlarge the attention area. It is also possible to provide the operator with information useful for performing diagnosis on the back side of the folds of a large intestine or the like when the scope is withdrawn, by enlarging the side field of view when the object is a lower gastrointestinal tract.

Note that the object information refers to information about the object. It suffices that the object information be information that is estimated from the shape information about the object. For example, the object information may be information about the size or the length of the object.

The state information acquisition section 430 may include the observation information acquisition section 437. The observation information acquisition section 437 may acquire the acquired shape information as the state information, and may acquire the observation state information based on the shape information. The attention area setting section 413 may set the attention area based on the acquired observation state information.

Specifically, the observation information acquisition section 437 may determine the travel direction of the scope based on the shape information, and may acquire the determined travel direction as the observation state information. The attention area setting section 413 may set an area of the captured image that corresponds to the side field of view to be the attention area when it has been determined that the scope is being withdrawn.

The above configuration makes it possible to enlarge the side field of view when the scope is being withdrawn. For example, it is possible to allow the operator to easily observe the back side of folds or the like by enlarging the side field of view when the object is a lower gastrointestinal tract, and the scope is being withdrawn.

The attention area setting section 413 may set an area of the captured image that corresponds to the front field of view to be the attention area when it has been determined that the object is not a lower gastrointestinal tract, and it has been determined that the scope is not being withdrawn.

The above configuration makes it possible to set the attention area within the front field of view that is important when observing an upper gastrointestinal tract, or when inserting the scope into a lower gastrointestinal tract, and enlarge the attention area by performing the scaling process.

11. Tenth Embodiment 11.1. Outline

A tenth embodiment in which a red-out area is detected from the image, and an area other than the red-out area is set to be the attention area is described below.

It is difficult to insert the endoscope into a large intestine because a large intestine is a narrow lumen, is winding and twisted, and deforms upon insertion of the endoscope. The operator inserts the endoscope into a large intestine by carefully operating the endoscope while observing the endoscopic image, and determining the insertion direction. The operator operates the endoscope by performing an angular operation (upward/downward/rightward/leftward) on the end of the endoscope, and a push/pull/twist operation on the endoscope insertion section (hereinafter appropriately referred to as "scope").

Such an insertion technique is difficult for an inexperienced doctor. In particular, since the doctor normally moves the endoscope insertion section forward when inserting the endoscope, the end of the endoscope frequently comes in contact with the intestinal wall, and the entire endoscopic image is in a red-out defocused state. In this case, it is impossible to determine the insertion direction. When the red-out state has occurred, it is necessary to cancel the red-out state by moving the endoscope insertion section backward to some extent, and then insert the endoscope insertion section again. This result in an increase in insertion time.

When the endoscope includes a wide-angle optical system having an angle of view equal to or larger than 180°, the entire field of view is not necessarily lost even if the end of the endoscope comes in contact with the intestinal wall, and the entire endoscopic image is not necessarily subjected to the red-out state (i.e., part of the field of view is maintained). Specifically, it may be possible to determine the insertion direction even when the end of the endoscope comes in contact with the intestinal wall.

In the tenth embodiment, a red-out area is detected from an endoscopic image captured using an optical system having an angle of view equal to or larger than 180°, an area other than the red-out area is set to be the attention area, and the endoscopic image is presented to the doctor in a state in which the visibility of the attention area is improved so that the insertion time can be reduced. A state in which visibility is improved refers to a state in which the visibility of the attention area is improved.

Figure 62:
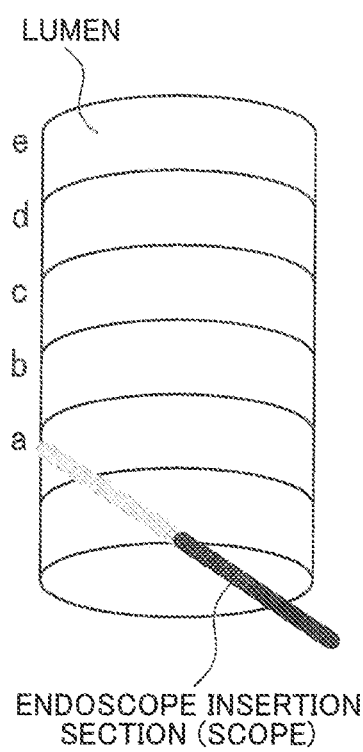
FIG. 62 is a view illustrating a red-out area.

FIG. 62 illustrates a state in which the end of an endoscope insertion section comes in diagonal contact with a wall surface of a lumen that simulates a large intestine.

Figure 63A:
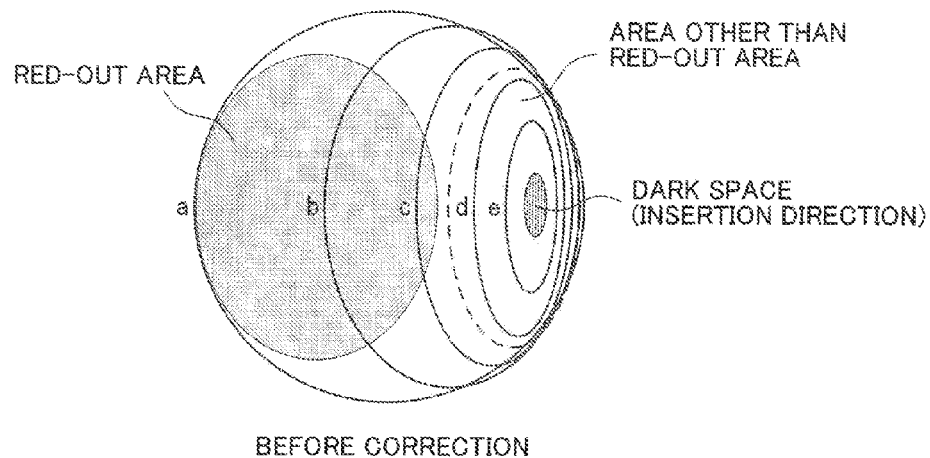
FIG. 63A is a view illustrating a red-out area.
Figure 63B:
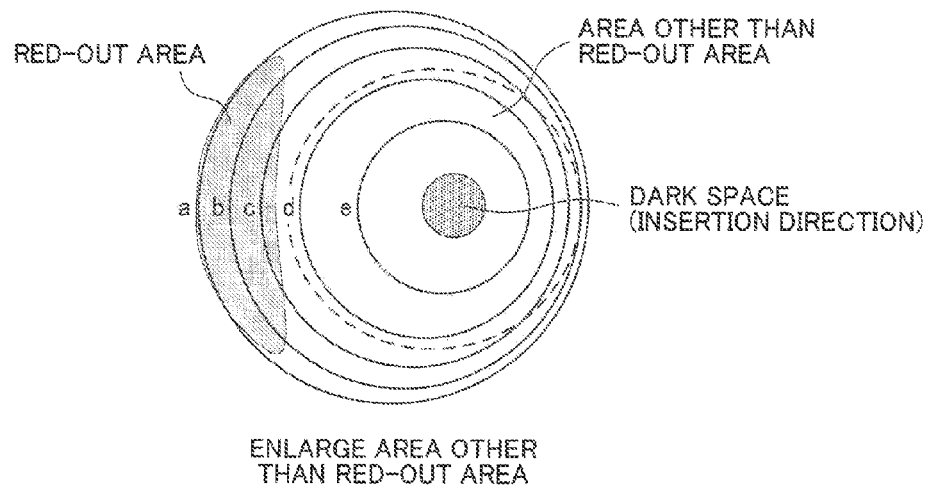
FIG. 63B is a view illustrating a scaling process according to a tenth embodiment.

In this state, a red-out area occupies the majority of the endoscopic image (see FIG. 63A). It is still possible to determine the insertion direction as a dark space when the lumen is straight and open. On the other hand, when the lumen is curved or closed, it is difficult to determine the insertion direction, and it is desirable that the endoscopic image can be observed in a state in which an area (attention area) other than the red-out area is enlarged. Therefore, an area (attention area) other than the red-out area is enlarged as illustrated in FIG. 63B. This makes it possible to determine the insertion direction that is difficult to determine.

In the red-out area illustrated in FIG. 64A, the illumination light is applied to the intestinal wall in a state in which the end of the insertion section comes in contact with the intestinal wall. Therefore, a relative difference in brightness occurs between the red-out area and an area (attention area) other than the red-out area. In particular, the endoscope is configured so that the exposure of the endoscopic image is controlled to correct exposure by adjusting the intensity of illumination light (dimming control process). Therefore, when the red-out area occupies the majority of the endoscopic image, the dimming control process may be performed so that the red-out area has a brightness at correct exposure. In this case, even if an area (attention area) other than the red-out area is positioned within the field of view, the area (attention area) other than the red-out area may be dark, and correct exposure may not be achieved. Therefore, the insertion direction cannot be determined (observed) even if the attention area is enlarged. Therefore, an area (attention area) other than the red-out area is designated to be the dimming target area, and subjected to the dimming control process. This makes it possible to observe the attention area at correct exposure, and easily determine the insertion direction.

In the example illustrated in FIG. 63A in which the end of the endoscope insertion section comes in diagonal contact with the intestinal wall, it may be possible to insert the endoscope insertion section while determining that the insertion direction is an area other than the red-out area. However, the end of the endoscope may come in contact with the intestinal wall in a state in which the end of the endoscope is orthogonal to the intestinal wall in a curved area of the large intestine (lumen). In this case, a red-out area is observed in the center area of the endoscopic image, and an area (attention area) other than the red-out area is observed in the peripheral area of the endoscopic image. Therefore, the insertion direction cannot be determined by merely determining an area other than the red-out area. In this case, the peripheral area (attention area) is enlarged, designated to be the dimming target area, and subjected to the dimming control process. This makes it possible to more easily determine the insertion direction from the enlarged peripheral area)(360°.

11.2. Image Processing Section

The method that detects the red-out area, and the method that sets an area other than the red-out area to be attention area are described in detail below.

Figure 64:
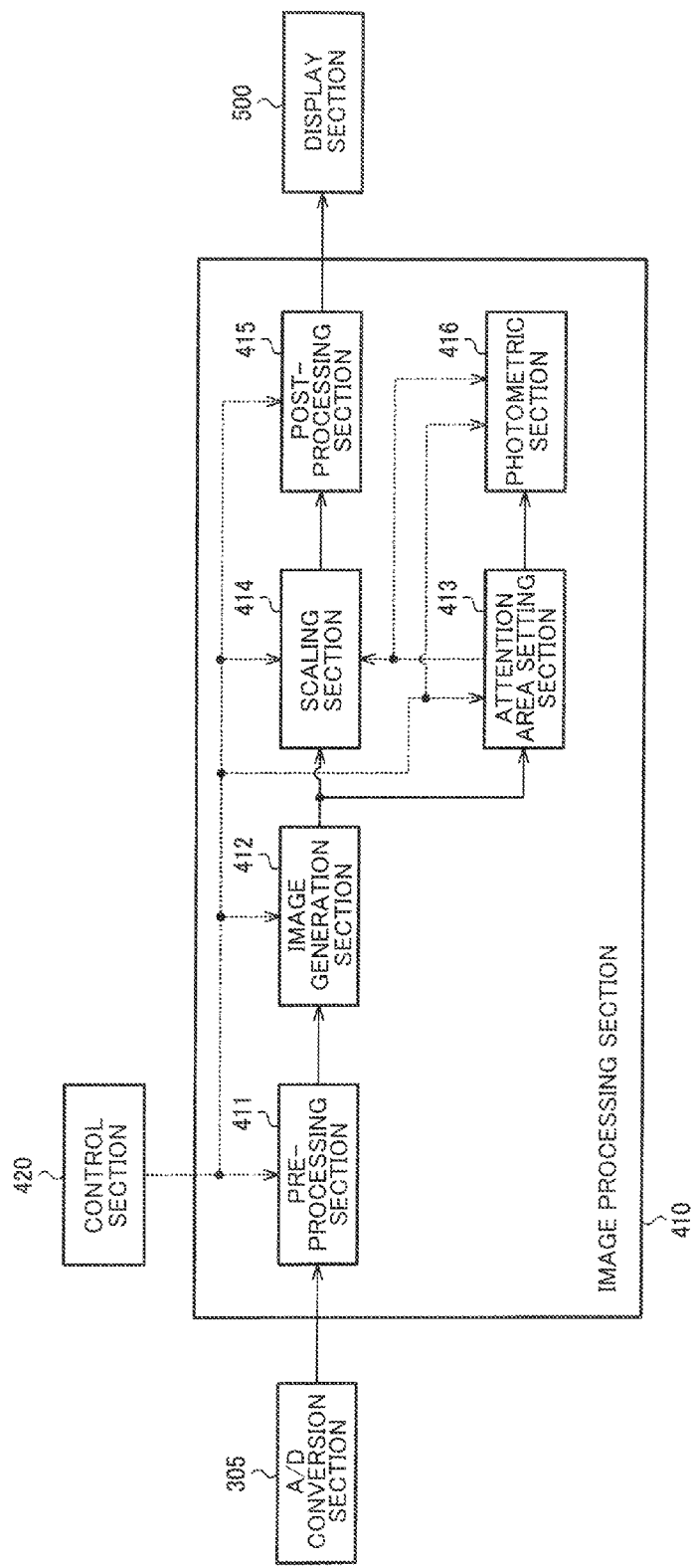
FIG. 64 illustrates a detailed configuration example of an image processing section according to the tenth embodiment.

FIG. 64 illustrates a detailed configuration example of the image processing section 410 according to the tenth embodiment. The image processing section 410 includes a preprocessing section 411, an image generation section 412, an attention area setting section 413, a scaling section 414, a post-processing section 415, and a photometric section 416. Note that the same elements as those described above with reference to FIG. 6 and the like are indicated by identical reference signs, and description of these elements is appropriately omitted. Note that the configuration of the endoscope system according to the tenth embodiment is the same as the configuration of the endoscope system according to the first embodiment (see FIG. 3).

The preprocessing section 411 is connected to the image generation section 412. The image generation section 412 is connected to the attention area setting section 413 and the scaling section 414. The attention area setting section 413 is connected to the scaling section 414 and the photometric section 416. The scaling section 414 is connected to the post-processing section 415. The post-processing section 415 is connected to the display section 500. The control section 420 is connected to the preprocessing section 411, the image generation section 412, the attention area setting section 413, the scaling section 414, the post-processing section 415, and the photometric section 416.

The attention area setting section 413 sets an area other than the red-out area to be the attention area. The scaling section 414 enlarges the set attention area. The details of the above process are described later. The photometric section 416 calculates the brightness (e.g., luminance) of the image. The photometric section 416 calculates the brightness of the attention area when the attention area has been set. The photometric section 416 outputs the calculated brightness to the control section 420. The control section 420 performs the dimming control process by controlling the light source aperture driver section 103 based on the brightness.

11.3. Attention Area Setting Section

Figure 65:
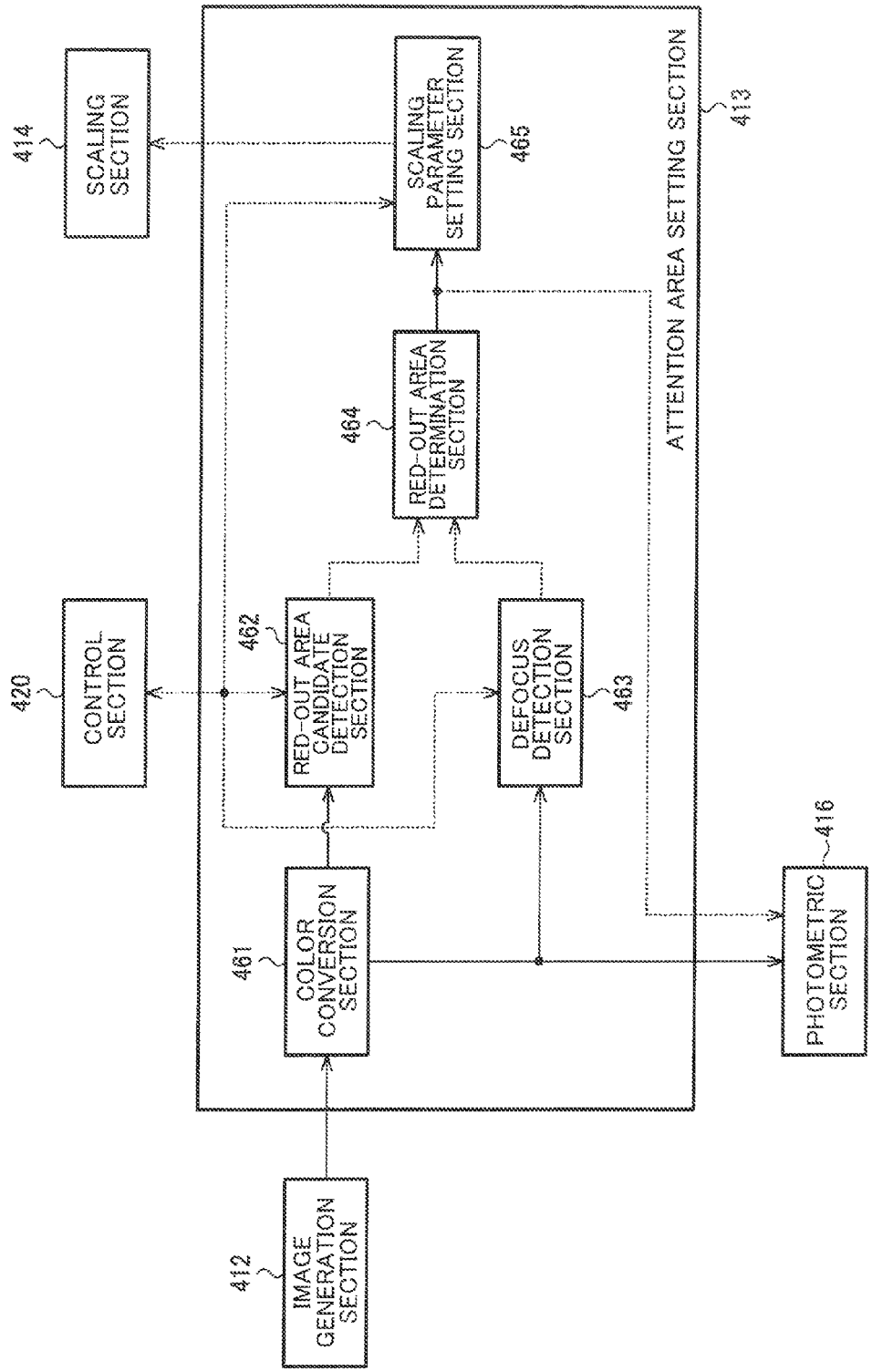
FIG. 65 illustrates a detailed configuration example of an attention area setting section according to the tenth embodiment.

FIG. 65 illustrates a detailed configuration example of the attention area setting section 413 according to the tenth embodiment. The attention area setting section 413 includes a color conversion section 461, a red-out area candidate detection section 462, a defocus detection section 463, a red-out area determination section 464, and a scaling parameter setting section 465.

The color conversion section 461 is connected to the red-out area candidate detection section 462 and the defocus detection section 463. The red-out area candidate detection section 462 is connected to the red-out area determination section 464. The defocus detection section 463 is connected to the red-out area determination section 464. The red-out area determination section 464 is connected to the scaling parameter setting section 465 and the photometric section 416. The scaling parameter setting section 465 is connected to the scaling section 414. The control section 420 is connected to the red-out area candidate detection section 462, the defocus detection section 463, and the scaling parameter setting section 465.

The color conversion section 461 converts the RGB signals of the color image output from the image generation section 412 into luminance signals and color signals. The following description is given taking an example in which RGB signals are converted into YCbCr signals. The color conversion section 461 outputs the luminance signals Y to the defocus detection section 463 and the photometric section 416, and outputs the color difference signals Cb and Cr to the red-out area candidate detection section 462.

The red-out area candidate detection section 462 divides the input color difference signals Cb and Cr into a plurality of block areas based on block size information (e.g., N×N blocks) output from the control section 420. The red-out area candidate detection section 462 determines a red-out area candidate from the statistics of the color difference signals within each block area, and outputs determination information about each block area to the red-out area determination section 464.

The defocus detection section 463 divides the input luminance signals Y into a plurality of block areas based on the block size information output from the control section 420. The defocus detection section 463 determines whether or not each block area is in a defocus state based on the presence or absence of a high-frequency component in the block area, and outputs the determination information about each block area to the red-out area determination section 464.

The red-out area determination section 464 determines the block area that is determined to be the red-out area candidate area by the red-out area candidate detection section 462, and determined to be in a defocus state by the defocus detection section 463, to be the red-out area. The red-out area determination section 464 outputs the determination result to the scaling parameter setting section 465 and the photometric section 416.

Figure 66:
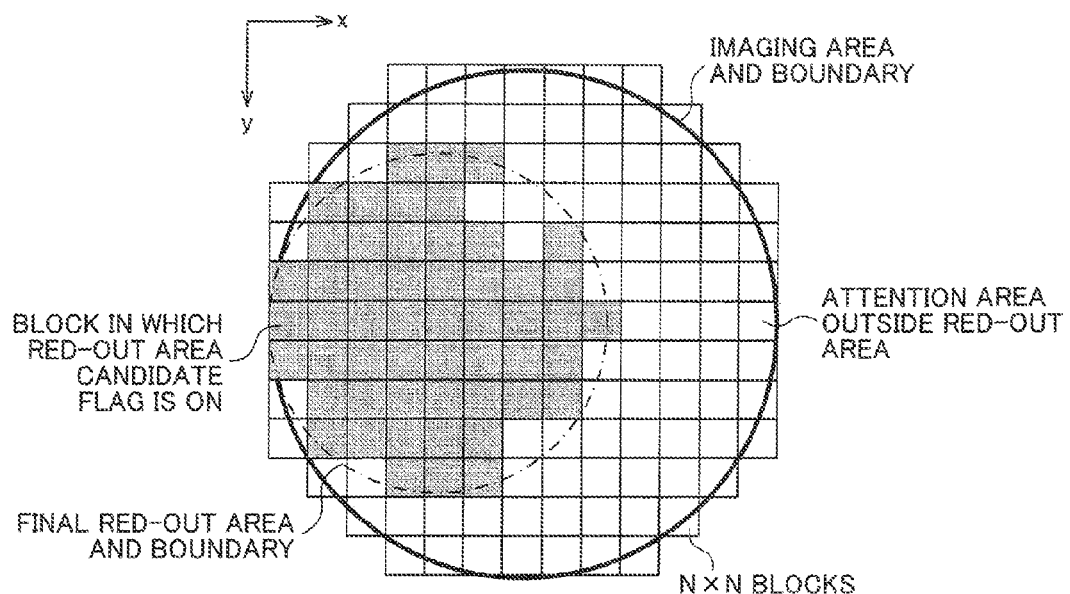
FIG. 66 is a view illustrating a process performed by an attention area setting section according to the tenth embodiment.

The scaling parameter setting section 465 sets the scaling parameter for each block area (each of the N×N blocks) (see FIG. 66). Specifically, the scaling parameter setting section 465 sets each block area that is included in the imaging area and is determined to be other than the red-out area to be the attention area based on the determination result of the red-out area determination section 464. The scaling parameter setting section 465 sets the scaling parameter for each block area based on the relationship between the attention area and the red-out area, and outputs the set scaling parameter to the scaling section 414.

The scaling section 414 resets the display scaling factor so that the attention area included in the imaging area is enlarged, and generates an image in which the attention area is relatively enlarged with respect to the red-out area. The expression "resets the display scaling factor" means that a conversion table for the coordinate position (real number) before the scaling process with respect to the pixel position (integer) after the scaling process is generated along with a change in the display scaling factor.

The photometric section 416 calculates the average luminance level of the attention areas based on the attention area information output from the attention area setting section 413 and the luminance signals output from the color conversion section 461.

11.4. Red-Out Area Candidate Detection Section

Figure 67:
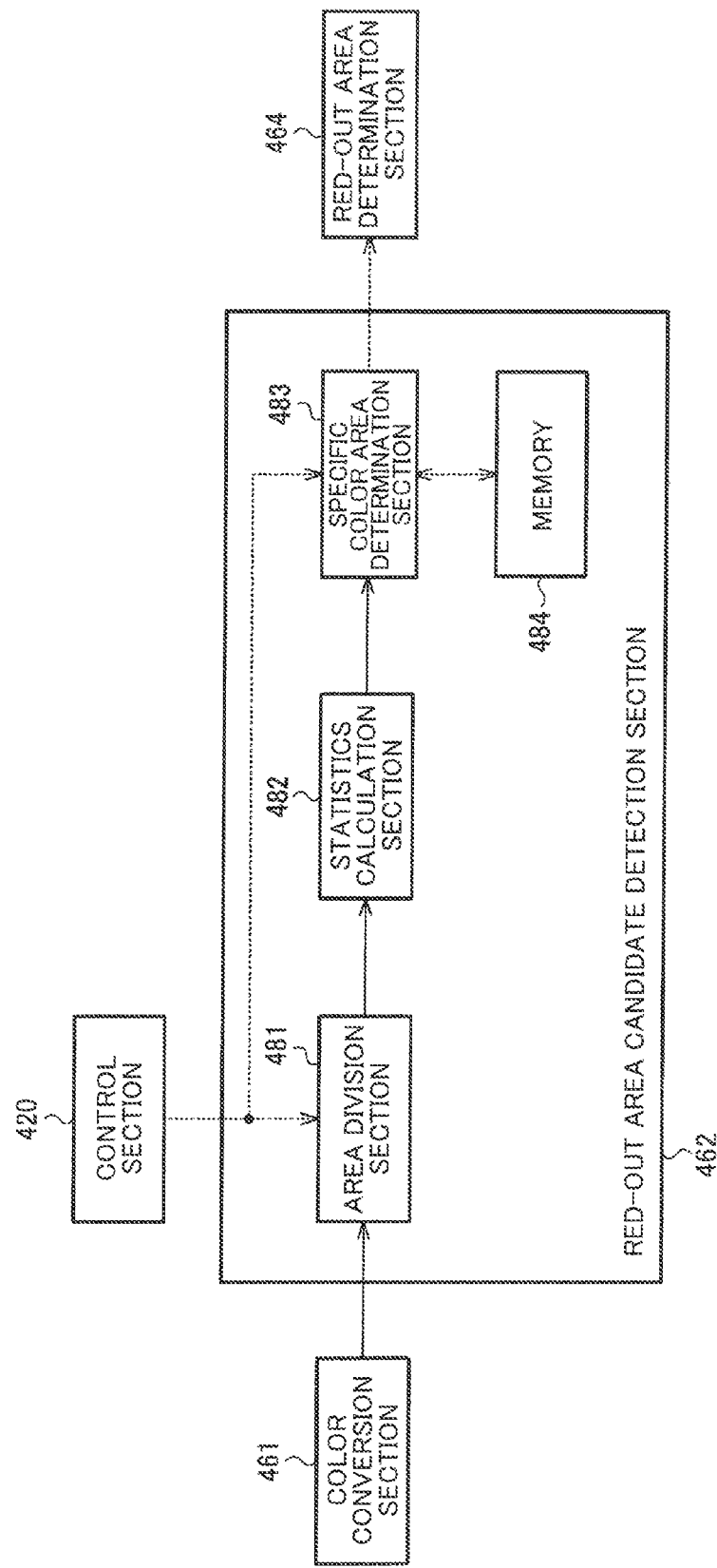
FIG. 67 illustrates a detailed configuration example of a red-out area candidate detection section.

FIG. 67 illustrates a detailed configuration example of the red-out area candidate detection section 462. The red-out area candidate detection section 462 includes an area division section 481, a statistics calculation section 482, a specific color area determination section 483, and a memory 484.

The area division section 481 is connected to the statistics calculation section 482. The statistics calculation section 482 is connected to the specific color area determination section 483. The specific color area determination section 483 is connected to the memory 484 and the red-out area determination section 464. The control section 420 is connected to the area division section 481 and the specific color area determination section 483.

The area division section 481 divides the Cb signals and the Cr signals output from the color conversion section 461 into a plurality of block areas based on the block size information output from the control section 420, and outputs information about each block area to the statistics calculation section 482.

The statistics calculation section 482 calculates the average value Cba(x, y) and the standard deviation Cbs(x, y) of the Cb signals in the Cb signal block areas, and calculates the average value Cra(x, y) and the standard deviation Crs(x, y) of the Cr signals in the Cr signal block areas. The statistics calculation section 482 outputs the calculated values to the specific color area determination section 483. Note that x is the coordinate value of the block area in the horizontal direction, and y is the coordinate value of the block area in the vertical direction. The upper left corner of the image is the origin (0, 0). The coordinate value x increases in the rightward direction (i.e., a horizontal scan direction) of the image, and the coordinate value y increases in the downward direction (i.e., a direction that perpendicularly intersects the horizontal scan direction) of the image.

The average value and the standard deviation are input to the specific color area determination section 483. Specific color area information that specifies the red-out area candidate in a two-dimensional plane (hue plane) of which the coordinate axes are the Cb signal and the Cr signal, is input to the specific color area determination section 483 from the control section 420.

The term "specific color area information" used herein refers to information that designates an area in the hue plane. An area may be designated using the hue angle and the chroma, or may be designated using the CbCr coordinates, for example.

Normal color area information that specifies the color area of a mucous membrane and a blood vessel when observing a large intestine is input to the specific color area determination section 483 from the control section 420. The normal color area information is information that designates an area in the hue plane. An area may be designated in the same manner as the specific color area information. Note that the region in the hue plane indicated by the specific color area information is referred to as "specific color area", and the region in the hue plane indicated by the normal color area information is referred to as "normal color area".

The specific color area determination section 483 sets a red-out area candidate flag Frc(x, y) of the block area to ON when the average values Cba (x, y) and Cra (x, y) are within the specific color area, and stores the red-out area candidate flag Frc(x, y) in the memory 484 (see FIG. 66). The red-out area candidate flag Frc(x, y) is assigned to each block area as a flag that indicates the red-out area candidate. The specific color area determination section 483 sets the red-out area candidate flag Frc(x, y) of the block area to OFF when the block area is not determined to be the red-out area candidate, and stores the red-out area candidate flag Frc(x, y) in the memory 484.

The specific color area determination section 483 does not change the red-out area candidate flag Frc(x, y) of the block area when the standard deviation Cbs(x, y) is smaller than a threshold value ThCb, and the standard deviation Crs(x, y) is smaller than a threshold value ThCr. The threshold values ThCb and ThCr are stored in the memory 484. The specific color area determination section 483 sets the red-out area candidate flag Frc(x, y) of the block area to OFF when the standard deviation Cbs(x, y) is equal to or larger than the threshold value ThCb, or the standard deviation Crs(x, y) is equal to or larger than the threshold value ThCr. The specific color area determination section 483 outputs the set red-out area candidate flag Frc(x, y) to the red-out area determination section 464.

The threshold values ThCb and ThCr indicate the case where the average values Cba(x, y) and Cra(x, y) of the block area of the captured color image are included in the normal color area, and are obtained by multiplying the maximum values MaxCbss and MaxCrss of the standard deviations Cbs(x, y) and Crs(x, y) of the block area by a given coefficient (i.e., a coefficient smaller than 1). The given coefficient is stored in advance in the control section 420, and acquired from the control section 420.

The maximum standard deviations MaxCbss and Max-Crss of a standard mucous membrane area are used as a reference in order to detect a block area in which the color difference included in the specific color area is smaller than that of a normally observed mucous membrane area as the red-out area candidate. Specifically, when the red-out area is in a defocus state, the blood vessels in the mucous membrane are not decomposed, and the color difference between the mucous membrane and the blood vessels decreases.

11.5. Defocus Detection Section

Figure 68:
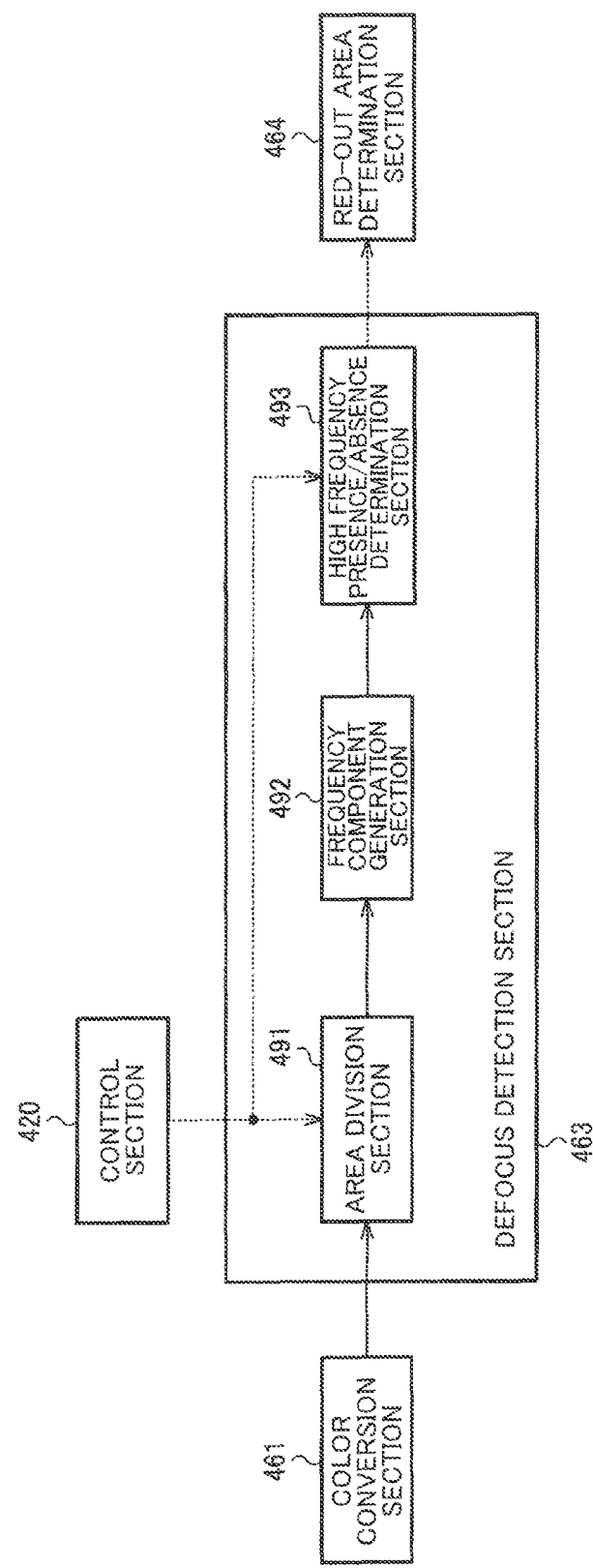
FIG. 68 illustrates a detailed configuration example of a defocus detection section.

FIG. 68 illustrates a detailed configuration example of the defocus detection section 463. The defocus detection section 463 includes an area division section 491, a frequency component generation section 492, and a high frequency presence/absence determination section 493.

The area division section 491 is connected to the frequency component generation section 492. The frequency component generation section 492 is connected to the high frequency presence/absence determination section 493. The control section 420 is connected to the area division section 491 and the high frequency presence/absence determination section 493.

The area division section 491 divides the luminance signals output from the color conversion section 461 into a plurality of block areas based on the block size information output from the control section 420, and outputs information about each block area to the fequency component generation section 492.

The frequency component generation section 492 performs a discrete cosine transform (DCT) or a fast Fourier transform (FFT) on each block area to generate frequency components. The frequency component generation section 492 outputs the generated frequency components of each block area to the high frequency presence/absence determination section 493.

The frequency components of each block area, and a high frequency determination threshold value Thf and a high frequency presence/absence determination threshold value Thp output from the control section 420 are input to the high frequency presence/absence determination section 493. The high frequency presence/absence determination section 493 determines that the block area is in an in-focus state when the highest frequency of the frequency component of which the amplitude value is higher than a given value is larger than the high frequency determination threshold value Thf, and the sum of the frequency components is larger than the high frequency presence/absence determination threshold value Thp, and sets a defocus state flag Fdf(x, y) to OFF. The high frequency presence/absence determination section 493 determines that the block area is in a defocus state when the sum of the frequency components is equal to or smaller than the high frequency presence/absence determination threshold value Thp, and sets the defocus state flag Fdf(x, y) to ON. The high frequency presence/absence determination section 493 outputs the set defocus state flag Fdf(x, y) to the red-out area determination section 464.

Note that the configuration of the defocus detection section 463 is not limited to the above configuration. For example, the defocus detection section 463 may process the luminance signals using a simple high-pass filter or bandpass filter, add the absolute values of the extracted high-frequency component signals within the block area, and compare the resulting value with a threshold value to determine whether or not the block area is in a defocus state.

The red-out area determination section 464 calculates the red-out area flag Fr(x, y) by calculating the logical AND of the red-out area candidate flag Frc(x, y) and the defocus state flag Fdf(x, y). The red-out area determination section 464 approximates the boundary that encloses a plurality of block areas in which the red-out area flag Fr(x, y) is set to ON using a closed curve, for example, and determines the area enclosed by the boundary to be the red-out area (final red-out area determination result) (see FIG. 69). The red-out area determination section 464 sets the red-out area flag Fr(x, y) in the red-out area to ON, and outputs the red-out area flag Fr(x, y) to the scaling parameter setting section 465.

11.6. Scaling Parameter Setting Section

Figure 70:
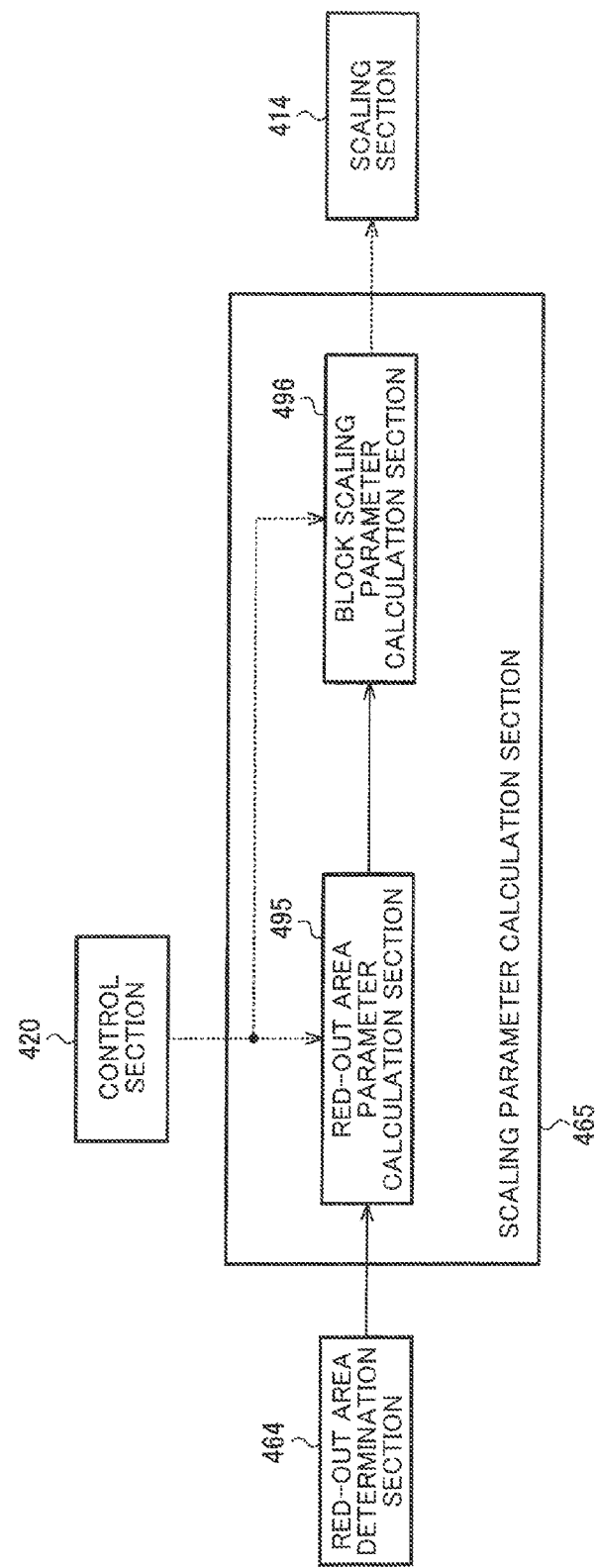
FIG. 70 illustrates a detailed configuration example of a scaling parameter setting section.

FIG. 70 illustrates a detailed configuration example of the scaling parameter setting section 465. The scaling parameter setting section 465 includes a red-out area parameter calculation section 495 and a block scaling parameter calculation section 496.

The red-out area parameter calculation section 495 is connected to the block scaling parameter calculation section 496. The block scaling parameter calculation section 496 is connected to the scaling section 414. The control section 420 is connected to the red-out area parameter calculation section 495 and the block scaling parameter calculation section 496.

Figure 69:
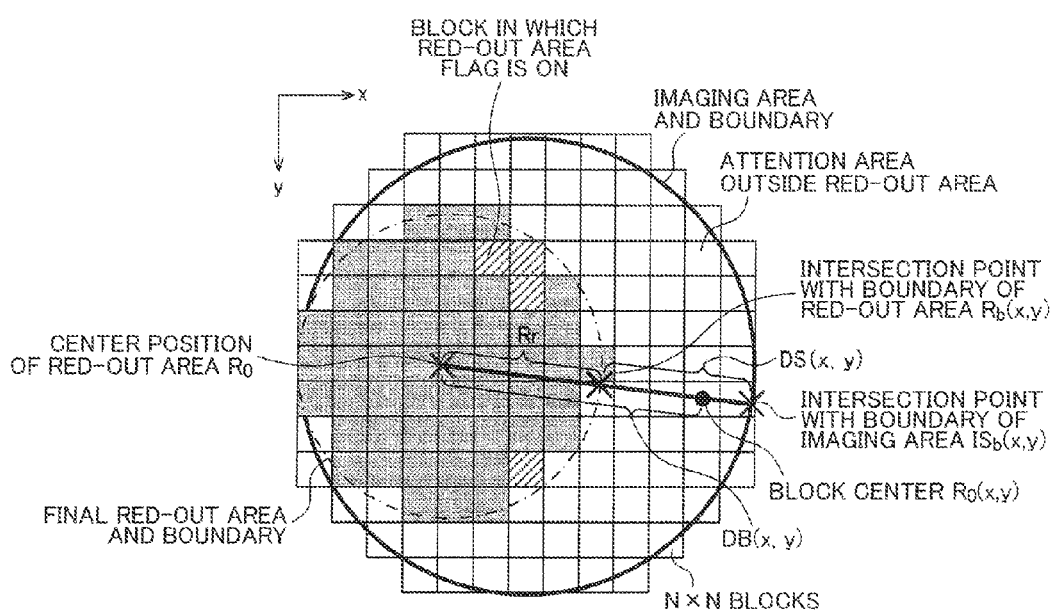
FIG. 69 is a view illustrating a process performed by an attention area setting section according to the tenth embodiment.

The red-out area parameter calculation section 495 calculates the center-of-gravity position $R_0$ of the area in which the red-out area flag Fr(x, y) is set to ON, and the maximum distance Rr from the center-of-gravity position $R_0$ to the boundary of the red-out area (see FIG. 69). Specifically, the center coordinates of the block areas in which the red-out area flag Fr(x, y) is set to ON are calculated based on the block size information output from the control section 420, and the average value of the calculated center coordinates in the red-out area is determined to be the center-of-gravity position $R_0$. The maximum distance between the center coordinates of the block areas in the red-out area and the center-of-gravity position $R_0$ is searched to determine the maximum distance Rr. The red-out area parameter calculation section 495 outputs the calculated center-of-gravity position $R_0$ and maximum distance Rr to the block scaling parameter calculation section 496.

The block scaling parameter calculation section 496 defines the red-out area using a circle based on the center-of-gravity position $R_0$ and the maximum distance Rr. Note that the area inside the circle is hereinafter referred to as the red-out area. The center of the red-out area is the center-of-gravity position $R_0$, and the radius of the red-out area is the maximum distance Rr. The entire imaging area is also defined using a circle. Note that the area inside the circle is hereinafter referred to as the imaging area. The center of the imaging area is the optical center, and is determined in advance together with the radius of the imaging area based on the optical system. The center and the radius of the imaging area are input to the block scaling parameter calculation section 496 from the control section 420.

The block scaling parameter calculation section 496 determines the scaling parameter for each block area from the red-out area and the imaging area. Specifically, the block scaling parameter calculation section 496 calculates a straight line that passes through the center position $R_0$ of the red-out area and the center position $B_0(x, y)$ of the block area. The block scaling parameter calculation section 496 calculates the intersection point $IS_b(x, y)$ of the straight line and the boundary of the imaging area, and calculates the intersection point Rb(x,y) of the straight line and the boundary of the red-out area.

The block scaling parameter calculation section 496 calculates the ratio DRatio(x, y) of the distance DS(x, y) of the line segment $|IS_b(x, y)-Rb(x,y)|$ to the distance Rr of the line segment $|R_0-Rb(x,y)|$ using the following expression (31). The block scaling parameter calculation section 496 calculates the distance DB(x, y) between the center position $R_0$ and the center position $B_0(x, y)$ using the following expression (32). The ratio DRatio(x, y) and the distance DB(x, y) are calculated for each block area.

$$\begin{aligned}DRatio(x, y) &\quad (31)\\ &= |IS_b(x, y) - R_b(x, y)|/|R_0 - R_b(x, y)|\\ &= |IS_b(x, y) - R_b(x, y)|/Rr\end{aligned}$$

$$DB(x, y) = |R_0 - B_0(x, y)| \quad (32)$$

The block scaling parameter calculation section 496 outputs the ratio DRatio(x, y), the distance DB(x, y), the center $R_0$ of the red-out area, and the radius Rr of the red-out area calculated for each block to the scaling section 414.

Figure 71:
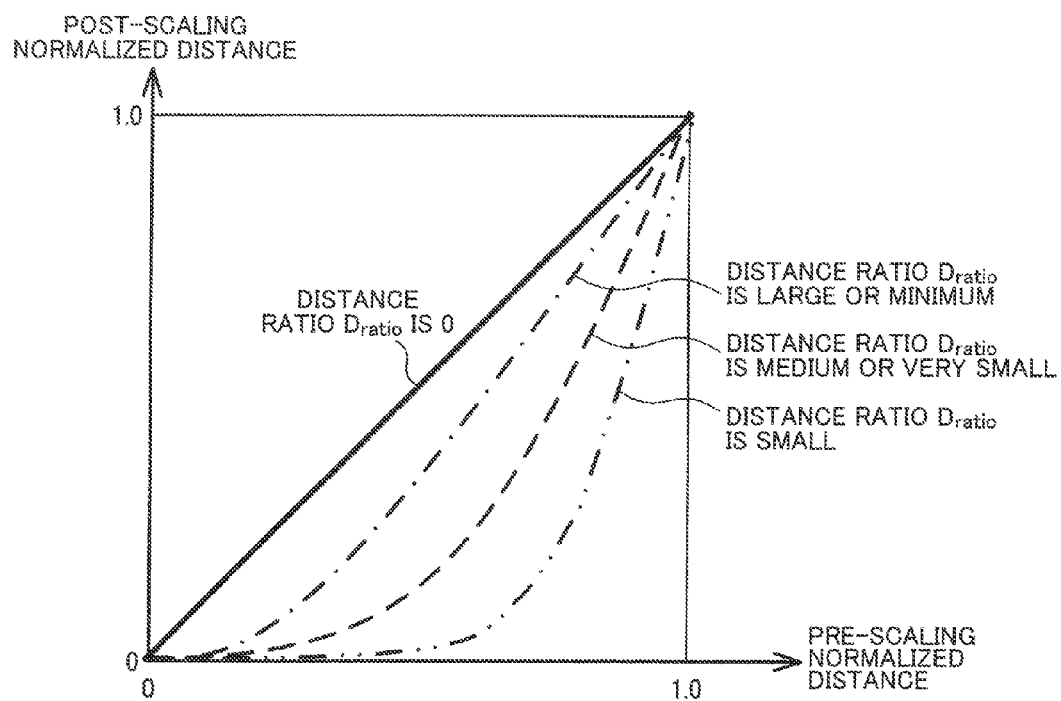
FIG. 71 illustrates an example of a plurality of post-scaling normalized distance curves with respect to a pre-scaling normalized distance.

The scaling section 414 stores the parameters for each block area input from the block scaling parameter calculation section 496 corresponding to one screen to generate a pixel-basis scaling factor conversion table. The distance ratio DRatio(x, y) of the red-out area and the non-red-out area is used to select one of a plurality of post-scaling normalized distance curves with respect to the pre-scaling normalized distance (see FIG. 71). Each curve may be stored in a look-up table (LUT), or may be expressed using a polynomial coefficient. Each curve is stored in a ROM table (not illustrated in the drawings) included in the scaling section 414. The address of the ROM table corresponds to the distance ratio DRatio(x, y).

The scaling section 414 calculates the normalized distance ND(x, y) of each block area using the following expression (33).

$$ND(x,y)=DB(x,y)/(1+DRatio(x,y))\times Rr \quad (33)$$

The scaling section 414 determines the relationship between the pre-scaling normalized distance and the post-scaling normalized distance that represents each block area (hereinafter referred to as "representative relationship") based on the calculated normalized distance ND(x, y). The representative relationship indicates the relationship between the pre-scaling normalized distance and the post-scaling normalized distance illustrated in FIG. 71. The scaling section 414 calculates the relationship between the pre-scaling normalized distance and the post-scaling normalized distance for each pixel within the attention block area by performing an interpolation process using the representative relationship of the attention block area and the representative relationship of the peripheral block area. For example, a linear interpolation process may be used as the interpolation process.

The scaling section 414 multiplies the actual distance from the center position $R_0$ of the red-out area to the pixel position P(i, j) within the attention block area by the relationship between the pre-scaling normalized distance and the post-scaling normalized distance at the pixel position P(i, j) to convert the normalized distance relationship into the actual distance relationship. Note that i and j are respectively the horizontal coordinate value and the vertical coordinate value at the pixel pitch accuracy. Since the pre-scaling pixel position (real number) corresponding to the post-scaling pixel position (integer) is situated on the line segment that connects the post-scaling pixel position P'(i, j) and the center position $R_0$ of the red-out area, the pre-scaling pixel position is uniquely determined as the coordinate value corresponding to the actual distance.

The scaling section 414 calculates the pixel value at the determined pre-scaling coordinate value by performing an interpolation process using a plurality of peripheral pixel values (at integer-based pixel positions). For example, a linear interpolation process, a bicubic interpolation process, or the like may be used as the interpolation process. An image in which the attention area other than the red-out area is enlarged relative to the red-out area can thus be generated.

Note that the red-out area determination process may always be performed, or may be manually ON/OFF-controlled using a switch (not illustrated in the drawings) that is included in the external I/F section 550. Specifically, the user may start the red-out area determination process by operating the switch when the user has determined that a red-out area has occurred.

According to the tenth embodiment, the captured image is an in vivo image. The attention area setting section 413 includes a contact state information acquisition section (i.e., the color conversion section 461, the red-out area candidate detection section 462, the defocus detection section 463, and the red-out area determination section 464 illustrated in FIG. 65). The contact state information acquisition section acquires contact state information about the contact state between the end of the scope and tissue (red-out area information) based on the captured image. The attention area setting section 413 sets the attention area based on the contact state information.

The contact state information acquisition section may detect a specific color area of the captured image that has a color within a specific color range (i.e., a color area that indicates the red-out area in the hue plane), and may set a contact area based on the specific color area. The attention area setting section 413 may set an area other than the contact area to be the attention area.

For example, the red-out area candidate detection section 462 (specific color area detection section in a broad sense) detects the specific color area, and the red-out area determination section 464 (contact area setting section in a broad sense) sets the contact area.

The above configuration makes it possible to determine the contact area (red-out area (unobservable area in a broad sense)) with tissue, set an area other than the contact area to be the attention area, and enlarge the attention area. When using a wide-angle optical system that produces image distortion, the insertion direction along the lumen may be displayed in an area other than the contact area. Therefore, it is possible to improve the visibility of the insertion direction, and reduce the insertion time by enlarging an area other than the contact area.

The contact state information acquisition section may convert the image of the specific color area into spatial frequency components, and may set the specific color area to be the contact area when the spatial frequency components are equal to or smaller than a given threshold value. For example, the contact state information acquisition section may set the specific color area to be the contact area when the highest frequency of the spatial frequency components at which the amplitude value is equal to or larger than a given value is equal to or smaller than a first threshold value, or the sum of the amplitude values of the spatial frequency components is equal to or smaller than a second threshold value.

For example, the defocus detection section 463 (spatial frequency conversion section in a broad sense) may convert the image of the specific color area into spatial frequency components, and may determine whether or not the spatial frequency components are equal to or smaller than a given threshold value.

According to the above configuration, since it is considered that the amount of high-frequency components of the image is small in the contact area due to a defocus state, the contact area can be detected by comparing the high-frequency components in the specific color area with a threshold value.

The contact state information acquisition section may set a circle that encloses the specific color area, and may set an area enclosed by the circle to be the contact area (see FIG. 69).

The scaling section 414 may set the scaling factor (enlargement factor) (i.e., the relationship between the pre-scaling normalized distance and the post-scaling normalized distance (see FIG. 71)) for the attention area based on the ratio DRatio(x, y) of the distance Rr from the center to the circumference of the circle that defines the contact area and the distance DS(x, y) from the circumference of the circle that defines the contact area to the periphery of the captured image (i.e., the periphery of the imaging area) along the straight line that connects the center of the circle that defines the contact area and the periphery of the captured image.

The contact state information is information that indicates the position (i.e., the center position $R_0$ of the circle) and the size (radius Rr) of the contact area.

This makes it possible to enlarge the attention area by the scaling process along the straight line that connects the center of the circle that defines the contact area and the periphery of the captured image.

12. Software

Although an example in which each section of the image processing section 410 is implemented by hardware has been described above, another configuration may also be employed. For example, a CPU may perform the process of each section on an image acquired using an imaging apparatus such as a capsule endoscope. Specifically, the process of each section may be implemented by software by causing the CPU to execute a program. Alternatively, part of the process of each section may be implemented by means of software. The image acquired in advance is a Bayer array image that is output from the A/D conversion section 305, and recorded on a recording medium as a RAW file, for example.

When separately providing the imaging section, and implementing the process of each section of the image processing section 410 by means of software, a known computer system (e.g., work station or personal computer) may be used as an image processing device. A program (image processing program) that implements the process of each section of the image processing section 410 may be provided in advance, and executed by the CPU of the computer system.

Figure 72:
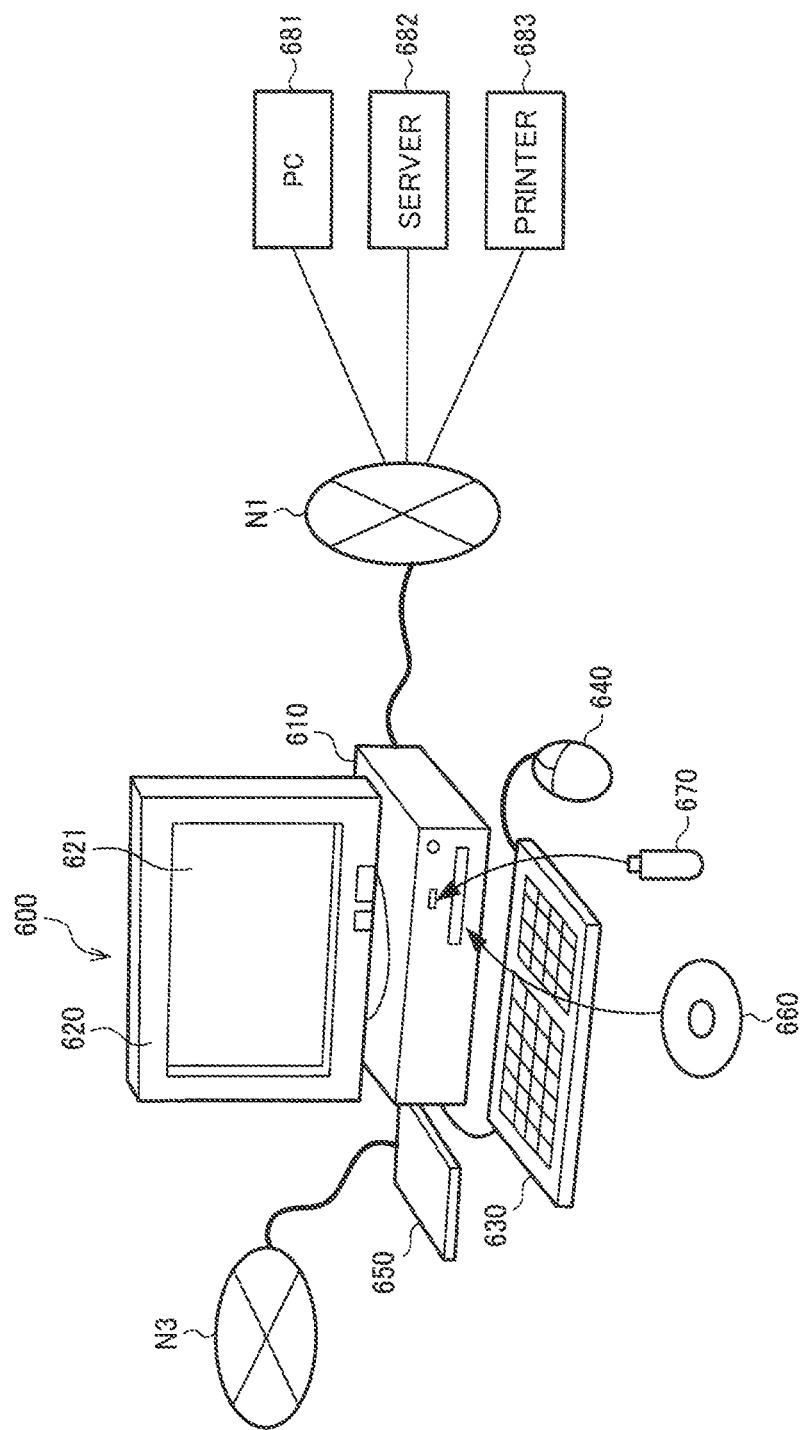
FIG. 72 is a system configuration diagram illustrating the configuration of a computer system.
Figure 73:
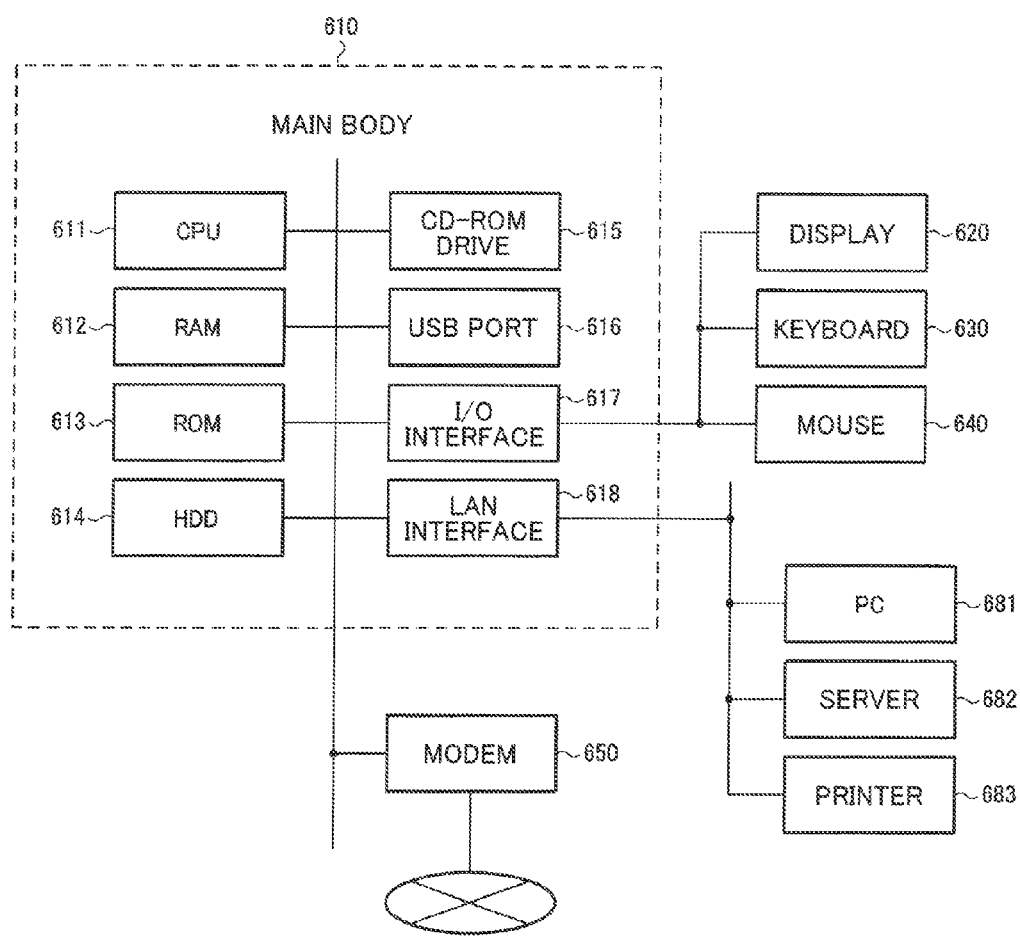
FIG. 73 is a block diagram illustrating the configuration of a main body of a computer system.

FIG. 72 is a system configuration diagram illustrating the configuration of a computer system 600 according to this modification. FIG. 73 is a block diagram illustrating the configuration of a main body 610 of the computer system 600. As shown in FIG. 72, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As illustrated in FIG. 73, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to a personal computer (PC) 681 (i.e., another computer system), a server 682, a printer 683, and the like via the LAN interface 618 and the local area network or the large area network N1.

The computer system 600 implements the functions of the image processing device by reading an image processing program (e.g., see FIGS. 18 to 20) recorded on a given recording medium, and executing the image processing program. The given recording medium may be an arbitrary recording medium that records the image processing program that can be read by the computer system 600, such as the CD-ROM 660, the USB memory 670, a portable physical medium (e.g., MO disk, DVD disk, flexible disk (FD), magnetooptical disk, or IC card), a stationary physical medium (e.g., HDD 614, RAM 612, or ROM 613) that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the image processing program is recorded in a recording medium (e.g., portable physical medium, stationary physical medium, or communication medium) so that the image processing program can be read by a computer. The computer system 600 implements the functions of the image processing device by reading the image processing program from such a recording medium, and executing the image processing program. Note that the image processing program need not necessarily be executed by the computer system 600. The invention may be similarly applied to the case where the computer system (PC) 681 or the server 682 executes the image processing program, or the computer system (PC) 681 and the server 682 execute the image processing program in cooperation.

The embodiments of the invention may also be applied to a computer program product that stores a program code that implements each section (e.g., control section, image processing section, and state information acquisition section) according to the embodiments of the invention.

The term "computer program product" refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to the embodiments are implemented by corresponding modules, and a program code that includes these modules is recorded in the computer program product.

Although only some embodiments of the invention and the modifications thereof have been described in detail above, those skilled in the art will readily appreciate that many modifications are possible in the embodiments and the modifications thereof without materially departing from the novel teachings and advantages of the invention. A plurality of elements described in connection with the above embodiments and the modifications thereof may be appropriately combined to implement various configurations. For example, some of the elements described in connection with the above embodiments and the modifications thereof may be omitted. The elements described in connection with different embodiments and modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

What is claimed is:

1. An endoscope system comprising:
an imaging device that acquires a captured image that includes an object image; and
a control device configured to set an attention area within the captured image, and perform a local scaling process that relatively enlarges the attention area as compared with another area while maintaining an angle of view of the captured image,
wherein the captured image is an in vivo image, and
wherein the control device is configured to acquire contact state information about a contact state between an end of a scope and tissue based on the captured image, set a contact area in the captured image corresponding to contact between the end of the scope and the tissue, and set an area other than the contact area to be the attention area.

2. The endoscope system as defined in claim 1, wherein the control device is configured to detect a specific color area of the captured image that has a color within a specific color range, and set the contact area based on the specific color area.

3. The endoscope system as defined in claim 2, wherein the control device is configured to convert an image of the specific color area into spatial frequency components, and set the specific color area to be the contact area when a highest frequency of the spatial frequency components at which an amplitude value is equal to or larger than a given value is equal to or smaller than a first threshold value, or a sum of amplitude values of the spatial frequency components is equal to or smaller than a second threshold value.

4. The endoscope system as defined in claim 2, wherein the control device is configured to set a circle that encloses the specific color area, and set an area enclosed by the circle to be the contact area, and
wherein the control device is configured to set an enlargement factor for the attention area based on a ratio of a distance from a center to a circumference of the circle and a distance from the circumference of the circle to a periphery of the captured image along a straight line that connects the center of the circle that defines the contact area and the periphery of the captured image.

5. The endoscope system as defined in claim 2, wherein the contact state information is information that indicates a position and a size of the contact area.

6. A method for operating an endoscope system comprising:
acquiring a captured image that includes an object image, wherein the captured image is an in vivo image;
acquiring contact state information about a contact state between an end of a scope and tissue based on the captured image, and setting a contact area in the captured image corresponding to contact between the end of the scope and the tissue;
setting an area other than the contact area to be an attention area within the captured image; and performing a local scaling process that relatively enlarges the attention area as compared with another area while maintaining an angle of view of the captured image.

* * * * *